United States Patent
Lu et al.

(10) Patent No.: US 8,367,416 B2
(45) Date of Patent: Feb. 5, 2013

(54) NUCLEIC ACID BASED FLUORESCENT SENSOR FOR MERCURY DETECTION

(75) Inventors: Yi Lu, Champaign, IL (US); Juewen Liu, Kitchener (CA)

(73) Assignee: The Board of Trustees of the University of Illinois, Urbana, IL (US)

(*) Notice: Subject to any disclaimer, the term of this patent is extended or adjusted under 35 U.S.C. 154(b) by 0 days.

(21) Appl. No.: 12/672,833

(22) PCT Filed: Aug. 6, 2008

(86) PCT No.: PCT/US2008/072327
§ 371 (c)(1),
(2), (4) Date: Feb. 9, 2010

(87) PCT Pub. No.: WO2009/045632
PCT Pub. Date: Apr. 9, 2009

(65) Prior Publication Data
US 2012/0149119 A1    Jun. 14, 2012

Related U.S. Application Data

(60) Provisional application No. 60/955,316, filed on Aug. 10, 2007.

(51) Int. Cl.
*G01N 21/77* (2006.01)
*G01N 21/00* (2006.01)
*C07H 21/00* (2006.01)

(52) U.S. Cl. ........ 436/81; 436/73; 422/82.05; 422/68.1; 422/50

(58) Field of Classification Search ............ 436/73, 436/81; 422/82.05, 68.1, 50
See application file for complete search history.

(56) References Cited

U.S. PATENT DOCUMENTS

| | | | |
|---|---|---|---|
| 4,362,603 A | 12/1982 | Presson et al. |
| 4,703,017 A | 10/1987 | Campbell et al. |
| 4,746,631 A | 5/1988 | Clagett |
| 4,855,240 A | 8/1989 | Rosenstein et al. |
| 4,857,319 A | 8/1989 | Crowe et al. |
| 5,008,109 A | 4/1991 | Tin |
| 5,459,040 A | 10/1995 | Hammock et al. |
| 5,472,881 A | 12/1995 | Beebe et al. |
| 5,580,967 A | 12/1996 | Joyce |
| 5,593,835 A | 1/1997 | Rando et al. |
| 5,631,148 A | 5/1997 | Urdea |
| 5,663,064 A | 9/1997 | Burke et al. |
| 5,807,718 A | 9/1998 | Joyce et al. |
| 5,807,967 A | 9/1998 | Snow et al. |

(Continued)

FOREIGN PATENT DOCUMENTS

| | | |
|---|---|---|
| EP | 121970 | 10/1984 |
| EP | 1219708 | 7/2002 |

(Continued)

OTHER PUBLICATIONS

Ono et al.,Highly Selective Oligonucleotide-Based Sensor for Mercury(ii) in Aqueous Solutions Agnew. Chem. Int. Ed. 2004, 43, 4300-4302.*

(Continued)

*Primary Examiner* — Christine T Mui
(74) *Attorney, Agent, or Firm* — Klarquist Sparkman, LLP

(57) ABSTRACT

A nucleic acid enzyme comprises an oligonucleotide containing thymine bases. The nucleic acid enzyme is dependent on both $Hg^{2+}$ and a second ion as cofactors, to produce a product from a substrate. The substrate comprises a ribonucleotide, a deoxyribonucleotide, or both.

28 Claims, 6 Drawing Sheets

U.S. PATENT DOCUMENTS

| | | | |
|---|---|---|---|
| 5,910,408 A | 6/1999 | Szostak et al. |
| 5,989,813 A | 11/1999 | Gerdes |
| 6,040,138 A | 3/2000 | Lockhart et al. |
| 6,110,462 A | 8/2000 | Barbas et al. |
| 6,159,347 A | 12/2000 | Sumner, Jr. et al. |
| 6,287,765 B1 | 9/2001 | Cubicciotti |
| 6,316,194 B1 | 11/2001 | Karn et al. |
| 6,326,508 B1 | 12/2001 | Godbole et al. |
| 6,361,944 B1 | 3/2002 | Mirkin et al. |
| 6,387,617 B1 | 5/2002 | Asher et al. |
| 6,426,335 B1 | 7/2002 | Janjic et al. |
| 6,451,535 B1 | 9/2002 | Jenne et al. |
| 6,485,982 B1 | 11/2002 | Charlton |
| 6,541,617 B1 | 4/2003 | Bamdad et al. |
| 6,630,306 B1 | 10/2003 | Breaker |
| 6,706,474 B1 | 3/2004 | Lu et al. |
| 6,818,455 B2 | 11/2004 | May et al. |
| 6,843,890 B1 | 1/2005 | Godbole |
| 6,849,414 B2 | 2/2005 | Guan et al. |
| 6,890,719 B2 | 5/2005 | Lu et al. |
| 7,109,165 B2 | 9/2006 | Matulic-Adamic et al. |
| 7,192,708 B2 | 3/2007 | Lu et al. |
| 7,332,283 B2 | 2/2008 | Lu et al. |
| 7,459,145 B2 | 12/2008 | Bao et al. |
| 7,485,419 B2 | 2/2009 | Lu et al. |
| 7,534,560 B2 | 5/2009 | Lu et al. |
| 7,612,185 B2 | 11/2009 | Lu et al. |
| 7,799,554 B2 | 9/2010 | Mazumdar et al. |
| 7,829,350 B2 | 11/2010 | Josephson et al. |
| 7,892,734 B2 | 2/2011 | Lu et al. |
| 7,902,353 B2 | 3/2011 | Lu et al. |
| 7,906,320 B2 | 3/2011 | Lu et al. |
| 2003/0149257 A1 | 8/2003 | Sorge et al. |
| 2003/0215810 A1 | 11/2003 | Lu et al. |
| 2003/0235611 A1 | 12/2003 | Ehringer et al. |
| 2004/0018515 A1 | 1/2004 | Diener et al. |
| 2004/0110167 A1 | 6/2004 | Gerdes et al. |
| 2004/0126882 A1 | 7/2004 | Ellington et al. |
| 2004/0158051 A1 | 8/2004 | Ozkan et al. |
| 2004/0175693 A1 | 9/2004 | Lu et al. |
| 2005/0037075 A1 | 2/2005 | Farokhzad et al. |
| 2005/0136500 A1 | 6/2005 | Yang et al. |
| 2005/0282186 A1 | 12/2005 | Lu et al. |
| 2006/0019406 A1 | 1/2006 | Wei et al. |
| 2006/0040408 A1 | 2/2006 | Jones et al. |
| 2006/0045910 A1 | 3/2006 | Ehringer |
| 2006/0094026 A1 | 5/2006 | Lu et al. |
| 2006/0166222 A1 | 7/2006 | Lu et al. |
| 2007/0037171 A1 | 2/2007 | Lu et al. |
| 2007/0269821 A1 | 11/2007 | Mazumdar et al. |
| 2008/0176228 A1 | 7/2008 | Lu et al. |
| 2009/0011402 A1 | 1/2009 | Lu et al. |
| 2009/0029874 A1 | 1/2009 | Lu et al. |
| 2009/0197261 A1 | 8/2009 | Lu et al. |
| 2010/0105039 A1 | 4/2010 | Lu et al. |
| 2010/0151579 A1 | 6/2010 | Wang et al. |
| 2010/0166842 A1 | 7/2010 | Lu et al. |
| 2011/0123982 A1 | 5/2011 | Lu et al. |
| 2011/0171635 A1 | 7/2011 | Lu et al. |

FOREIGN PATENT DOCUMENTS

| | | |
|---|---|---|
| EP | 1 312 674 | 5/2003 |
| GB | 2339280 | 1/2000 |
| WO | WO 91/14696 | 10/1991 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/23548 | 4/2001 |
| WO | WO 01/024696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |
| WO | WO 02/00006 | 1/2002 |
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | WO 2004/046687 | 6/2004 |
| WO | WO 2004/081235 | 9/2004 |
| WO | WO 2005/082922 | 9/2005 |
| WO | WO 2005/095967 | 10/2005 |
| WO | WO 2005/100602 | 10/2005 |
| WO | WO 2006/020768 | 2/2006 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |
| WO | WO 2008/089248 | 7/2008 |
| WO | WO 2009/012309 | 1/2009 |
| WO | WO 2009/045632 | 4/2009 |

OTHER PUBLICATIONS

Abstract of Joyce, G., "Design and catalytic activity of enzyumic DNA molecules", (1998).

Aggarwal, S.K., et al., "Determination of lead in urine and whole blood by stable isotope dilution gas chromatography-mass spectrometry", Clinical Chemistry, vol. 40, No. 8, pp. 1494-1502, (1994).

Alivisatos, A.P., et al., "Organization of "nanocrystal molecules" using DNA", Nature, vol. 382, pp. 609-611, (1996).

Allara, D. et al., "Spontaneously organized molecular assemblies. 1.Formation, dynamics and physical properties of n-alkanoic acids adsorbed from solution on an oxidized aluminum surface", Langmuir, vol. 1, No. 1, pp. 45-52, (1985).

Andreola, M-L., et al., "DNA aptamers selected against the HIV-1 RNase H display in vitro antiviral activity", Biochemistry, vol. 40, No. 34, pp. 10087-10094, (2001).

Bain, C. D., et al., "Modeling organic surfaces with self-assembled monolayers", Angew. Chem. Int. Ed. Engl., vol. 28, No. 4, pp. 506-512, (1989).

Bannon, D.I., et al., "Graphite furnace atomic absorption spectroscopic measurement of blood lead in matrix-matched standards", Clinical Chemistry, vol. 40, No. 9, pp. 1730-1734, (1994).

Been, M.D., et al., "Self-cleaving ribozymes of hepatitis delta virus RNA", Eur. J. Biochem., vol. 247, pp. 741-753, (1997).

Berens, C., et al., "A tetracycline-binding RNA aptamer", Bioorganic & Medicinal Chemistry, vol. 9, pp. 2549-2556, (2001).

Biroccio, A., et al., "Selection of RNA aptamers that are specific and high-affinity ligands of the hepatitis C virus RNA-dependent RNA polymerase", Journal of Virology, vol. 76, No. 8, pp. 3688-3696, (2002).

Blake, D.A., et al., "Antibody-based sensors for heavy metal ions", Biosensors & Bioelectronics, vol. 16, pp. 799-809, (2001).

Blank, M., et al., "Systematic evolution of a DNA aptamer binding to rat brain tumor microvessels. Selective targeting of endothelial regulatory protein pigpen", Journal of Biological Chemistry, vol. 276, No. 19, pp. 16464-16468, (2001).

Bock, L.C., et al., "Selection of single-stranded DNA molecules that bind and inhibit human thrombin", Nature, vol. 355, pp. 564-566, (1992).

Bogden, J.D., et al., "Soil contamination from lead in paint chips", Bulletin of Environmental Contamination & Toxicology, vol. 14, No. 3, pp. 289-294, (1975).

Boiziau, C., et al., "DNA aptamers selected against the HIV-1 trans-activation-responsive RNA element form RNA-DNA kissing complexes", Journal of Biological Chemistry, vol. 274, No. 18, pp. 12730-12737, (1999).

Bowins, R.J., et al., "Electrothermal isotope dilution inductively coupled plasma mass spectrometry method for the determination of sub-ng ml$^{-1}$ levels of lead in human plasma", Journal of Analytical Atomic Spectrometry, vol. 9, pp. 1233-1236, (1994).
Breaker, R.R., "Catalytic DNA: in training and seeking employment", Nature Biotechnology, vol. 17, pp. 422-423, (1999).
Breaker, R.R., "DNA aptamers and DNA enzymes" Current Opinion in Chemical Biology, vol. 1, pp. 26-31, (1997).
Breaker, R.R., "DNA enzymes", Nature Biotechnology, vol. 15, pp. 427-431, (1997).
Breaker, R.R., "Molecular Biology: Making Catalytic DNAs", Science, vol. 290, issue 5499, pp. 2095-2096, (2000).
Breaker, R.R., et al., "A DNA enzyme that cleaves RNA", Chemistry & Biology, vol. 1, No. 4, pp. 223-229, (1994).
Breaker, R.R., et al., "A DNA enzyme with Mg$^{2+}$-dependent RNA phosphoesterase activity", Chemistry & Biology, vol. 2, No. 10, pp. 655-660, (1995).
Breaker, R.R., et al., "Engineered allosteric ribozymes as biosensor components", Current Opinion in Biotechnology, vol. 13, pp. 31-39, (2002).
Brody, E.N., et al., "Aptamers as therapeutic and diagnostic agents", Reviews in Molecular Biotechnology, vol. 74, pp. 5-13, (2000).
Broude, N.E., "Stem-loop oligonucleotides: a robust tool for molecular biology and biotechnology", Trends in Biotechnology, vol. 20, No. 6, pp. 249-256, (2002).
Brown, A.K., et al., "A lead-dependent DNAzyme with a two-step mechanism", Biochemistry, vol. 42, No. 23, pp. 7152-7161, (2003).
Bruesehoff, P.J., et al., "Improving metal ion specificity during In Vitro selection of catalytic DNA", Combinatorial Chemistry & High Throughput Screening, vol. 5, pp. 327-335, (2002).
Bruno, J.G., et al., "In vitro selection of DNA aptamers to anthrax spores with electrochemiluminescence detection", Biosensors & Bioelectronics, vol. 14, pp. 457-464, (1999).
Bruno, J.G., et al., "Use of magnetic beads in selection and detection of biotoxin aptamers by electrochemiluminescence and enzymatic methods", BioTechniques, vol. 32, No. 1, pp. 178-180, pp. 182-183, (2002).
Brust, M., et al., "Novel gold-dithiol nano-networks with non-metallic electronic properties", Advanced Materials, vol. 7, No. 9, pp. 795-797, (1995).
Burdette, S.C., et al., "Fluorescent Sensors for Zn$^{2+}$Based on a Fluorescein Platform: Synthesis, Properties and Intracellular Distribution", J. Am. Chem. Soc., vol. 123, No. 32, pp. 7831-7841, (2001).
Burgstaller, P., et al., "Isolation of RNA aptamers for biological cofactors by in vitro selection", Angew. Chem. Int. Ed. Engl, vol. 33, No. 10, pp. 1084-1087, (1994).
Burgstaller, P., et al., "Structural probing and damage selection of citrulline- and arginine-specific RNA aptamers identify base positions required for binding", Nucleic Acids Research, vol. 23, No. 23, pp. 4769-4776, (1995).
Burke, D.H., et al., "A Novel Acidophilic RNA Motif That Recognizes Coenzyme A", Biochemistry, vol. 37, No. 13, pp. 4653-4663, (1998).
Burke, D.H., et al., "RNA aptamers to the adenosine moiety of S-adenosyl methionine: structural inferences from variations on a theme and the reproducibility of SELEX", Nucleic Acids Research, vol. 25, No. 10, pp. 2020-2024, (1997).
Burke, D.H., et al., "RNA aptamers to the peptidyl transferase inhibitor chloramphenicol", Chemistry & Biology, vol. 4, No. 11, pp. 833-843, (1997).
Burmeister, J., et al., "Cofactor-assisted self-cleavage in DNA libraries with a 3'-5'-phosphoramidate bond", Angew. Chem. Int. Ed. Engl., vol. 36, No. 12, pp. 1321-1324, (1997).
Burwell Jr., R.L., "Modified silica gels as adsorbents and catalysts", Chemical Technology, 4, pp. 370-377, (1974).
Cadwell, R.C., et al., "Mutagenic PCR", PCR Methods and Applications, vol. 3, pp. S136-S140, (1994).
Cadwell, R.C., et al., "Randomization of genes by PCR mutagenesis", PCR Methods and Applications, vol. 2, pp. 28-33, (1992).
Cake, K.M., et al., "In vivo x-ray fluorescence of bone lead in the study of human lead metabolism: serum lead, whole blood lead, bone lead, and cumulative exposure", Advances in X-Ray Analysis, vol. 38, pp. 601-606, (1995).

Camara Rica, C., et al., "Determination of trace concentrations of lead and nickel in human milk by electrothermal atomisation atomic absorption spectrophotometry and inductively coupled plasma emission spectroscopy", The Science of the Total Environment, vol. 22, pp. 193-201, (1982).
Cao, Y.W., et al., "DNA-modified core-shell Ag/Au nanoparticles", J. Am. Chem. Soc., vol. 123, No. 32, pp. 7961-7962, (2001).
Carmi, N., et al., "Cleaving DNA with DNA", Proc. Natl. Acad. Sci. USA, vol. 95, pp. 2233-2237, (1998).
Carmi, N., et al., "In vitro selection of self-cleaving DNAs", Chemistry & Biology, vol. 3, No. 12, pp. 1039-1046, (1996).
Cech, T.R., "Structure and mechanism of the large catalytic RNAs: group I and group II introns and ribonuclease P", The RNA World, pp. 239-269, Cold Spring Harbor Laboratory Press, Cold Spring Harbor, New York, (1993).
Cech, T.R., et al., "Group I ribozymes: substrate recognition, catalytic strategies, and comparative mechanistic analysis", Nucleic Acids and Molecular Biology, vol. 10, pp. 1-17, (1996).
Chaloin, L., et al., "Endogenous expression of a high-affinity pseudoknot RNA aptamer suppresses replication of HIV-1", Nucleic Acids Research, vol. 30, No. 18, pp. 4001-4008, (2002).
Chapman, K.B., et al., "In vitro selection of catalytic RNAs", Current Opinion in Structural Biology, vol. 4, pp. 618-622, (1994).
Chartrand, P., et al., "Effect of structural modifications on the activity of the leadzyme", Biochemistry, vol. 36, No. 11, pp. 3145-3150, (1997).
Chen, J., et al., "Synthesis from DNA of a molecule with the connectivity of a cube", Nature, vol. 350, pp. 631-633, (1991).
Chen, C-T., et al., "A highly selective fluorescent chemosensor for lead ions", J. Am. Chem. Soc., vol. 124, pp. 6246-6247, (2002).
Chen, J-H., et al., "A specific quadrilateral synthesized from DNA branched junctions", J. Am. Chem. Soc., vol. 111, No. 16, pp. 6402-6407, (1989).
Chen, L., et al., "Crystal structure of a four-stranded intercalated DNA: d(C$_4$)", Biochemistry, vol. 33, No. 46, pp. 13540-13546, (1994).
Chinnapen, D.J.F., et al., "Hemin-stimulated docking of cytochrome c to a hemin—DNA aptamer complex", Biochemistry, vol. 41, No. 16, pp. 5202-5212, (2002).
Ciesiolka, J., et al., "Selection of an RNA domain that binds Zn$^{2+}$", RNA, vol. 1, pp. 538-550, (1995).
Ciesiolka, J., et al., "Small RNA-divalent domains", RNA, vol. 2, pp. 785-793, (1996).
Conaty, J., et al., "Selected classes of minimised hammerhead ribozyme have very high cleavage rates at low Mg$^{2+}$concentration", Nucleic Acids Research, vol. 27, No. 11, pp. 2400-2407, (1999).
Conn, M.M., et al., "Porphyrin Metalation Catalyzed by a Small RNA Molecule", J. Am. Chem. Soc, vol. 118, No. 29, pp. 7012-7013, (1996).
Connell, G.J., et al., "RNAs with dual specificity and dual RNAs with similar specificity", Science, New Series, vol. 264, issue 5162, pp. 1137-1141, (1994).
Connell, G.J., et al., "Three small ribooligonucleotides with specific arginine sites", Biochemistry, vol. 32, No. 21, pp. 5497-5502, (1993).
Cuenoud, B., et al., "A DNA metalloenzyme with DNA ligase activity", Nature, vol. 375, pp. 611-614, (1995).
Czarnik, A.W., "Desperately seeking sensors", Chemistry & Biology, vol. 2, No. 7, pp. 423-428, (1995).
Dai, X., et al., "Cleavage of an amide bond by a ribozyme", Science, New Series, vol. 267, issue 5195, pp. 237-240, (1995).
Davis, J.H., et al., "Isolation of high-affinity GTP aptamers from partially structured RNA libraries", Proc. Natl. Acad. Sci. USA, vol. 99, No. 18, pp. 11616-11621, (2002).
Davis, K.A., et al., "Staining of cell surface human CD4 with 2'-F-pyrimidine-containing RNA aptamers for flow cytometry", Nucleic Acids Research, vol. 26, No. 17, pp. 3915-3924, (1998).
Definition of the word "ion" printed from Merriam-Webster online dictionary (www,m-w.com) on Jun. 30, 2004.
Definition of the word "particle" printed from Merriam-Webster online dictionary (www.rn-w.com) on Jun. 29, 2004.
Deo, S., et al., "A Selective, Ratiometric Fluorescent Sensor for Pb$^{2+}$" J. Am. Chem. Soc., vol. 122, No. 1, pp. 174-175, (2000).

Derose, V.J., "Two Decades of RNA Catalysis", Chemistry & Biology, vol. 9, pp. 961-969, (2002).
Didenko, V.V., "DNA probes using fluorescence resonance energy transfer (FRET): Designs and applications", BioTechniques, vol. 31, pp. 1106-1121, (2001).
Doudna, J.A., et al., "The Chemical Repertoire of Natural Ribozymes", Nature, vol. 418, pp. 222-228, (2002).
Dubois, L.H., et al., "Synthesis, structure, and properties of model organic surfaces", Annu. Rev. Phys. Chem., vol. 43, pp. 437-463, (1992).
Earnshaw, D.J., et al., "Modified oligoribonucleotides as site-specific probes of RNA structure and function", Biopolymers (Nucleic Acid Sciences), vol. 48, pp. 39-55, (1998).
Ekland, E.H., et al., "RNA-catalysed RNA polymerization using nucleoside triphosphates", Nature, vol. 382, pp. 373-376, (1996).
Ekland, E.H., et al., "Structurally complex and highly active RNA ligases derived from random RNA sequences", Science, vol. 269, issue 5222, pp. 364-370, (1995).
Elghanian, R., et al., "Selective colorimetric detection of polynucleotides based on the distance-dependent optical properties of gold nanoparticles", Science, vol. 277, pp. 1078-1081, (1997).
Ellington, A.D., et al., "Aptamers as potential nucleic acid pharmaceuticals", Biotechnology Annual Review, vol. 1, pp. 185-214, (1995).
Ellington, A.D., et al., "In vitro selection of RNA molecules that bind specific ligands", Nature, vol. 346, pp. 818-822, (1990).
Ellington, A.D., et al., "Selection in vitro of single-stranded DNA molecules that fold into specific ligand-binding structures", Nature, vol. 355, pp. 850-852, (1992).
Famulok, M., "Molecular Recognition of Amino Acids by RNA-Aptamers: An L-Citrulline Binding RNA Motif and Its Evolution into an L-Arginine Binder", J. Am. Chem. Soc., vol. 116, No. 5, pp. 1698-1706, (1994).
Famulok, M., "Oligonucleotide aptamers that recognize small molecules", Current Opinion in Structural Biology, vol. 9, pp. 324-329, (1999).
Famulok, M., et al., "In Vitro Selection Analysis of Neomycin Binding RNAs with a Mutagenized Pool of Variants of the 16S rRNA Decoding Region", Biochemistry, vol. 35, No. 14, pp. 4265-4270, (1996).
Famulok, M., et al., "Stereospecific recognition of tryptophan agarose by in vitro selected RNA", J. Am. Chem. Soc., vol. 114, No. 10, pp. 3990-3991, (1992).
Faulhammer, D., et al., "Characterization and Divalent Metal-ion Dependence of in Vitro Selected Deoxyribozymes which Cleave DNA/RNA Chimeric Oligonucleotides", J. Mol. Biol., vol. 269, pp. 188-202, (1997).
Faulhammer, D., et al., "The $Ca^{2+}$ ion as a cofactor for a novel RNA-cleaving deoxyribozyme", Angew. Chem., Int. Ed. Engl., vol. 35, No. 23/24, pp. 2837-2841, (1996).
Feldman, B.J., et al., "Determination of lead in blood by square wave anodic stripping voltammetry at a carbon disk ultramicroelectrode", Analytical Chemistry, vol. 66, No. 13, pp. 1983-1987, (1994).
Ferguson, A., et al., "A novel strategy for selection of allosteric ribozymes yields riboreporter™ sensors for caffeine and aspartame", Nucleic Acids Research, vol. 32, No. 5, pp. 1756-1766, (2004).
Fodor, S.P.A., et al., "Light-directed, spatially addressable parallel chemical synthesis", Science, New Series, vol. 251, issue 4995, pp. 767-773, (1991).
Frank, D.N., et al., "In vitro selection for altered divalent metal specificity in the RNase P RNA", Proc. Natl. Acad. Sci. USA, vol. 94, pp. 14355-14360, (1997).
Frens, G., "Controlled Nucleation for the regulation of the particle size in monodisperse gold suspensions", Nature Physical Science, vol. 241, pp. 20-22, (1973).
Fukusaki, E-I., et al., "DNA aptamers that bind to chitin", Bioorganic & Medicinal Chemistry letters, vol. 10, pp. 423-425, (2000).
Geiger, A., et al., "RNA aptamers that bind L-arginine with sub-micromolar dissociation constants and high enantioselectivity", Nucleic Acids Research, vol. 24, No. 6, pp. 1029-1036, (1996).
Geyer, C.R., et al., "Evidence for the metal-cofactor independence of an RNA phosphodiester-cleaving DNA enzyme", Chemistry & Biology, vol. 4, No. 8, pp. 579-593, (1997).

Geyer, C.R., et al., "Lanthanide Probes for a Phosphodiester-cleaving, Lead-dependent, DNAzyme", J. Mol. Biol., vol. 275, pp. 483-489, (1998).
Giver, L., et al., "Selection and design of high-affinity RNA ligands for HIV-1 Rev", Gene, vol. 137, pp. 19-24, (1993).
Giver, L., et al., "Selective optimization of the Rev-binding element of HIV-1",Nucleic Acids Research, vol. 21, No. 23, pp. 5509-5516, (1993).
Godwin, H.A., et al., "A Flourescent Zinc Probe Based on Metal-Induced Peptide Folding", J. Am. Chem. Soc., vol. 118, pp. 6514-6515, (1996).
Grabar, K., et al., "Preparation and characterization of Au colloid Monolayers", Analytical chemistry, vol. 67, No. 4, pp. 735-743, (1995).
Granadillo, V.A., et al., "The influence of the blood levels of lead, aluminum and vanadium upon the arterial hypertension", Clinica Chimica Acta, vol. 233, pp. 47-59, (1995).
Grate, D., et al., "Laser-mediated, site-specific inactivation of RNA transcripts", Proc. Natl. Acad. Sci. USA, vol. 96, pp. 6131-6136, (1999).
Guschin, D., et al., "Manual manufacturing of oligonucleotide, DNA, and protein microchips", Analytical Biochemistry, vol. 250, pp. 203-211, (1997).
Haller, A.A., et al., "In vitro selection of a 7-methyl-guanosine binding RNA that inhibits translation of capped mRNA molecules", Proc. Natl. Acad. Sci. USA, vol. 94, pp. 8521-8526, (1997).
Harada, K., et al., "Identification of two novel arginine binding DNAs", The EMBO Journal, vol. 14, No. 23, pp. 5798-5811, (1995).
Hartig, J.S., et al., "Reporter ribozymes for real-time analysis of domain-specific interactions in biomolecules: HIV-1 reverse transcriptase and the primer-template complex", Angew. Chem. Int. Ed., vol. 41, No. 22, pp. 4263-4266, (2002).
He, X-x., et al., "Bioconjugated nanoparticles for DNA protection from cleavage", J. Am. Chem. Soc., vol. 125, No. 24, pp. 7168-7169, (2003).
Hennrich, G., et al., "Redox switchable fluorescent probe selective for either Hg(II) or Cd(II) and Zn(II)" J. Am. Chem. Soc., vol. 121, No. 21, pp. 5073-5074, (1999).
Hesselberth, J., et al., "In vitro selection of nucleic acids for diagnostic applications", Reviews in Molecular Biotechnology, vol. 74, pp. 15-25, (2000).
Hesselberth, J.R., et al., "Simultaneous detection of diverse analytes with an aptazyme ligase array", Analytical Biochemistry, vol. 312, pp. 106-112, (2003).
Ho, H-A., et al., "Optical sensors based on hybrid aptamer/conjugated polymer complexes", J. Am. Chem. Soc., vol. 126, No. 5, pp. 1384-1387, (2004).
Hock, B., "Antibodies for immunosensors, A review", Analytica Chimica Acta, vol. 347, pp. 177-186, (1997).
Hofmann, H.P., et al., "$Ni^{2+}$-binding RNA motifs with an asymmetric purine-rich internal loop and a G-A base pair", RNA, vol. 3, pp. 1289-1300, (1997).
Holeman, L.A., et al., "Isolation and characterization of fluorophore-binding RNA aptamers", Folding & Design, vol. 3, pp. 423-431, (1998).
Hoogstraten, C.G., et al., "NMR solution structure of the lead-dependent ribozyme: Evidence for dynamics in RNA catalysis", J. Mol. Biol., vol. 284, pp. 337-350, (1998).
Hoogstraten, C.G., et al., "Structural analysis of metal ion ligation to nucleotides and nucleic acids using pulsed EPR spectroscopy", J. Am. Chem. Soc., vol. 124, No. 5, pp. 834-842, (2002).
Huizenga, D.E., et al., "A DNA aptamer that binds adenosine and ATP", Biochemistry, vol. 34, No. 2, pp. 656-665, (1995).
Iler, R.K., "The Chemistry of Silica: Solubility, Polymerization, Colloid and Surface Properties, and Biochemistry, Chapter 6, The surface chemistry of silica", pp. 622-729, A Wiley-Interscience Publication, New York, (1979).
Illangasekare, M., et al., "Small-molecule-substrate interactions with a self-aminoacylating ribozyme", J. Mol. Biol., vol. 268, pp. 631-639, (1997).
Imperiali, B., et al., "Peptide platforms for metal ion sensing", Proc. SPIE-The international society for optical engineering, vol. 3858, pp. 135-143, (1999).

International Search Report dated Jan. 15, 2003 for PCT application No. PCT/US01/20557.

International Search Report dated Aug. 1, 2003 for PCT application No. PCT/US03/08483.

Iqbal, S.S., et al., "A review of molecular recognition technologies for detection of biological threat agents", Biosensors & Bioelectronics, vol. 15, pp. 549-578, (2000).

Abstract of: Iwasaki, K., Mizota, T., Kenkyu Hokoku—Kanagawa-ken Kogyo Shikensho 1991, 62, 57.

Jagner, D., et al., "Determination of lead in microliter amounts of whole blood by stripping potentiometry", Electroanalysis, vol. 6, pp. 285-291, (1994).

Jayasena, S.D., "Aptamers: an emerging class of molecules that rival antibodies in diagnostics", Clinical Chemistry, vol. 45, No. 9, pp. 1628-1650, (1999).

Jenison, R., et al., "Interference-based detection of nucleic acid targets on optically coated silicon", Nature Biotechnology, vol. 19, pp. 62-65, (2001).

Jenison, R.D., et al., "High-resolution molecular discrimination by RNA", Science, vol. 263, pp. 1425-1429, (1994).

Jenne, A., et al., "Rapid Identification and Characterization of Hammerhead-Ribozyme Inhibitors Using Fluorescence-Based Technology", Nature Biotechnology, vol. 19, pp. 56-61, (2001).

Jenne, A., et al., "Real-time Characterization of Ribozymes by Fluorescence Resonance Energy Transfer (FRET)", Angewandte Chemie. International Edition, vol. 38, No. 9, pp. 1300-1303, (1999).

Jhaveri, S., et al., "In vitro selection of signaling aptamers", Nature Biotechnology, vol. 18, pp. 1293-1297, (2000).

Jhaveri, S.D., et al., "Designed signaling aptamers that transduce molecular recognition to changes in fluorescence intensity", J. Am. Chem. Soc., vol. 122, No. 11, pp. 2469-2473, (2000).

Jin, R., et al., "What controls the melting properties of DNA-linked gold nanoparticle assemblies?", J. Am. Chem. Soc., vol. 125, No. 6, pp. 1643-1654, (2003).

Joos, B., et al., "Covalent attachment of hybridizable oligonucleotides to glass supports", Analytical Biochemistry, vol. 247, pp. 96-101, (1997).

Josephson, L., et al., "Magnetic nanosensors for the detection of oligonucleotide sequences", Angewandte Chemie. International Edition, vol. 40, No. 17, pp. 3204-3206, (2001).

Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).

Joyce, G.F., "In vitro evolution of nucleic acids", Current Opinion in Structural Biology, vol. 4, pp. 331-336, (1994).

Katahira, M., et al., "Two metal-binding sites in a lead ribozyme bound to competitively by $Pb^{2+}$ and $Mg^{2+}$: Induced structural changes as revealed by NMR", European Journal of Biochemistry, vol. 255, pp. 727-733, (1998).

Kato, T., et al., "In vitro selection of DNA aptamers which bind to cholic acid", Biochimica et Biophysica Acta, vol. 1493, pp. 12-18, (2000).

Kawakami, J., et al., "In vitro selection of aptamers that act with $zn^{2+}$", Journal of Inorganic Biochemistry, vol. 82, pp. 197-206, (2000).

Khan, R., et al., "Interaction of retroviral nucleocapsid proteins with transfer $RNA^{Phe}$: a lead ribozyme and $^1H$ NMR study", Nucleic Acids Research, vol. 24, No. 18, pp. 3568-3575, (1996).

Khosraviani, M., et al., "Detection of heavy metals by immunoassay: Optimization and validation of a rapid, portable assay for ionic cadmium", Environ. Sci. Technol., vol. 32, No. 1, pp. 137-142, (1998).

Kiga, D., et al., "An RNA aptamer to the xanthine/guanine base with a distinctive mode of purine recognition", Nucleic Acids Research, vol. 26, No. 7, pp. 1755-1760, (1998).

Kim, M.H., et al., "Activation and repression of the activity of a lead ribozyme by the combination of $Pb^{2+}$ and $Mg^{2+\ 1}$", J. Biochem., vol. 122, No. 5, pp. 1062-1067, (1997).

Kluβmann, S., et al., "Mirror-image RNA that binds D-adenosine", Nature Biotechnology, vol. 14, pp. 1112-1115, (1996).

Kohama, T., et al., "Molecular Cloning and Functional Characterization of Murine Sphingosine Kinase", The Journal of Biological Chemistry, vol. 273, No. 37, pp. 23722-23728, (1998).

Koizumi, M., et al., "Allosteric selection of ribozymes that respond to the second messengers cGMP and cAMP", Nature Structural Biology, vol. 6, No. 11, pp. 1062-1071, (1999).

Koizumi, M., et al., "Molecular Recognition of cAMP by an RNA Aptamer", Biochemistry, vol. 39, No. 30, pp. 8983-8992, (2000).

Koizumi, M., et al., "Allosteric ribozymes sensitive to the second messengers cAMP and cGMP", Nucleic Acids Symposium Series, No. 42, pp. 275-276, (1999).

Kruger, K., et al., "Self-splicing RNA: autoexcision and autocyclization of the ribosomal RNA intervening sequence of the Tetrahymena", Cell, vol. 31, pp. 147-157, (1982).

Lato, S.M., et al., "In vitro selection of RNA lectins: Using combinatorial chemistry to interpret ribozyme evolution", Chemistry & Biology, vol. 2, No. 5, pp. 291-303, (1995).

Lauhon, C.T., et al., "RNA aptamers that bind flavin and nicotinamide redox cofactors", J. Am. Chem. Soc., vol. 117, No. 4, pp. 1246-1257, (1995).

Lebruska, L.L., "Selection and Characterization of an RNA Decoy for Transcription Factor NF-kB", Biochemistry, vol. 38, No. 10, pp. 3168-3174, (1999).

Lee, M., et al., "A fiber-optic microarray biosensor using aptamers as receptors", Analytical Biochemistry, vol. 282, pp. 142-146, (2000).

Lee, S-W., et al., "Ordering of quantum dots using genetically engineered viruses", Science, vol. 296, pp. 892-895, (2002).

Legault, P., et al., "Order, dynamics and metal-binding in the lead-dependent ribozyme", J. Mol. Biol., vol. 284, pp. 325-335, (1998).

Lehman, N., et al., "Evolution in vitro of an RNA enzyme with altered metal dependence", Nature, vol. 361, pp. 182-185, (1993).

Lemieux, S., et al., "Modeling active RNA structures using the intersection of conformational space: application to the lead-activated ribozyme", RNA, vol. 4, pp. 739-749, (1998).

Levy, M., et al., "ATP-Dependent Allosteric DNA Enzymes", Chemistry & Biology, vol. 9, pp. 417-426, (2002).

Li, J., et al., "A highly sensitive and selective catalytic DNA biosensor for lead ions", J. Am. Chem. Soc., vol. 122, No. 42, pp. 10466-10467, (2000).

Li, J., et al., "In vitro selection and characterization of a highly efficient Zn(II)-dependent RNA-cleaving deoxyribozyme", Nucleic Acids Research, vol. 28, No. 2, pp. 481-488, (2000).

Li, J.J., et al., "Using molecular beacons as a sensitive fluorescence assay for enzymatic cleavage of single-stranded DNA", Nucleic Acids Research, vol. 28, No. 11, e52, pp. i-vi, (2000).

Li, Y., et al., "A catalytic DNA for porphyrin metallation", Nature Structural Biology, vol. 3, No. 9, pp. 743-747, (1996).

Li, Y., et al., "Capping DNA with DNA", Biochemistry, vol. 19, No. 11, pp. 3106-3114, (2000).

Li, Y., et al., "Deoxyribozymes: new players in the ancient game of biocatalysis", Current Opinion in Structural Biology, vol. 9, pp. 315-323, (1999).

Li, Y., et al., "Phosphorylating DNA with DNA", Proc. Natl. Acad. Sci. USA, vol. 96, pp. 2746-2751, (1999).

Link, S., et al., "Alloy formation of gold-silver nanoparticles and the dependence of the plasmon absorption on their composition", J. Phys. Chem. B, vol. 103, No. 18, pp. 3529-3533, (1999).

Liu, H-W., et al., "Determination of cadmium, mercury and lead in seawater by electrothermal vaporization isotope dilution inductively coupled plasma mass spectrometry", Spectrochimica Acta Part B Atomic Spectroscopy 54, pp. 1367-1375, (1999).

Liu, J., et al., "A colorimetric lead biosensor using DNAzyme-directed assembly of gold nanoparticles", J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection", J. Am. Chem. Soc., vol. 126, No. 39, pp. 12298-12305, (2004).

Liu, J., et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J., et al., "Colorimetric biosensors based on DNAzyme-assembled gold nanoparticles", Journal of Fluorescence, vol. 14, No. 4, pp. 343-354, (2004).

Liu, J., et al., "Highly dispersible molecular sieve carbon nanoparticles", Chem. Mater., vol. 16, No. 22, pp. 4205- 4207, (2004).

Liu, X., et al., "A fiber-optic evanescent wave DNA biosensor based on novel molecular beacons", Analytical Chemistry, vol. 71, No. 22, pp. 5054-5059, (1999).

Liu, Z., et al., "Assemblage of signaling DNA enzymes with intriguing metal-ion specificities and pH dependences", J. Am. Chem. Soc., vol. 125, No. 25, pp. 7539-7545, (2003).

Lohse, P.A., et al., "Ribozyme-catalysed amino-acid transfer reactions", Nature, vol. 381, pp. 442-444, (1996).

Lorsch, J.R., et al., "In vitro evolution of new ribozymes with polynucleotide kinase activity", Nature, vol. 371, pp. 31-36, (1994).

Lorsch, J.R., et al., "In vitro selection of RNA aptamers specific for cyanocobalamin", Biochemistry, vol. 33, No. 4, pp. 973-982, (1994).

Lott, W.B., et al., "A two-metal ion mechanism operates in the hammerhead ribozyme-mediated cleavage of an RNA substrate", Proc. Natl. Acad. Sci. USA, vol. 95, pp. 542-547, (1998).

Lu, Y., "New transition-metal-dependent DNAzymes as efficient endonucleases and as selective metal biosensors", Chem. Eur. J., vol. 8, No. 20, pp. 4588-4596, (2002).

Lu, Y., et al., "New fluorescent and colorimetric DNAzyme biosensors for metal ions", Journal of Inorganic Biochemistry, vol. 96, issue 1, pp. 30, Abstract of the $11^{th}$ International Conference on Biological Inorganic Chemistry; (Jul. 15, 2003).

Majerfeld, I., et al., "An RNA pocket for an aliphatic hydrophobe", Structural Biology, vol. 1, No. 5, pp. 287-292, (1994).

Majerfeld, I., et al., "Isoleucine:RNA sites with associated coding sequences", RNA, vol. 4, pp. 471-478, (1998).

Mannironi, C., et al., "In vitro selection of dopamine RNA ligands", Biochemistry, vol. 36, No. 32, pp. 9726-9734, (1997).

Maoz, R., et al., "Penetration-controlled reactions in organized monolayer assemblies. 1. Aqueous permanganate interaction with monolayer and multilayer films of long-chain surfactants", Langmuir, vol. 3, No. 6, pp. 1034-1044, (1987).

Marcus, A.H., et al., "Estimating the contribution of lead based paint to soil lead, dust lead, and childhood blood lead", American Society for Testing and Materials Spec. STP 1226, pp. 12-23, (1995).

Marsh, T.C., et al., "A new DNA nanostructure, the G-wire, imaged by scanning probe microscopy", Nucleic Acids Research, vol. 23, No. 4, pp. 696-700, (1995).

Matteucci, M.D., et al., "Synthesis of Deoxyoligonucleotides on a polymer support", J. Am. Chem. Soc., vol. 103, No. 11, pp. 3185-3191, (1981).

Mecklenburg, M., et al., "A strategy for the broad range detection of compounds with affinity for nucleic acids", Analytica Chimica Acta, vol. 347, pp. 79-86, (1997).

Mei, S.H.J., et al., "An efficient RNA-cleaving DNA enzyme that synchronizes catalysis with fluorescence signaling", J. Am. Chem. Soc., vol. 125, No. 2, pp. 412-420, (2003).

Meli, M., et al., "Adenine-aptamer complexes: A bipartite RNA site that binds the adenine nucleic base", The Journal of Biological Chemistry, vol. 277, No. 3, pp. 2104-2111, (2002).

Mirkin, C.A., et al., "A DNA-based method for rationally assembling nanoparticles into macroscopic materials", Nature, vol. 382, pp. 607-609, (1996).

Mirkin, S.M., et al., "H-DNA and related structures", Annu. Rev. Biophys. Biomol. Struct., vol. 23, pp. 541-576, (1994).

Miyawaki, A., et al. "Fluorescent indicators for $Ca^{2+}$ based on green fluorescent proteins and calmodulin", Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer", Chem. Commun., pp. 555-557, (1996).

Mullah, B., et al., "Automated synthesis of double dye-labeled oligonucleotides using tetramethylrhodamine (TAMRA) solid supports", Tetrahedron Letters, vol. 38, No. 33, pp. 5751-5754, (1997).

Nazarenko, I.A., et al., "A closed tube format for amplification and detection of DNA based on energy transfer", Nucleic Acids Research, vol. 26, No. 12, pp. 2516-2521, (1997).

Nazarenko, I.A., et al., "Defining a Smaller RNA Substrate for Elongation Factor Tu", Biochemistry, vol. 34, No. 8, pp. 2545-2552, (1995).

Niemeyer, C.M., "Nanoparticles, proteins, and nucleic acids: Biotechnology meets materials science", Angew. Chem. Int. Edition, vol. 40, pp. 4128-4158, (2001).

Nieuwlandt, D., et al., "In Vitro Selection of RNA Ligands to Substance P", Biochemistry, vol. 34, No. 16, pp. 5651-5659, (1995).

Nissen, P., et al., "The structural basis of ribosome activity in peptide bond synthesis", Science, vol. 289, pp. 920-930, (2000).

Nolte, A., et al., "Mirror-design of L-oligonucleotide ligands binding to L-arginine", Nature Biotechnology, vol. 14, pp. 1116-1119, (1996).

Nutiu, R., et al., "Structure-switching signaling aptamers", J. Am. Chem. Soc., vol. 125, No. 16, pp. 4771-4778, (2003).

Nuzzo, R.G., et al., "Spontaneously organized molecular assemblies. 3. Preparation and properties of solution adsorbed monolayers of organic disulfides on gold surfaces", J. Am. Chem. Soc., vol. 109, No. 8, pp. 2358-2368, (1987).

O'Donnell, M.J., et al., "High-Density, Covalent Attachment of DNA to Silicon Wafers for Analysis by MALDI-TOF Mass Spectrometry", Analytical Chemistry, vol. 69, No. 13, pp. 2438-2443, (1997).

Oehme, I., et al., "Optical sensors for determination of heavy metal ions", Mikrochim. Acta, vol. 126, pp. 177-192, (1997).

Ohmichi, T., et al., "Role of $Nd^{3+}$ and $Pb^{2+}$ on the RNA cleavage reaction by a small ribozyme", Biochemistry, vol. 36, No. 12, pp. 3514-3521, (1997).

Ohmichi, T., et al., "Effect of substrate RNA sequence on the cleavage reaction by a short ribozyme", Nucleic Acids Research, vol. 26, No. 24, pp. 5655-5661, (1998).

Okazawa, A., et al., "In vitro selection of hematoporphyrin binding DNA aptamers", Bioorganic & Medicinal Chemistry, Letters 10, pp. 2653-2656, (2000).

Ota, N., et al., "Effects of helical structures formed by the binding arms of DNAzymes and their substrates on catalytic activity", Nucleic Acids Research, vol. 26, No. 14, pp. 3385-3391, (1998).

Pan, T., et al., "A small metalloribozyme with a two-step mechanism", Nature, vol. 358, pp. 560-563, (1992).

Pan, T., et al., "In vitro selection of RNAs that undergo cleavage with $Pb^{2+}$" Biochemistry, vol. 31, No. 16, pp. 3887-3895, (1992).

Pan, T., et al., "Properties of an in vitro selected $Pb^{2+}$ cleavage motif", Biochemistry, vol. 33, No. 32, pp. 9561-9565, (1994).

Pan, W., et al., "Isolation of virus-neutralizing RNAs from a large pool of random sequences", Proc. Natl. Acad. Sci. USA, vol. 92, pp. 11509-11513, (1995).

Park, S-J., et al., "Array-based electrical detection of DNA with nanoparticle probes", Science, vol. 295, pp. 1503-1506, (2002).

Parsons, P.J., et al., "A rapid Zeeman graphite furnace atomic absorption spectrometric method for the determination of lead in blood", Spectrochimica Acta, vol. 48B, No. 6/7, pp. 925-939, (1993).

Pavlov, A.R., et al., "Determination of lead in environmental water samples by a rapid and portable immunoassay", ANYL, Book of Abstracts, 219th ACS National Meeting, San Francisco, CA, Mar. 26-30, 2000.

Pavlov, V., et al., "Aptamer-functionalized Au nanoparticles for the amplified optical detection of thrombin", J. Am. Chem. Soc., vol. 126, No. 38, pp. 11768-11769, (2004).

Pearce, D.A., et al., "Peptidyl chemosensors incorporating a FRET mechanism for detection of Ni(II)", Bioorganic & Medicinal Chemistry, Letters 8, pp. 1963-1968, (1998).

Pease, A.C., et al., "Light-generated oligonucleotide arrays for rapid DNA sequence analysis", Proc. Natl. Acad. Sci. USA, vol. 91, pp. 5022-5026, (1994).

Piccirilli, J.A., et al., "Aminoacyl esterase activity of the tetrahymena ribozyme", Science, New Series, vol. 256, issue 5062, pp. 1420-1424, (1992).

Pley, H.W., et al., "Three-dimensional structure of a hammerhead ribozyme", Nature, vol. 372, pp. 68-74, (1994).

Potyrailo, R.A., et al., "Adapting selected nucleic acid ligands (aptamers) to biosensors", Analytical Chemistry, vol. 70, No. 16, pp. 3419-3425, (1998).

Prudent, J.R., et al., "Expanding the scope of Rna catalysis", Science, New Series, vol. 264, issue 5167, pp. 1924-1927, (1994).

Qiao, H., et al., "Transferability of blood lead determinations by furnace atomic absorption spectrophotometry and continuum background correction", Clinical Chemistry, vol. 41, No. 10, pp. 1451-1454, (1995).

Rabinowitz, M., et al., "Home refinishing, lead paint, and infant blood lead levels", American Journal of Public Health, vol. 75, No. 4, pp. 403-404, (1985).

Rajendran, M., et al., "Selecting nucleic acids for biosensor applications", Combinatorial Chemistry and High Throughput Screening, vol. 5, No. 4, pp. 263-270, (2002).

Rakow, N. A., et al., "A colorimetric sensor array for odour visualization", Nature, vol. 406, pp. 710-713, (2000).

Rink, S.M., et al., "Creation of RNA molecules that recognize the oxidative lesion 7,8-dihydro-8-hydroxy-2'-deoxyguanosine (8-oxodG) in DNA", Proc. Natl. Acad. Sci. USA, vol. 95, pp. 11619-11624, (1998).

Robertson, M.P., et al., "Design and optimization of effector-activated ribozyme ligases", Nucleic Acids Research, vol. 28, No. 8, pp. 1751-1759, (2000).

Robertson, M.P., et al., "In vitro selection of an allosteric ribozyme that transduces analytes to amplicons", Nature Biotechnology, vol. 17, pp. 62-66, (1999).

Roth, A., et al., "An amino acid as a cofactor for a catalytic polynucleotide", Proc. Natl. Acad. Sci. USA, vol. 95, pp. 6027-6031, (1998).

Roychowdhury-Saha, M., et al., "Flavin Recognition by an RNA Aptamer Targeted toward FAD", Biochemistry, vol. 41, No. 8, pp. 2492-2499, (2002).

Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain", The Journal of Biological Chemistry, vol. 273, No. 32, pp. 20556-20567, (1998).

Rurack, K., et al., "A selective and sensitive fluoroionophore for $Hg^{II}$, $Ag^{I}$, and $Cu^{II}$ with virtually decoupled fluorophore and receptor units", J. Am. Chem. Soc., vol. 122, No. 5, pp. 968-969, (2000).

Rusconi, C.P., et al., "RNA aptamers as reversible antagonists of coagulation factor IXa", Nature, vol. 419, pp. 90-94, (2002).

Sabanayagam, C.R., et al., "Oligonucleotide immobilization on micropatterened streptavidin surfaces", Nucleic Acids Research, vol. 28, No. 8, e33, pp. i-iv, (2000).

Santoro, S.W. et al., "Mechanism and utility of an RNA-cleaving DNA enzyme", Biochemistry, vol. 37, No. 38, pp. 13330-13342, (1998).

Santoro, S.W., et al., "A general purpose RNA-cleaving DNA enzyme", Proc. Natl. Acad. Sci. USA, vol. 94, pp. 4262-4266, (1997).

Santoro, S.W., et al., "RNA Cleavage by a DNA Enzyme with Extended Chemical Functionality", J. Am. Chem. Soc., vol. 122, No. 11, pp. 2433-2439, (2000).

Sassanfar, M., et al., "An RNA motif that binds ATP", Nature, vol. 364, pp. 550-553, (1993).

Schwartz, J., et al., "The risk of lead toxicity in homes with lead paint hazard", Environmental Research, vol. 54, No. 1, pp. 1-7, (1991).

Scott, W.G., et al., "The crystal structure of an all-RNA hammerhead ribozyme: A proposed mechanism for RNA catalytic cleavage", Cell, vol. 81, pp. 991-1002, (1995).

Scott, W.G., "RNA catalysis", Current Opinion in Structural Biology, vol. 8, pp. 720-726, (1998).

Search results of key word search of medline, Mar. 26, 2000.

Search results of key word search on Chemical Abstracts, Mar. 24, 2000.

Search results of key word search from various databases, Mar. 24, 2000.

Seeman, N.C., et al., "Synthetic DNA knots and catenanes", New Journal of Chemistry, vol. 17, pp. 739-755, (1993).

Seeman, N.C., et al., "Emulating biology: Building nanostructures from the bottom up", Proc. Natl. Acad. Sci., vol. 99, suppl. 2, pp. 6451-6455, (2002).

Seeman, N.C., "DNA in a material world", Nature, vol. 421, pp. 427-431, (2003).

Seetharaman, S., et al., "Immobilized RNA switches for the analysis of complex chemical and biological mixtures", Nature Biotechnology, vol. 19, pp. 336-341, (2001).

Sen, D., et al., "DNA enzymes", Current Opinion in Chemical Biology, vol. 2, pp. 680-687, (1998).

Shaiu, W-L., et al., "Atomic force microscopy of oriented linear DNA molecules labeled with 5nm gold spheres", Nucleic Acids Research, vol. 21, No. 1, pp. 99-103, (1993).

Shaw, S.Y., et al., "Knotting of a DNA chain during ring closure", Science, New Series, vol. 260, issue 5107, pp. 533-536, (1993).

Shekhtman, E.M., et al., "Stereostructure of replicative DNA catenanes from eukaryotic cells", New Journal of Chemistry, vol. 17, pp. 757-763, (1993).

Sigurdsson, S.T., et al., "Small ribozymes", RNA Structure and Function, Cold Spring Harbor Laboratory Press (Monograph 35), pp. 339-375, (1998).

Singh, K.K., et al., "Fluorescence Polarization for Monitoring Ribozyme Reactions in Real-Time", Biotechniques, vol. 29, No. 2, pp. 344-351, (2000).

Smith, F.W., et al., "Quadruplex structure of oxytricha telomeric DNA oligonucleotides", Nature, vol. 356, pp. 164-168, (1992).

Smith, J.O., et al., "Molecular recognition of PNA-containing hybrids: Spontaneous assembly of helical cyanine dye aggregates on PNA templates", J. Am. Chem. Soc., vol. 121, No. 12, pp. 2686-2695, (1999).

Soriaga, M.P., et al., "Determination of the orientation of aromatic molecules adsorbed on platinum electrodes: The effect of solute concentration", J. Am. Chem. Soc., vol. 104, No. 14, pp. 3937-3945, (1982).

Soukup, G.A., et al., "Engineering precision RNA molecular switches", Proc. Natl. Acad. Sci. USA, vol. 96, pp. 3584-3589, (1999).

Soukup, G.A., et al., "Allosteric nucleic acid catalysts", Current Opinion in Structural Biology, vol. 10, pp. 318-325, (2000).

Srisawat, C., et al., "Sephadex-binding RNA ligands: rapid affinity purification of RNA from complex RNA mixtures", Nucleic Acids Research, vol. 29, No. 2 e4, pp. 1-5, (2001).

Stage-Zimmermann, T.K., et al., "Hammerhead ribozyme kinetics", RNA, vol. 4, pp. 875-889, (1998).

Stojanovic, M.N., et al., "Aptamer-based colorimetric probe for cocaine", J. Am. Chem. Soc., vol. 124, No. 33, pp. 9678-9679, (2002).

Stojanovic, M.N., et al., "Aptamer-based folding fluorescent sensor for cocaine", Journal of the American Chemical Society, vol. 123, No. 21, pp. 4928-4931, (2001).

Stojanovic, M.N., et al., "Fluorescent sensors based on aptamer self-assembly", Journal of the American Chemical Society, vol. 122, No. 46, pp. 11547-11548, (2000).

Storhoff, J.J., et al., "Programmed materials synthesis with DNA", Chem. Rev., vol. 99, No. 7, pp. 1849-1862, (1999).

Storhoff, J.J., et al., "Facile colorimetric detection of polynucleotides based on gold nanoparticle probes", Proceedings of the 1998 ERDEC Scientific Conference on Chemical and Biological Defense Research, Nov. 17-20, 1998, Aberdeen Proving Ground, pp. 221-226, (1999).

Storhoff, J.J., et al., "What Controls the Optical Properties of DNA-Linked Gold Nanoparticle Assemblies?", J. Am. Chem. Soc., vol. 122, No. 19, pp. 4640-4650, (2000).

Storhoff, J.J., et al., "One-pot colorimetric differentiation of polynucleotides with single base imperfections using gold nanoparticle probes", Journal of the American Chemical Society, vol. 120, No. 9, pp. 1959-1964, (1998).

Streicher, B., et al., "Lead cleavage site in the core structure of group I intron-RNA", Nucleic Acids Research, vol. 21, No. 2, pp. 311-317, (1993).

Sugimoto, N., et al., "Site-specific cleavage reaction catalyzed by leadzyme is enhanced by combined effect of lead and rare earth ions", FEBS Letters, vol. 393, pp. 97-100, (1996).

Sun, L.Q., et al., "Catalytic nucleic acids: From lab to applications", Pharmacological Reviews, vol. 52, pp. 325-347, (2000).

Tahan, J.E., et al., "Electrothermal atomic absorption spectrometric determination of Al, Cu, Ge, Pb, V and Zn in clinical samples and in certified environmental reference materials", Analytica Chimica Acta, vol. 295, pp, 187-197, (1994).

Takagi, Y., et al., "Survey and Summary: Recent advances in the elucidation of the mechanisms of action of ribozymes", Nucleic Acids Research, vol. 29, No. 9, pp. 1815-1834, (2001).

Tang, J., et al., "Rational design of allosteric ribozymes", Chemistry & Biology, vol. 4, No. 6, pp. 453-459, (1997).

Tang, J., et al., "Structural diversity of self-cleaving ribozymes", Proc. Natl. Acad. Sci. USA, vol. 97, No. 11, pp. 5784-5789, (2000).

Tanner, N.K., "Biochemistry of hepatitis delta virus catalytic RNAs", Ribozymes in the Gene Therapy of Cancer, Chapter 3, pp. 23-38, (1998).

Tao, J., et al., "Arginine-Binding RNAs Resembling TAR Identified by in Vitro Selection",Biochemistry, vol. 35, No. 7, pp. 2229-2238, (1996).

Tarasow, T.M., et al., "RNA-catalysed carbon-carbon bond formation", Nature, vol. 389, pp. 54-57, (1997).

Telting-Diaz, M., et al., "Mass-produced ionophore-based fluorescent microspheres for trace level determination of lead ions", Analytical Chemistry, vol. 74, No. 20, pp. 5251-5256, (2002).

Thompson, R.B., et al., "Determination of Picomolar Concentrations of Metal Ions Using Fluorescence Anisotropy: Biosensing with a "Reagentless" Enzyme Transducer", Analytical Chemistry, vol. 70, No. 22, pp. 4717-4723, (1998).

Timmons, C.O., et al., "Investigation of Fatty Acid Monolayers on Metals by Contact Potential Measurements", Journal of Physical Chemistry, vol. 69, No. 3, pp. 984-990, (1965).

Tompkins, H.G., et al., "The study of the gas-solid interaction of acetic acid with a cuprous oxide surface using reflection-absorption spectroscopy", Journal of Colloid and Interface Science, vol. 49, No. 3, pp. 410-421, (1974).

Travascio, P., et al., "A ribozyme and a catalytic DNA with peroxidase activity: active sites versus cofactor-binding sites", Chemistry & Biology, vol. 6, No. 11, pp. 779-787, (1999).

Tsang, J., et al., "In vitro evolution of randomized ribozymes", Methods in Enzymology, vol. 267, pp. 410-426, (1996).

Tsien, R.Y., "Fluorescent and photochemical probes of dynamic biochemical signals inside living cells", Fluorescent Chemosensors for Ion and Molecule Recognition, (ed. Czarnik, A.W.), chapter 9, pp. 130-146, American Chemical Society, (1993).

Tuerk, C., et al., "RNA pseudoknots that inhibit human immunodeficiency virus type 1 reverse transcriptase", Proc. Natl. Acad. Sci. USA, vol. 89, pp. 6988-6992, (1992).

Tuerk, C., et al., "Systematic evolution of ligands by exponential enrichment: RNA ligands to bacteriophage T4 DNA polymerase", Science, New Series, vol. 249, issue 4968, pp. 505-510, (1990).

Tyagi, S., et al., "Molecular Beacons: Probes that fluoresce upon hybridization", Nature Biotechnology, vol. 14, pp. 303-308, (1996).

Tyagi, S., et al., "Multicolor molecular beacons for allele discrimination", Nature Biotechnology, vol. 16, pp. 49-53, (1998).

Tyagi, S., et al., "Wavelength-shifting molecular beacons", Nature Biotechnology, vol. 18, pp. 1191-1196, (2000).

Ueyama, H., "A novel potassium sensing in aqueous media with a synthetic oligonucleotide derivative. Fluorescence resonance energy transfer associated with guanine quartet-potassium ion complex formation", J. Am. Chem. Soc., vol. 124, No. 48, pp. 14286-14287, (2002).

Uphoff, K.W., et al., "In vitro selection of aptamers: the dearth of pure reason", Current Opinion in Structural Biology, vol. 6, pp. 281-288, (1996).

Vaish, N.K., et al., "In vitro selection of a purine nucleotide-specific hammerhead-like ribozyme", Proc. Natl. Acad. Sci. USA, vol. 95, pp. 2158-2162, (1998).

Valadkhan, S., et al., "Splicing-related catalysis by protein-free snRNAs", Nature, vol. 413, pp. 701-707, (2001).

Vianini, E., et al., "In vitro selection of DNA aptamers that bind L-tyrosinamide", Bioorganic & Medicinal Chemistry, vol. 9, pp. 2543-2548, (2001).

Walkup, G.K., et al., "Design and Evaluation of a Peptidyl Fluorescent Chemosensor for Divalent Zinc", J. Am. Chem. Soc., vol. 118, No. 12, pp. 3053-3054, (1996).

Wallace, S.T., et al., In vitro selection and characterization of streptomycin-binding RNAs: recognition discrimination between antibiotics, RNA, vol. 4, pp. 112-123, (1998).

Wallis, M.G., et al., "A novel RNA motif for neomycin recognition", Chemistry & Biology, vol. 2, No. 8, pp. 543-552, (1995).

Wallis, M.G., et al., "In vitro selection of a viomycin-binding RNA pseudoknot", Chemistry & Biology, vol. 4, No. 5, pp. 357-366, (1997).

Walter, F., et al., "Folding of the four-way RNA junction of the hairpin ribozyme", Biochemistry, vol. 37, No. 50, pp. 17629-17636, (1998).

Walter, N.G., et al., "The hairpin ribozyme: structure, assembly and catalysis", Current Opinion in Chemical Biology, vol. 2, pp. 24-30, (1998).

Wang, D.Y., et al., "A general strategy for effector-mediated control of RNA-cleaving ribozymes and DNA enzymes", J. Mol. Biol., vol. 318, pp. 33-43, (2002).

Wang, F., et al., "Sphingosine-1-phosphate Inhibits Motility of Human Breast Cancer Cells Independently of Cell Surface Receptors", Cancer Research, vol. 59, pp. 6185-6191, (1999).

Wang, J., "Survey and Summary: From DNA biosensors to gene chips", Nucleic Acids Research, vol. 28, No. 16, pp. 3011-3016, (2000).

Wang, K.Y., et al., "A DNA aptamer which binds to and inhibits thrombin exhibits a new structural motif for DNA", Biochemistry, vol. 32, No. 8, pp. 1899-1904, (1993).

Wang, Y., et al., "Assembly and characterization of five-arm and six-arm DNA branched junctions", Biochemistry, vol. 30, pp. 5667-5674, (1991).

Wang, Y., et al., "RNA molecules that specifically and stoichiometrically bind aminoglycoside antibiotics with high affinities", Biochemistry, vol. 35, No. 38, pp. 12338-12346, (1996).

Wecker, M., et al., "In vitro selection of a novel catalytic RNA: characterization of a sulfur alkylation reaction and interaction with a small peptide", RNA, vol. 2, pp. 982-994, (1996).

Wedekind, J.E., et al., "Crystal structure of a lead-dependent ribozyme revealing metal binding sites relevant to catalysis", Nature Structural Biology, vol. 6, No. 3, pp. 261-268, (1999).

Wedekind, J.E., et al., "Crystal structure of the leadzyme at 1.8 Å Resolution: Metal ion binding and the implications for catalytic mechanism and alto site ion regulation", Biochemistry, vol. 42, No. 32, pp. 9554-9563, (2003).

Wells, R.D., "Unusual DNA structures", Journal of Biological Chemistry, vol. 263, No. 3, pp. 1095-1098, (1988).

Werstuck, G., et al., "Controlling gene expression in living cells through small molecule-RNA interactions", Science, vol. 282, pp. 296-298, (1998).

Whaley, S.R., et al., "Selection of peptides with semiconductor binding specificity for directed nanocrystal assembly", Nature, vol. 405, pp. 665-668, (2000).

Whitesides, G.M., et al., "Self-assembled monolayers and lithography", Proceedings of the Robert A. Welch Foundation 39th Conference on Chemical Research on Nanophase Chemistry, pp. 109-121, Houston, TX, Oct. 23-24, 1995.

Wiegand, T.W., et al., "High-affinity oligonucleotide ligands to human IgE inhibit binding to Fc epsilon receptor I", The Journal of Immunology, vol. 157, pp. 221-230, (1996).

Wiegand, T.W., et al., "Selection of RNA amide synthases", Chemistry & Biology, vol. 4, No. 9, pp. 675-683, (1997).

Williams, K.P., et al., "Bioactive and nuclease-resistant L-DNA ligand of vasopressin", Proc. Natl. Acad. Sci. USA, vol. 94, pp. 11285-11290, (1997).

Williams, K.P., et al., "Selection of novel $Mg^{2+}$-dependent self-cleaving ribozymes" The EMBO Journal, vol. 14, No. 18, pp. 4551-4557, (1995).

Wilson, C., et al., "Functional requirements for specific ligand recognition by a biotin-binding RNA Pseudoknot", Biochemistry, vol. 37, No. 41, pp. 14410-14419, (1998).

Wilson, C., et al., "In vitro evolution of a self-alkylating ribozyme", Nature, vol. 374, pp. 777-782, (1995).

Wilson, C., et al., "Isolation of a fluorophore-specific DNA aptamer with weak redox activity", Chemistry & Biology, vol. 5, No. 11, pp. 609-617, (1998).

Wilson, D.S., et al., "In vitro selection of functional nucleic acids", Annu. Rev. Biochem. vol. 68, pp. 611-647, (1999).

Winkler, J.D., et al., "Photodynamic Fluorescent Metal Ion Sensors with Parts per Billion Sensitivity", J. Am. Chem. Soc., vol. 120, No. 13, pp. 3237-3242, (1998).

Wittmann, C., et al.,"Microbial and Enzyme sensors for environmental monitoring", Handbook of Biosensors and Electronic Noses: Medicine, Food, and the Environment, pp. 299-332, (1997).

Xia, P., et al., "Activation of Sphingosine Kinase by Tumor Necrosis Factor-α Inhibits Apoptosis in Human Endothelial Cells", Journal of Biological Chemistry, vol. 274, No. 48, pp. 34499-34505, (1999).

Yan, H., et al., "DNA-Templated self-assembly of protein arrays and highly conductive nanowires", Science, vol. 301, pp. 1882-1884, (2003).

Yang, Q., et al., "DNA ligands that bind tightly and selectively to cellobiose", Proc. Natl. Acad. Sci. USA, vol. 95, pp. 5462-5467, (1998).

English Translation of Yang, Y., et al., "Measurement of lead and magnesium in distilled spirits using inductively coupled plasma optical emission spectrometry viewed from the end", Analytical Chemistry (Fenxi Huaxue), Chinese Journal of Analytical Chemistry, vol. 25, No. 9, pp. 1114-1117, (1997).

Yurke, B., et al., "A DNA-fuelled molecular machine made of DNA", Nature, vol. 406, pp. 605-608, (2000).

Zhang, B., et al., "Peptide bond formation by in vitro selected ribozymes", Nature, vol. 390, pp. 96-100, (1997).

Zhang, P., et al., "Design of a molecular beacon DNA probe with two fluorophores", Angewandte Chemie International Edition, vol. 40, No. 2, pp. 402-405, (2001).

Zillmann, M., et al., "In vitro optimization of truncated stem-loop II variants of the hammerhead ribozyme for cleavage in low concentrations of magnesium under non-turnover conditions", RNA, vol. 3, pp. 734-747, (1997).

Zimmerman, J.M., et al., "In vivo selection of spectinomycin-binding RNAs", Nucleic Acids Research, vol. 30, No. 24, pp. 5425-5435, (2002).

Zimmermann, G.R., et al., "Molecular interactions and metal binding in the theophylline-binding core of an RNA aptamer", RNA, vol. 6, pp. 659-667, (2000).

International Search Report dated Nov. 21, 2005 for PCT application No. PCT/US2005/001060.

Supplemental International Search Report dated Jan. 10, 2006 for PCT application No. PCT/US2005/001060.

Liu, J., et al., "Size control, metal substitution, and catalytic application of cryptomelane nanomaterials prepared using cross-linking reagents", Chem. Mater., vol. 16, No. 2, pp. 276-285, (2004).

Cake, K.M., et al., "Partition of circulating lead between serum and red cells is different for internal and external sources of lead", American Journal of Industrial Medicine, vol. 29, pp. 440-445, (1996).

International Search Report dated Aug. 31, 2004 for PCT application No. PCT/US2004/002946.

Hazarika, P., et al., "Reversible switching of DNA-Gold nanoparticle aggregation", Angewandte Chemie International Edition, vol. 43, No. 47, pp. 6469-6471, (2004).

International Search Report dated May 29, 2006 for PCT application No. PCT/US2005/037896.

Liu, J., et al., "Improving fluorescent DNAzyme biosensors by combining Inter- and Intramolecular quenchers", Analytical Chemistry, vol. 75, No. 23, pp. 6666-6672, (2003).

Liu, J., et al., "Stimuli-responsive disassembly of nanoparticle aggregates for light-up colorimetric sensing", Journal of the American Chemical Society, vol. 127, No. 36, pp. 12677-12683, (2005).

European Search Report dated Jul. 10, 2006 for PCT application No. PCT/US2003/12576.

Tanner, F.C., et al., "Transfection of human endothelial cells", Cardiovascular research, vol. 35, pp. 522-528, (1997).

International Search Report dated Nov. 17, 2006 for PCT application No. PCT/US2006/001627.

Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).

Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).

Levy, M., et al., "Exponential growth by cross-catalytic cleavage of deoxyribozymogens",PNAS, vol. 100, No. 11, pp. 6416-6421, (2003).

Beyer, S., et al., "A modular DNA signal translator for the controlled release of a protein by an aptamer", Nucleic Acids Research, vol. 34, No. 5, pp. 1581-1587, (2006).

Frauendorf, C., et al., "Detection of small organic analytes by fluorescing molecular switches", Bioorganic & Medicinal Chemistry, vol. 9, pp. 2521-2524, (2001).

Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).

Liu, J., et al., "Optimization of a $Pb^{2+}$-directed gold nanoparticle/DNAzyme assembly and its application as a colorimetric biosensor for $Pb^{2+}$", Chem. Mater., vol. 16, No. 17, pp. 3231-3238, (2004).

Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).

Product Description: Pall Corporation, "Immunochromatographic, lateral flow or strip tests development ideas", found at: http://www.pall.com/34445_4154.asp, 7 pages, (1998).

Liu, J., et al., "Fast colorimetric sensing of adenosine and cocaine based on a general sensor design involving aptamers and nanoparticles", Angew. Chem. Int. Ed., vol. 45, pp. 90-94, (2006).

Liu, J., et al., "A simple and sensitive "dipstick" test in serum based on lateral flow separation of aptamer-linked nanostructures", Angewandte Chemie International Edition, vol. 45, pp. 7955-7959, (2006).

Jiang, P. et al., "Fluorescent detection of zinc in biological systems: recent development on the design of chemosensors and biosensors", Coordination Chemistry Reviews, vol. 248, pp. 205-229, (2004).

Lim, M.H. et al., "Metal-based turn-on fluorescent probes for sensing nitric oxide", Accounts of Chemical Research, vol. 40, No. 1, pp. 41-51, (2007).

Yoon, S. et al., "Screening mercury levels in fish with a selective fluorescent chemosensor", Journal of the American Chemical Society, vol. 127, pp. 16030-16031, (2005).

Yang, L. et al., "Imaging of the intracellular topography of copper with a fluorescent sensor and by synchrotron x-ray fluorescence microscopy", Proceedings of the National Academy of Science, vol. 102, No. 32, pp. 11179-11184, (2005).

He, Q. et al., "A selective fluorescent sensor for detecting lead in living cells", Journal of the American Chemical Society, vol. 128, pp. 9316-9317, (2006).

Zeng, L. et al., "A selective turn-on fluorescent sensor for imaging copper in living cells", Journal of the American Chemical Society, vol. 128, pp. 10-11, (2006).

Wegner, S.V. et al., "Design of an emission ratiometric biosensor from MerR family proteins: A sensitive and selective sensor for $Hg^{2+}$", Journal of the American Chemical Society, vol. 129, pp. 3474-3475, (2007).

Nolan, E.M. et al., "Turn-on and ratiometric mercury sensing in water with a red-emitting probe", Journal of the American Chemical Society, vol. 129, pp. 5910-5918, (2007).

Sasaki, D.Y. et al., "Metal-induced dispersion of lipid aggregates: A simple, selective, and sensitive fluorescent metal ion sensor", Angew. Chem. Int. Ed. England, vol. 34, No. 8, pp. 905-907, (1995).

Torrado, A. et al., "Exploiting polypeptide motifs for the design of selective Cu(II) ion chemosensors" Journal of the American Chemical Society, vol. 120, pp. 609-610, (1998).

Grandini, P. et al., "Exploiting the self-assembly strategy for the design of selective $Cu^{II}$ ion chemosensors", Angew. Chem. Int. Ed, vol. 38, No. 20, pp. 3061-3064, (1999).

Klein, G. et al., "A fluorescent metal sensor based on macrocyclic chelation", Chem. Comm., pp. 561-562, (2001).

Zheng, Y. et al., "A new fluorescent chemosensor for copper ions based on tripeptide glycyl-histidyl-lysine (GHK)", Organic Letters, vol. 3, No. 21, pp. 3277-3280, (2001).

Boiocchi, M. et al., "A two-channel molecular dosimeter for the optical detection of copper(II)" Chem. Comm, pp. 1812-1813, (2003).

Zheng, Y. et al., "Peptidyl fluorescent chemosensors for the detection of divalent copper", Analytical Chemistry, vol. 75, No. 7, pp. 1706-1712, (2003).

Zheng, Y. et al., "Development of fluorescent film sensors for the detection of divalent copper", Journal of the American Chemical Society, vol. 125, pp. 2680-2686, (2003).

Roy, B.C. et al., "Synthesis of new, pyrene-containing metal-chelating lipids and sensing of cupric ions", Organic Letters, vol. 5, No. 1, pp. 11-14, (2003).

Kaur, S. et al., "Photoactive chemosensors 4: a $Cu^{2+}$ protein cavity mimicking fluorescent chemosensor for selective $Cu^{2+}$ recognition", Tetrahedron Letters, vol. 45, pp. 5081-5085, (2004).

Mei, Y. et al., "A selective and sensitive chemosensor for $Cu^{2+}$ based on 8-hydroxyquinoline", Tetrahedron Letters, vol. 47, pp. 2447-2449, (2006).

Zhang, X-B. et al., "A highly selective fluorescent sensor for $Cu^{2+}$ based on 2-(2'-hydroxyphenyl)benzoxazole in a poly(vinyl chloride) matrix", Analytica Chimica Acta, vol. 567, pp. 189-195, (2006).

Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).

Kim, S. H. et al., "$Hg^{2+}$-selective off-on and Cu$^{II}$selective on-off type fluoroionophore based upon cyclam", Organic Letters, vol. 8, No. 3, pp. 371-374, (2006).

White, B. R. et al., "Fluorescent peptide sensor for the selective detection of $Cu^{2+}$", Talanta, vol. 71, pp. 2015-2020, (2007).

Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).

Dujols, V. et al., "A long-wavelength fluorescent chemodosimeter selective for Cu(II) ion in water", Journal of the American Chemical Society, vol. 119, pp. 7386-7387, (1997).

Yang, J-S. et al., "$Cu^{2+}$-induced blue shift of the pyrene excimer emission: a new signal transduction mode of pyrene probes", Organic Letters, vol. 3, No. 6, pp. 889-892, (2001).

Kaur, S. et al., "Photoactive chemosensors 3: a unique case of fluorescence enhancement with Cu(II)", Chem. Comm., pp. 2840-2841, (2002).

Wu, Q. et al., "Catalytic signal amplification using a heck reaction. An example in the fluorescence sensing of Cu(II)", Journal of the American Chemical Society, vol. 126, pp. 14682-14683, (2004).

Royzen, M. et al., "Ratiometric displacement approach to Cu(II) sensing by fluorescence", Journal of the American Chemical Society, vol. 127, pp. 1612-1613, (2005).

Xu, Z. et al., "Ratiometric and selective fluorescent sensor for $Cu^{II}$ based on internal charge transfer (ICT)", Organic Letters, vol. 7, No. 5, pp. 889-892, (2005).

Wen, Z-C. et al., "A highly selective charge transfer fluoroionophore for $Cu^{2+}$", Chem. Commun., pp. 106-108, (2006).

Yang, H. et al., "Highly selective ratiometric fluorescent sensor for Cu(II) with two urea groups", Tetrahedron Letters, vol. 47, pp. 2911-2914, (2006).

Martinez, R. et al., "2-aza-1,3-butadiene derivatives featuring an anthracene or pyrene unit: highly selective colorimetric and fluorescent signaling of $Cu^{2+}$ cation", Organic Letters, vol. 8, No. 15, pp. 3235-3238, (2006).

Navani, N.K. et al., "Nucleic acid aptamers and enzymes as sensors", Current Opinion in Chemical Biology, vol. 10, pp. 272-281, (2006).

Liu, J. et al., "A catalytic beacon sensor for uranium with parts-per-trillion sensitivity and millionfold selectivity", Proceedings of the National Academy of Science, vol. 104, No. 7, pp. 2056-2061, (2007).

Georgopoulos, P.G. et al., "Environmental copper: its dynamics and human exposure issues", Journal of Toxicology and Environmental Health, Part B, vol. 4, pp. 341-394, (2001).

Hertzberg, R.P. et al., "Cleavage of DNA with methidiumpropyl-EDTA-iron(II): reaction conditions and product analyses", Biochemistry, vol. 23, pp. 3934-3945, (1984).

Yazzie, M. et al., "Uranyl acetate causes DNA single strand breaks in vitro in the presence of ascorbate (Vitamin C)", Chem. Res. Toxicol., vol. 16, pp. 524-530, (2003).

Bolletta, F. et al., "A [$Ru^{II}$ (bipy)$_3$]-[1,9-diamino-3,7-diazanonane-4,6-dione] two-component system as an efficient on-off luminescent chemosensor for $Ni^{2+}$ and $Cu^{2+}$ in water, based on an ET (energy transfer) mechanism", Journal of the Chemical Society, Dalton Transactions, pp. 1381-1385, (1999).

Carmi, N. et al., "Characterization of a DNA-cleaving deoxyribozyme", Bioorganic & Medicinal Chemistry, vol. 9, issue 10, pp. 2589-2600, (2001).

Liu, J. et al., "A DNAzyme catalytic beacon sensor for paramagnetic $Cu^{2+}$ ions in aqueous solution with high sensitivity and selectivity", Journal of the American Chemical Society, vol. 129, No. 32, pp. 9838-9839, (2007), ASAP Web Release Date: Jul. 24, 2007.

Tanaka, K. et al., "Programmable self-assembly of metal ions inside artificial DNA duplexes", Nature Nanotechnology, vol. 1, pp. 190-194, (2006).

Achenbach, J.C. et al., "DNAzymes: From creation in vitro to application in vivo", Current Pharmaceutical Biotechnology, vol. 5, pp. 321-336, (2004).

Balaji, T. et al., "Optical sensor for the visual detection of mercury using mesoporous silica anchoring porphyrin moiety", The Analyst, vol. 130, pp. 1162-1167, (2005).

Caballero, A. et al., "Highly selective chromogenic and redox or fluorescent sensors of $Hg^{2+}$ in aqueous environment based on 1,4-disubstituted azines", Journal of the American Chemical Society, vol. 127, pp. 15666- 15667, (2005).

Chan, W.H. et al., "Development of a mercury ion-selective optical sensor based on fluorescence quenching of 5,10,15,20-tetraphenylporphyrin", Analytica Chimica Acta, vol. 444, pp. 261-269, (2001).

Chen, P. et al., "A general strategy to convert the merR family proteins into highly sensitive and selective fluorescent biosensors for metal ions", Journal of the American Chemical Society, vol. 126, pp. 728-729, (2004).

Chiuman, W. et al., "Efficient signaling platforms built from a small catalytic DNA and doubly labeled fluorogenic substrates", Nucleic Acids Research, vol. 35, No. 2, pp. 401-405, (2007).

Cruz, R.P.G. et al., "Dinucleotide junction cleavage versatility of 8-17 deoxyribozyme", Chemistry & Biology, vol. 11, pp. 57-67, (2004).

Frasco, M.F. et al., "Mechanisms of cholinesterase inhibition by inorganic mercury", the FEBS Journal, vol. 274, pp. 1849-1861, (2007).

Guo, X. et al., "A highly selective and sensitive fluorescent chemosensor for $Hg^{2+}$ in neutral buffer aqueous solution", The Journal of the American Chemical Society, vol. 126, pp. 2272-2273, (2004).

Harris, H.H. et al., "The chemical form of mercury in fish", Science, vol. 301, pp. 1203, (2003).

Ha-Thi, M-H. et al., "Highly selective and sensitive phosphane sulfide derivative for the detection of $Hg^{2+}$ in an organoaqueous medium", Organic Letters, vol. 9, No. 6, pp. 1133-1136, (2007).

Joyce, G.F. et al., "Directed evolution of nucleic acid enzymes", Annual Review Biochem., vol. 73, pp. 791-836, (2004).

Ko, S-K. et al., "In vivo monitoring of mercury ions using a rhodamine-based molecular probe", Journal of the American Chemical Society, vol. 128, pp. 14150-14155, (2006).

Kuswandi, B. et al., "Capillary optode: determination of mercury(II) in aqueous solution", Analytical Letters, vol. 32, No. 4, pp. 649-664, (1999).

Kuswandi, B. et al., "Selective pool optode for mercury ion sensing in aqueous solution", Sensors and Actuators B, vol. 74, pp. 131-137, (2001).

Lee, J-S. et al., "Colorimetric detection of mercuric ion ($Hg^{2+}$) in aqueous media using DNA-functionalized gold nanoparticles", Angewandte Chemie International Edition, vol. 46, pp. 4093-4096, (2007).

Liu, B. et al., "A selective fluorescent ratiometric chemodosimeter for mercury ion", Chem. Communications, pp. 3156-3158, (2005).
Liu, J. et al., "Fluorescent DNAzyme biosensors for metal ions based on catalytic molecular beacons", Methods in Molecular Biology, vol. 335, pp. 275-288, (2006).
Matsushita, M. et al., "A blue fluorescent antibody-cofactor sensor for mercury", Organic Letters, vol. 7, No. 22, pp. 4943-4946, (2005).
Miyake, Y. et al., "Mercury$^{II}$-mediated formation of thymine-Hg$^{II}$-thymine base pairs in DNA duplexes", Journal of the American Chemical Society, vol. 128, No. 7, pp. 2172-2173, (2006).
Nolan, E.M. et al., "A "turn-on" fluorescent sensor for the selective detection of mercuric ion in aqueous media", Journal of the American Chemical Society, vol. 125, pp. 14270-14271, (2003).
Ono, A. et al., "Highly selective oligonucleotide-based sensor for mercury (II) in aqueous solutions", Angew. Chem. Int. Ed., vol. 43, pp. 4300-4302, (2004).
Ostatna, V. et al., "Self-assembled monolayers of thiol-end-labeled DNA at mercury electrodes", Langmuir, vol. 22, pp. 6481-6484, (2006).
Prodi, L. et al., "An effective fluorescent achemosensor for mercury ions", Journal of the American Chemical Society, vol. 122, No. 28, pp. 6769-6770, (2000).
Silverman, S.K., "Survey and Summary: In vitro selection, characterization, and application of deoxyribozymes that cleave RNA", Nucleic Acids Research, vol. 33, No. 19, pp. 6151-6163, (2005).
Song, K.C. et al., "Fluorogenic Hg$^{2+}$-selective chemodosimeter derived from 8-hydroxyquinoline", Organic Letters, vol. 8, No. 16, pp. 3413-3416, (2006).
Szurdoki, F. et al., "A combinatorial approach to discover new chelators for optical metal ion sensing", Analytical Chemistry, vol. 72, No. 21, pp. 5250-5257, (2000).
Tanaka, Y. et al., "11$^{15}$N-$^{15}$N J-coupling across Hg$^{II}$: Direct observation of Hg$^{II}$-mediated T-T base pairs in a DNA duplex" Journal of the American Chemical Society, vol. 129, No. 2, pp. 244-245, (2007).
Jacoby, M. "Mercury Sensor—Analytical Chemistry: Colorimetric method is sensitive and selective", Chemical & Engineering News, pp. 15, May 7, 2007.
Vannela, R. et al., "In vitro selection of Hg (II) and as (V)-dependent RNA-cleaving DNAzymes", Environmental Engineering Science, vol. 24, No. 1, pp. 73-84, (2007).
Vaughan, A.A. et al., "Optical fibre reflectance sensors for the detection of heavy metal ions based on immobilized Br-PADAP", Sensorsand Actuators B, vol. 51, pp. 368-376, (1998).
Virta, M. et al., "A luminescence-based mercury biosensor", Analytical Chemistry, vol. 67, No. 3, pp. 667-669, (1995).
Wang, J. et al., "Detecting Hg$^{2+}$ ions with an ICT fluorescent sensor molecule: Remarkable emission spectra shift and unique selectivity", Journal of Organic Chemistry, vol. 71, pp. 4308-4311, (2006).
Wang, J. et al., "A series of polyamide receptor based PET fluorescent sensor molecules: Positively cooperative Hg$^{2+}$ ion binding with high sensitivity", Organic Letters, vol. 8, No. 17, pp. 3721-3724, (2006).
Widmann, A. et al., "Mercury detection in seawater using a mercaptoacetic acid modified gold microwire electrode", Electroanalysis, vol. 17, No. 10, pp. 825-831, (2005).
Xiao, Y. et al., "Electrochemical detection of parts-per-billion lead via an electrode-bound DNAzyme assembly", Journal of the American Chemical Society, vol. 129, pp. 262-263, (2007).
Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).
Yang, Y-K. et al., "A rhodamine-based fluorescent and colorimetric chemodosimeter for the rapid detection of Hg2+ ions in aqueous media", Journal of the American Chemical Society, vol. 127, pp. 16760-16761, (2005).
Zhang, X-B. et al "An optical fiber chemical sensor for mercury ions based on a porphyrin dimmer", Analytical Chemistry, vol. 74, No. 4, pp. 821-825, (2002).
Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).
Zhao, Y. et al., "Tuning the sensitivity of a foldamer-based mercury sensor by its folding energy", Journal of the American Chemical Society, vol. 128, No. 31, pp. 9988-9989, (2006).
Zhao, Y. et al., "Detection of Hg2+ in aqueous solutions with a foldamer-based fluorescent sensor modulated by surgactant micelles", Organic Letters, vol. 8, No. 21, pp. 4715-4717, (2006).
Zuker, M., "Mfold web server for nucleic acid folding and hybridization prediction", Nucleic Acids Research, vol. 31, No. 13, pp. 3406-3415, (2003).
International Search Report dated May 10, 2007 for PCT application No. PCT/US2006/030617.
Liu, J. et al., "Smart nanomaterials responsive to multiple chemical stimuli with controllable cooperativity", Advanced Materials, vol. 18, No. 13, pp. 1667-1671, (2006).
Nutiu, R. et al., "Signaling aptamers for monitoring enzymatic activity and for inhibitor screening", Chembiochem—A European Journal of Chemical Biology, vol. 5, No. 8, pp. 1139-1144, (2004).
Nutiu, R. et al., "Structure-switching signaling aptamers: Transducing molecular recognition into fluorescence signaling", Chemistry—A European Journal, vol. 10, No. 8, pp. 1868-1876, (2004).
International Search Report dated Jul. 31, 2007 for PCT application No. PCT/US2007/064055.
Ahern, H., "Biochemical, reagent kits offer scientists good return on investment", The Scientist, vol. 9, No. 15, pp. 20-22, (1995).
Homann, M. et al., "Dissociation of long-chain duplex RNA can occur via strand displacement in vitro: biological implication", Nucleic Acids Research, vol. 24, No. 22, pp. 4395-4400, (1996).
Alivisatos, A.P. et al., "Quantum dots as cellular probes", Annual Review Biomed. Eng, vol. 7, pp. 55-76, (2005).
Dyadyusha, L. et al., "Quenching of CdSe quantum dot emission, a new approach for biosensing", Chemical Communication, pp. 3201-3203, (2005).
Ellington, A.D. et al., "In vitro selection of RNA molecules that bind specific ligands", Nature, vol. 346, pp. 818-822, (1990).
Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).
Goldman, E.R. et al., "Multiplexed toxin analysis using four colors of quantum dot fluororeagents", Analytical Chemistry, vol. 76, No. 3, pp. 684-688, (2004).
Gueroui, Z. et al., "Single-molecule measurements of gold-quenched quantum dots", Physical Review Letters, vol. 93, No. 16, pp. 166108/1-166108/4, (2004).
Han, M. et al., "Quantum-dot-tagged microbeads for multiplexed optical coding of biomolecules", Nature Biotechnology, vol. 19, pp. 631-635, (2001).
Hansen, J.A. et al., "Quantum-dot/Aptamer-based ultrasensitive multi-analyte electrochemical biosensor", Journal of the American Chemical Society, vol. 128, No. 7, pp. 2228-2229, (2006).
Hartig, J.S. et al., "Protein-dependent ribozymes report molecular interactions in real time", Nature Biotechnology, vol. 20, pp. 717-722, (2002).
Herman, T. et al., "Adaptive recognition by nucleic acid aptamers", Science, vol. 287, pp. 820-825, (2000).
Kurreck, J., "Antisense technologies Improvement through novel chemical modifications", Eur. J. Biochem, vol. 270, pp. 1628-1644, (2003).
Lee, J.F. et al., "Aptamer database", Nucleic Acids Research, vol. 32, Database Issue, pp. D95-D100, (2004).
Levy, M. et al., "Quantum-dot aptamer beacons for the detection of proteins", ChemBioChem, vol. 6, pp. 2163-2166, (2005).
Liu, J. et al., "Smart nanomaterials responsive to multiple chemical stimuli with controllable cooperativity", Advanced Materials, vol. 18, pp. 1667-1671, (2006).
Liu, J. et al., "Preparation of aptamer-linked gold nanoparticle purple aggregates for colorimetric sensing of analytes", Nature Protocols, vol. 1, No. 1, pp. 246-252, (2006).
Medintz, I.L. et al., "Quantum dot bioconjugates for imaging, labeling and sensing", Nature Materials, vol. 4, pp. 435-446, (2005).
Midurturu, C. V. et al., "Modulation of DNA constraints that control macromolecular folding", Angew. Chem. Int. Ed., vol. 45, pp. 1918-1921, (2006).

Mitchell, G.P. et al., "Programmed assembly of DNA functionalized quantum dots", Journal of the American Chemical Society, vol. 121, No. 35, pp. 8122-8123, (1999).

Nutiu, R. et al., "Structure-switching signaling aptamers: Transducing molecular recognition into fluorescence signaling", Chem. Eur. J., vol. 10, pp. 1868-1876, (2004).

Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).

Rajendran, M. et al., "In vitro selection of molecular beacons", Nucleic Acids Research, vol. 31, No. 19, pp. 5700-5713, (2003).

Vet, J.A.M. et al., "Multiplex detection of four pathogenic retroviruses using molecular beacons", Proceedings of the National Academy of Science, USA., vol. 96, pp. 6394-6399, (1999).

Wargnier, R. et al., "Energy transfer in aqueous solutions of oppositely charged CdSe/ZnS core/shell quantum dot-nanogold assemblies", Nano Letters, vol. 4, No. 3, pp. 451-457, (2004).

Wilson, R. et al., "Encoded microcarriers for high-throughput multiplexed detection", Angewandte Chemie International Edition, vol. 45, pp. 6104-6117, (2006).

Winkler, W.C. et al., "Regulation of bacterial gene expression by riboswitches", the Annual Review of Microbiology, vol. 59, pp. 487-517, (2005).

Yang, C.J. et al., "Light-switching excimer probes for rapid protein monitoring in complex biological fluids", PNAS, vol. 102, No. 48, pp. 17278-17283, (2005).

Liu, J. et al., "Quantum dot encoding of aptamer-linked nanostructures for one-pot simultaneous detection of multiple analytes", Analytical Chemistry, vol. 79, No. 11, pp. 4120-4125, (2007).

Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).

Allen, M.J. et al., "Magnetic resonance contrast agents for medical and molecular imaging", Met. Ions Biol. Syst., vol. 42, pp. 1-38, (2004).

Artemov, D. et al., "MR molecular imaging of the Her-2/neu receptor in breast cancer cells using targeted iron oxide nanoparticles", Magnetic Resonance in Medicine, vol. 49, pp. 403-408, (2003).

Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).

Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).

Carr, D.H. et al., "Gadolinium-DTPA as a contrast agent in MRI: initial clinical experience in 20 patients", American Journal of Roentfenol., vol. 143, pp. 215-224, (1984).

Chen, Y. et al., "An autonomous DNA nanomotor powered by a DNA enzyme", Angew. Chem. Int. Ed., vol. 43, pp. 3554-3557, (2004).

Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, (2004).

Dodd, C.H. et al., "Normal T-cell response and in vivo magnetic resonance imaging of T cells loaded with HIVv transactivator-peptide-derived superparamagnetic nanoparticles", Journal of Immunological Methods, vol. 256, pp. 89-105, (2001).

Drolet, D.W. et al., "An enzyme-linked oligonucleotide assay", Nature Biotechnology, vol. 14, pp. 1021-1025, (1996).

Enochs, W.S. et al., "Improved delineation of human brain tumors on MR images using a long-circulating, superparamagnetic iron oxide agent", Journal of Magnetic Resonance Imaging, vol. 9, pp. 228-232, (1999).

Famulok, M. et al., "Nucleic acid aptamers-from selection in vitro to applications in vivo", Accounts of Chemical research, vol. 33, No. 9, pp. 591-599, (2000).

Fang, X. et al., "Molecular aptamer for real-time oncoprotein platelet-derived growth factor monitoring by fluorescence anisotropy", Analytical Chemistry, vol. 73, No. 23, pp. 5752-5757, (2001).

Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).

Hamaguchi, N. et al., "Aptamer beacons for the direct detection of proteins", Analytical Biochemistry, vol. 294, pp. 126-131, (2001).

Harisinghani, M.G. et al., "Noninvasive detection of clinically occult lymph-node metastases in prostate cancer", The New England Journal of Medicine, vol. 348, No. 25, pp. 2491-2499, (2003).

Hermann, T. et al., "Adaptive recognition by nucleic acid aptamers", Science, vol. 287, pp. 820-825, (2000).

Hoppe-Seyler, F. et al., "Peptide aptamers: Specific inhibitors of protein function", Current Molecular Medicine, vol. 4, pp. 529-538, (2004).

Huang, C-C. et al., "Aptamer-modified gold nanoparticles for colorimetric determination of platelet-derived growth factors and their receptors", Analytical Chemistry, vol. 77, No. 17, pp. 5735-5741, (2005).

Josephson, L. et al., "High-efficiency intracellular magnetic labeling with novel superparamagnetic-tat peptide conjugates", Bioconjugate Chem., vol. 10, No. 2, pp. 186-191, (1999).

Josephson, L. et al., "The effects of iron oxides on proton relaxivity", Magnetic Resonance Imaging, vol. 6, pp. 647-653, (1988).

Josephson, L. et al., "Magnetic nanosensors for the detection of oligonucleotide sequences", Angew. Chem. Int. Ed., vol. 40, No. 17, pp. 3204-3206, (2001).

Kabalka, G. et al., "Gadolinium-labeled liposomes: Targeted MR contrast agents for the liver and spleen", Radiology, vol. 163, pp. 255-258, (1987).

Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).

Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).

Lee, J. et al., "A steroid-conjugated contrast agent for magnetic resonance imaging of cell signaling", Journal of American Chemical Society, vol. 127, No. 38, pp. 13164-13166, (2005).

Lewin, M. et al., "Tat peptide-derivatized magnetic nanoparticles allow in vivo tracking and recovery of progenitor cells", Nature Biotechnology, vol. 18, pp. 410-414, (2000).

Li, J.J. et al., "Molecular aptamer beacons for real-time protein recognition", Biochemical and Biophysical Research Communications, vol. 292, No. 1, pp. 31-40, (2002).

Li, W-H. et al., "A calcium-sensitive magnetic resonance imaging contrast agent", Journal of the American Chemical Society, vol. 121, No. 6, pp. 1413-1414, (1999).

Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).

Liss, M. et al., "An aptamer-based quartz crystal protein biosensor", Analytical Chemistry, vol. 74, No. 17, pp. 4488-4495, (2002).

Liu, Y. et al., "Aptamer-directed self-assembly of protein arrays on a DNA nanostructure", Angew. Chem. Int. Ed., vol. 44, pp. 4333-4338, (2005).

Macaya, R.F. et al., "Thrombin-binding DNA aptamer forms a unimolecular quadruplex structure in solution", Proceedings of the National Academy of Science USA, vol. 90, pp. 3745-3749, (1993).

Nagel-Wolfrum, K. et al., "The interaction of specific peptide aptamers with the DNA binding domain and the dimerization domain of the transcription factor stat3-inhibits transactivation and induces apoptosis in tumor cells", Molecular Cancer Research, vol. 2, pp. 170-182, (2004).

Nitin, N. et al., "Functionalization and peptide-based delivery of magnetic nanoparticles as an intracellular MRI contrast agent", J. Biol. Inorg. Chem., vol. 9, pp. 706-712, (2004).

Nutiu, R. et al., "Engineering DNA aptamers and DNA enzymes with fluorescence-signaling properties", Pure Appl. Chem., vol. 76, Nos. 7-8, pp. 1547-1561, (2004).

Padmanabhan, K. et al., "The structure of a-thrombin inhibited by a 15-mer single-stranded DNA aptamer", The Journal of Biological Chemistry, vol. 268, No. 24, pp. 17651-17654, (1993).

Pavlov, V. et al., "Aptamer-functionalized au nanoparticles for the amplified optical detection of thrombin", The Journal of the American Chemical Society, vol. 126, No. 38, pp. 11768-11769, (2004).

Pendergrast, P.S. et al., "Nucleic acid aptamers for target validation and therapeutic applications", Journal of Biomolecular Techniques, vol. 16, issue 3, pp. 224-234, (2005).

Perez, J.M. et al., "Use of magnetic nanoparticles as nanosensors to probe for molecular interactions", ChemBioChem, vol. 5, pp. 261-264, (2004).

Perez, J.M. et al., "Viral-induced self-assembly of magnetic nanoparticles allows the detection of viral particles in biological media", Journal of the American Chemical Society, vol. 125, No. 34, pp. 10192-10193, (2003).

Radi, A-E. et al., "Reagentless, reusable, ultrasensitive electrochemical molecular beacon aptasensor", Journal of the American Chemical Society, vol. 128, No. 1, pp. 117-124, (2006).

Saeed, M. et al., "Occlusive and reperfused myocardial infarcts: differentiation with Mn-DPDP-enhanced MR imaging", Radiology, vol. 172, pp. 59-64, (1989).

Shen, T. et al., "Monocrystalline iron oxide nanocompounds (MION): Physicochemical properties", Magn. Reson. Med., vol. 29, pp. 599-604, (1993).

Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).

Soriaga, M.P. et al., "Determination of the orientation of aromatic molecules adsorbed on platinum electrodes: the influence of iodide a surface-active anion", Journal of the American Chemical Society, vol. 104, pp. 2742-2747, (1982).

Soriaga, M.P. et al., "Determination of the orientation of aromatic molecules adsorbed on platinum electrodes: The effect of solute concentration", Journal of the American Chemical Society, vol. 104, pp. 3937-3945, (1982).

Sosnovik, D.E. et al., "Emerging concepts in molecular MRI", Current Opinion in Biotechnology, vol. 18, pp. 4-10, (2007).

Taboada, E. et al., "Relaxometric and magnetic characterization of ultrasmall iron oxide nanoparticles with high magnetization. Evaluation as potential $T_1$ magnetic resonance imaging contrast agents for molecular imaging", Langmuir, vol. 23, No. 8, pp. 4583-4588, (2007).

Tasset, D.M. et al., "Oligonucleotide inhibitors of human thrombin that bind distinct epitopes", J. Mol. Biol., vol. 272, pp. 688-698, (1997).

Tian, Y. et al., "DNAzyme amplification of molecular beacon signal", Talanta, vol. 67, pp. 532-537, (2005).

Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).

Tsourkas, A. et al., "Magnetic relaxation switch immunosensors detect enantiomeric impurities", Angew. Chem. Int. Ed., vol. 43, pp. 2395-2399, (2004).

Wang, S. et al., "Core/shell quantum dots with high relaxivity and photoluminescence for multimodality imaging", Journal of the American Chemical Society, vol. 129, No. 13, pp. 3848-3856, (2007).

Weissleder, R. et al., "MR imaging of splenic metastases: Ferrite-enhanced detection in rats", American Journal Roentgenol., vol. 149, pp. 723-726, (1987).

Xiao, Y. et al., "Label-free electronic detection of thrombin in blood serum by using an aptamer-based sensor", Angew. Chem. Int. Ed., vol. 44, pp. 5456-5459, (2005).

Xiao, Y. et al., "A reagentless signal-on architecture for electronic, aptamer-based sensors via target-induced strand displacement", Journal of the American Chemical Society, vol. 127, No. 51, pp. 17990-17991, (2005).

Xu, D. et al., "Label-free electrochemical detection for aptamer-based array electrodes", Analytical Chemistry, vol. 77, No. 16, pp. 6218-6224, (2005).

Yamamoto, R. et al., "Molecular beacon aptamer fluoresces in the presence of Tat protein of HIV-1", Genes to Cells, vol. 5, pp. 389-396, (2000).

Zhao, M. et al., "Magnetic sensors for protease assays", Angew. Chem. Int. Ed., vol. 42, No. 12, pp. 1375-1378, (2003).

Zhao, M. et al., "Differential conjugation of tat peptide to superparamagnetic nanoparticles and its effect on cellular uptake", Bioconjugate Chem., vol. 13, pp. 840-844, (2002).

Liu, J. et al., "Colorimetric $Cu^{2+}$ detection with a ligation DNAzyme and nanoparticles", Chemical Communications, Advance Articles, DOI: 10.1039/b712421j, 6 pages, Oct. 24, 2007.

Liu, J. et al., "Non-Base pairing DNA provides a new dimension for controlling aptamer-linked nanoparticles and sensors", Journal of the American Chemical Society, vol. 129, No. 27, pp. 8634-8643, (2007).

Liu, J. et al., Supporting Information for "colorimetric $Cu^{2+}$ detection with a ligation DNAzyme and nanoparticles", Chemical Communications, Advance Articles, 4 pages, Oct. 24, 2007.

Stratagene Catolog, "Gene Characterization Kits", 2 pages, (1988).

Fahlman, R.P. et al., "DNA conformational switches as sensitive electronic sensors of analytes", Journal of the American Chemical Society, vol. 124, 4610-4616, (2002).

Mayer, G. et al., "High-throughput-compatible assay for glmS riboswitch metabolite dependence", ChemBioChem, vol. 7, pp. 602-604, (2006).

Elowe, N., et al., "Small-molecule screening made simple for a difficult target with a signaling nucleic acid aptamer that reports on deaminase activity", Angew. Chem. Int. Ed., vol. 45, pp. 5648-5652, (2006).

Yigit, M. et al., "Smart "turn-on" magnetic resonance contrast agents based on aptamer-functionalized superparamagnetic iron oxide nanoparticles", ChemBioChem, vol. 8, pp. 1675-1678, (2007).

Xu, D. et al., "Label-free electrochemical detection for aptamer-based array electrodes", Analytical Chemistry, vol. 77, No. 16, pp. 5107-5113, (2005).

Yigit, M et al., "MRI detection of thrombin with aptamer functionalized superparamagnetic iron oxide nanoparticles", Bioconjugate Chem., vol. 19, pp. 412-417, (2008).

International Search Report dated Mar. 4, 2009 for PCT application No. PCT/US2008/070177.

International Search Report dated Apr. 17, 2009 for PCT application No. PCT/US2008/051185.

International Search Report dated Aug. 13, 2009 for PCT application No. PCT/US2008/072327.

Liu, J. et al., "Rational design of turn-on allosteric DNAzyme catalytic beacons for aqueous mercury ions with ultrahigh sensitivity and selectivity", Angewandte Chemmie. International Edition, vol. 46, No. 40, pp. 7587-7590, (2007).

Stadler, B. et al., "Micropatterning of DNA-tagged vesicles", Langmuir, vol. 20, No. 26, pp. 11348-11354, (2004).

Pfeiffer, I. et al., "Bivalent cholesterol-Based coupling of oligonucletides to lipid membrane assemblies", Journal of the American Chemical Society, vol. 126, No. 33, pp. 10224-10225, (2004).

Shin, J. et al., "Acid-triggered release via dePEGylation of DOPE liposomes containing acid-labile vinyl ether Peg-lipids", Journal of Controlled Release, vol. 91, issues 1-2, pp. 187-200, (2003).

Cram, D.J. et al., "Organic Chemistry", Mcgraw-Hill, pp. 560-569, (1959).

Rusconi, C.P. et al., "Antidote-mediated control of an anticoagulant aptamer in vivo", Nature Biotechnology Letters, vol. 22, No. 11, pp. 1423-1428, (2004).

Willis M.G. et al., "Liposome-anchored vascular endothelial growth factor aptamers", Bioconjugate Chem., vol. 9, No. 5, pp. 573-582, (1998).

Healy, J.M. et al., "Pharmacokinetics and biodistribution of novel aptamer compositions", Pharm. Research, vol. 21, No. 12, pp. 2234-2246, (2004).

Farokhzad, O.C. et al., "Targeted nanoparticle-aptamer bioconjugates for cancer chemotherapy in vivo", Proceedings of the National Academy of Science, vol. 103, No. 16, pp. 6315-6320, (2006).

Farokhzad, O.C. et al., "Nanopartide-aptamer bioconjugates: A new approach for targeting prostate cancer cells", Cancer Research, vol. 64, pp. 7668-7672, (2004).

American Cancer Society Statistics for 2006. http://www.cancer.org/docroot/stt/stt_0.asp 2006.

Eifel, P. et al., "National Institutes of Health Consensus Development Panel, National Institutes of Health Consensus Development Conference statement: Adjuvant therapy for breast cancer, Nov. 1-3, 2000", Journal of the National Cancer Institute, vol. 93, No. 13, pp. 979-989, (2001).

Park, J.W. et al., "Tumor targeting using anti-her2 immunoliposomes", Journal of Controlled Release, vol. 74, pp. 95-113, (2001).

Kallab, V. et al., "HER2/EGFR internalization: a novel biomarker for ErbB-targeted therapeutics", Breast Cancer Research Treat., vol. 88, pp. S126-S127, (2004).

Wilson, K.S. et al., "Differential gene expression patterns in HER2/neu-positive and -negative breast cancer cell lines and tissues", American Journal of Pathology, vol. 161, No. 4, pp. 1171-1185, (2002).

Weigelt, B. et al., "Breast cancer metastasis: Markers and models", Nature Reviews, Cancer, vol. 5, pp. 591-602, (2005).

Pegram, M.D. et al., "Rational combinations of trastuzumab with chemotherapeutic drugs used in the treatment of breast cancer", Journal of the National Cancer Institute, vol. 96, No. 10, pp. 739-749, (2004).

Kirpotin, D.B. et al., "Antibody targeting of long-circulating lipidic nanoparticles does not increase tumor localization but does increase internalization in animal models", Cancer Research, vol. 66, No. 13, pp. 6732-6740, (2006).

Cheng, C. et al., "Formulation of Functionalized PLGA-PEG Nanoparticles for Iin Vivo Targeted Drug Delivery", Biomaterials, vol. 28, issue 5, pp. 869-876, (2007).

Bass, B.L. et al., "Specific interaction between the self-splicing RNA of Tetrahymena and its guanosine substrate: implications for biological catalysis by RNA", Nature, vol. 308, pp. 820-826, (1984).

Ellington, A.D. et al., "Combinatorial methods: aptamers and aptazymes", Part of the SPIE Conference on Advanced Materials and Optical Systems for Chemical and Biological Detection, SPIE, vol. 3858, pp. 126-134, (1999).

Robertson, M.P. et al., "Aptazymes as generalized signal transducers", Nucleic Acids Symp. Ser., vol. 41, pp. 1-3, (1999).

Pagratis, N.C. et al., "Potent 2'-amino-, and 2'-fluoro-2'-deoxyribonucleotide RNA inhibitors of keratinocyte growth factor", Nature Biotechnology, vol. 15, pp. 68-73, (1997).

Lupold, S.E. et al., "Identification and characterization of nuclease-stabilized RNA molecules that bind human prostate cancer cells via the prostate-specific membrane antigen", Cancer research, vol. 62, pp. 4029-4033, (2002).

Jenison, R.D. et al., "Oligonucleotide inhibitors of P-selectin-dependent neutrophil-platelet adhesion", Antisense Nucleic Acid Drug Dev., vol. 8, pp. 265-279, (1998).

Hicke, B.J. et al., "DNA aptamers block L-selectin function in vivo. Inhibition of human lymphocyte trafficking in SCID mice", J. Clinical Invest., vol. 98, No. 12, pp. 2688-2692, (1996).

O'Connell, D. et al., "Calcium-dependent oligonucleotide antagonists specific for L-selectin", Proceedings of the National Academy of Science, U.S.A., vol. 93, pp. 5883-5887, (1996).

Soukup, G.A. et al., "Design of allosteric hammerhead ribozymes activated by ligand-induced structure stabilization", Structure, vol. 7, pp. 783-791, (1999).

Straubinger, R.M. et al., "Preparation and characterization of taxane-containing liposomes", Methods in Enzymology, vol. 391, pp. 97-117, (2005).

Rivera, E. "Liposomal anthracyclines in metastatic breast cancer: Clinical update", The Oncologist, vol. 8, supplement 2, pp. 3-9, (2003).

Kornblith, P. et al., "Breast cancer—Response rates to chemotherapeutic agents studied in vitro", Anticancer Research, vol. 23, pp. 3405-3411, (2003).

Pei, J. et al., "Combination with liposome-entrapped, ends-modified raf antisense oligonucleotide (LErafAON) improves the anti-tumor efficacies of cisplatin, epirubicin, mitoxantrone, docetaxel and gemcitabine", Anti-Cancer Drugs, vol. 15, pp. 243-253, (2004).

Allen, T.M. et al., "Therapeutic opportunities for targeted liposomal drug delivery", Advanced Drug Delivery Reviews, vol. 21, pp. 117-133, (1996).

Hofheinz, R.D. et al., "Liposomal encapsulated anti-cancer drugs", Anti-Cancer Drugs, vol. 16, pp. 691-707, (2005).

Schluep, T. et al., "Preclinical efficacy of the camptothecin-polymer conjugate IT-101 in multiple cancer models", Clinical Cancer Research, vol. 12, No. 5, pp. 1606-1614, (2006).

Schluep, T. et al., "Pharmacokinetics and biodistribution of the camptothecin-polymer conjugate IT-101 in rats and tumor-bearing mice", Cancer Chemoth. Pharm., vol. 57, pp. 654-662, (2006).

Cheng, J. et al., "Antitumor Activity of beta-Cyclodextrin Polymer-Camptothecin Conjugates", Molecular Pharmaceutics, vol. 1, No. 3, pp. 183-193, (2004).

Cheng, J. et al., "Synthesis of linear, beta-cyclodextrin-based polymers and their camptothecin conjugates", Bioconjugate Chem., vol. 14, pp. 1007-1017, (2003).

Guo, X. et al., "Steric stabilization of fusogenic liposomes by a low-pH sensitive PEG-diortho ester-lipid conjugate", Bioconjugate Chem., vol. 12, pp. 291-300, (2001).

Gerasimov, O.V. et al., "Cytosolic drug delivery using pH- and light-sensitive liposomes", Advanced Drug Delivery Reviews., vol. 38, pp. 317-338, (1999).

Rovira-Bru, M. et al., "Size and structure of spontaneously forming liposomes in lipid/PEG-lipid mixtures", Biophysical Journal, vol. 83, pp. 2419-2439, (2002).

Liu, J. et al., "Proofreading and error removal in a nanomaterial assembly", Angewandte Chemie, International Edition, vol. 44, pp. 7290-7293, (2005).

Liu, J. et al., "Design of asymmetric DNAzymes for dynamic control of nanoparticle aggregation states in response to chemical stimuli", Organic & Biomolecular Chemistry, vol. 4, pp. 3435-3441, (2006).

Cho, H.S. et al., "Structure of the extracellular region of HER2 alone and in complex with the Herceptin Fab", Nature, vol. 421, pp. 756-760, (2003).

Leahy, D.J. et al., "A Mammalian Expression Vector for Expression and Purification of Secreted Proteins for Structural Studies", Protein Expression and Purification, vol. 20, pp. 500-506, (2000).

Bartel, D.P. et al., "Isolation of new ribozymes from a large pool of random sequences", Science, vol. 261, pp. 1411-1418, (1993).

Jellinek, D. et al., "Inhibition of receptor binding by high-affinity RNA ligands to vascular endothelial growth factor", Biochemistry, vol. 33, pp. 10450-10456, (1994).

Jellinek, D. et al., "Potent 2'-Amino-2'-deoxypyrimidine RNA Inhibitors of Basic Fibroblast Growth Factor", Biochemistry, vol. 34, pp. 11363-11372, (1995).

Green, L.S. et al., "Inhibitory DNA Ligands to Platelet-Derived Growth Factor B-Chain", Biochemistry, vol. 35, pp. 14413-14424, (1996).

Lee, T.C. et al., "Overexpression of RRE-derived sequences inhibits HIV-1 replication in CEM cells", New Biologist, vol. 4, p. 66, (1992).

Lupoid, S.E. et al., "Identification and characterization of nuclease-stabilized RNA molecules that bind human prostate cancer cells via the prostate-specific membrane antigen", Cancer Research, vol. 62, pp. 4029-4033, (2002).

Andresen, T.L. et al., "Advanced strategies in liposomal cancer therapy: Problems and prospects of active and tumor specific drug release", Progress in Lipid Research, vol. 44, pp. 68-97, (2005).

Woodle, M.C. et al., "Sterically Stabilized Liposomes—Reduction in electrophoretic mobility but not electrostatic surface potential", Biophysical Journal, vol. 61, pp. 902-910, (1992).

Zalipsky, S. et al., "Long Circulating, Cationic Liposomes Containing Amino-Peg-Phosphatidylethanolamine", FEBS Letters, vol. 353, pp. 71-74, (1994).

Morrison, W., "A fast, simple and reliable method for the microdetermination of phosphorus in biological materials", Analytical Biochemistry, vol. 7, issue 2, pp. 218-224, (1964).
Kirpotin, D. et al., "Sterically Stabilized Anti-HER2 Immunoliposomes: Design and Targeting to Human Breast Cancer Cells in Vitro", Biochemistry, vol. 36, pp. 66-75, (1997).
Klibanov, A.L. et al., "Activity of Amphipathic Poly(Ethylene Glycol)-5000 to Prolong the Circulation Time of Liposomes Depends on the Liposome Size and Is Unfavorable for Immunoliposome Binding to Target", Biochim. Biophys. Acta, vol. 1062, pp. 142-148, (1991).
Park, J.W. et al., "Development of Anti-P185$^{HER2}$ Immunoliposomes for Cancer-Therapy", Proceedings of the National Academy of Science U.S.A., vol. 92, pp. 1327-1331, (1995).
Zalipsky, S. "Synthesis of an End-Group Functionalized Polyethylene Glycol-Lipid Conjugate for Preparation of Polymer-Grafted Liposomes", Bioconjugate Chem., vol. 4, pp. 296-299, (1993).
Allen, T.M. et al., "A New Strategy for Attachment of Antibodies to Sterically Stabilized Liposomes Resulting in Efficient Targeting to Cancer-Cells", Biochimica et Biophysica Acta, vol. 1237, pp. 99-108, (1995).
Gillies, E.R. et al., "A new approach towards acid sensitive copolymer micelles for drug delivery", Chemical Communications, Issue 14, pp. 1640-1641, (2003).
Joensuu, O.I., "Fossil Fuels as a Source of Mercury Pollution", Science, vol. 172, No. 3987, pp. 1027-1028, (1971).
Malm, O., "Gold mining as a source of mercury exposure in the Brazilian Amazon", Environmental Research, vol. 77, No. 2, pp. 73-78, (1998).
Tchounwou, P.B. et al., "Environmental exposure to mercury and its toxicopathologic implications for public health", Environmental Toxicology, vol. 18, No. 3,pp. 149-175, (2003).
Yoon, S. et al., "A bright and specific fluorescent sensor for mercury in water, cells, and tissue", Angewandte Chemie International Edition, vol. 46, No. 35, pp. 6658-6661, (2007).
Liu, X.F. et al., "Optical detection of mercury(II) in aqueous solutions by using conjugated polymers and label-free oligonucleotides", Advanced Materials, vol. 19, No. 11, p. 1471, (2007).
Chiang, C.K. et al., "Oligonucleotide-based fluorescence probe for sensitive and selective detection of mercury (II) in aqueous solution", Analytical Chemistry, vol. 80, No. 10, pp. 3716-3721, (2008).
Yamini, Y. et al., "Solid phase extraction and determination of ultra trace amounts of mercury(II) using octadecyl silica membrane disks modified by hexathia-18-crown-6-tetraone and cold vapour atomic absorption spectrometry", Analytica Chimica Acta, vol. 355, issue 1, pp. 69-74, (1997).
Darbha, G.K. et al., "Gold nanoparticle-based miniaturized nanomaterial surface energy transfer probe for rapid and ultrasensitive detection of mercury in soil, water, and fish", Acs Nano, vol. 1, No. 3, pp. 208-214, (2007).
Li, D. et al., "Optical analysis of Hg2+ ions by oligonucleotide-gold-nanoparticle hybrids and DNA-based machines", Angewandte Chemie International Edition, vol. 47, No. 21, pp. 3927-3931, (2008).
Liu, C.W. et al., "Detection of mercury(II) based on Hg2+-DNA complexes inducing the aggregation of gold nanoparticles", Chemical Communications, vol. 19, pp. 2242-2244, (2008).
Xue, X. et al., "One-step, room temperature, colorimetric detection of mercury (Hg2+) using DNA/nanoparticle conjugates", Journal of the American Chemical Society, vol. 130, No. 11, pp. 3244-3245, (2008).
Wang, L. et al., "Gold nanoparticle-based optical probes for target-responsive DNA structures", Gold Bulletin, vol. 41, No. 1, pp. 37-41, (2008).
Clarkson, T.W. et al., "Mercury—Major Issues in Environmental-Health", Environmental Health Perspectives, vol. 100, pp. 31-38, (1993).
Wren, C.D. "A Review of Metal Accumulation and Toxicity in Wild Mammals, 1 Mercury", Environmental Research, vol. 40, No. 1, pp. 210-244, (1986).
Koos, B.J. et al., "Mercury Toxicity in Pregnant Woman, Fetus, and Newborn-Infant-Review", American Journal of Obstetrics and Gynecology, vol. 126, No. 3, pp. 390-409, (1976).

Yu, Y. et al., "p-dimethylaminobenzaldehyde thiosemicarbazone: A simple novel selective and sensitive fluorescent sensor for mercury(II) in aqueous solution", Talanta, vol. 69, No. 1, pp. 103-106, (2006).
Braman, R.S., "Membrane Probe—Spectral Emission Type Detection System for Mercury in Water", Analytical Chemistry, vol. 43, No. 11, pp. 1462-1467, (1971).
Wernette, D.P. et al., "Surface immobilization of catalytic beacons based on ratiometric fluorescent DNAzyme sensors: a systematic study", Langmuir, vol. 23, No. 18, pp. 9513-9521, (2007).
Wang, Z. et al., "Highly sensitive "turn-on" fluorescent sensor for Hg2+ in aqueous solution based on structure-switching DNA", Chemical Communications, pp. 6005-6007, (2008).
Lu, Y. "New catalytic DNA fluorescent and colorimetric sensors for on-sit and real-time monitoring of industrial and drinking water", ISTC Reports, Illinois Sustainable Technology Center Institute of Natural Resource Sustainability, University of Illinois at Urbana-Champaign, http://www.istc.illinois.edu/info/library_docs/RR/RR-114.pdf, pp. i-ix, and 1-30, (2009).
Turner, A. P. F., "Biochemistry: Biosensors—Sense and Sensitivity", Science, vol. 290, No. 5495, pp. 1315-1317, (2000).
Abbasi, S. A., "Atomic absorption spectrometric and spectrophotometric trace analysis of uranium in environmental samples with n-p-methoxyphenyl-2-4-(2-pyridylazo) resorcinol", Int. J. Environ. Anal. Chem., vol. 36, pp. 163-172, (1989).
Arnez, J. G. et al., "Crystal structure of unmodified tRNA$^{Gln}$ complexed with glutaminyl-tRNA synthetase and ATP suggests a possible role for pseudo-uridines in stabilization of RNA structure", Biochemistry, vol. 33, pp. 7560-7567, (1994).
Blake, R. C., II, et al., "Novel monoclonal antibodies with specificity for chelated uranium (VI): isolation and binding properties", Bioconjug. Chem., vol. 15, pp. 1125-1136, (2004).
Boomer, D. W., et al, "Determination of uranium in environmental samples using inductively coupled plasma mass spectrometry", Anal. Chem., vol. 59, pp. 2810-2813, (1987).
Breaker, R. R., "Natural and engineered nucleic acids as tools to explore biology", Nature, vol. 432, pp. 838-845, (2004).
Brina, R. et al., "Direct detection of trace levels of uranium by laser-induced kinetic phosphorimetry", Anal. Chem., vol. 64, pp. 1413-1418, (1992).
Chung N. et al., "Selective extraction of gold(III) in the presences of Pd(II) and Pt(IV) by saltin-out of the mixture of 2-propanol and water", Talanta, vol. 58, pp. 927-933, (2002).
Craft, E. et al., "Depleted and natural uranium: chemistry and toxicological effects", J. Toxicol. Environ. Health, Part B, vol. 7, pp. 297-317, (2004).
Demers, L. M. et al., "Thermal desorption behavior and binding properties of DNA bases and nucleosides on gold", J. Am. Chem. Soc. vol. 124, pp. 11248-11249, (2002).
Frankforter G. et al., "Equilibria in the systems of the higher alcohols, water and salts", J. Am. Chem. Soc., vol. 37, pp. 2697-2716 (1915).
Frankforter G., et al., "Equilibria in the systems, water, acetone and inorganic salts", J. Am. Chem. Soc., vol. 36, pp. 1103-1134, (1914).
Frankforter G., et al., "Equilibria in systems containing alcohols, salts and water, including a new method of alcohol analysis", J. Phys. Chem., vol. 17, pp. 402-473, (1913).
Ginnings, P. et al., "Ternary systems: water, tertiary butanol and salts at 30° C", J. Am. Chem. Soc., vol. 52, pp. 2282-2286, (1930).
Gongalsky, K., "Impact of pollution caused by uranium production on soil macrofauna", Environ. Monit. Assess., vol. 89, pp. 197-219, (2003).
Homola, J. et al., "Surface Plasmon Resonance (SPR) Sensors", Springer Series on Chemical Sensors and Biosensors, vol. 4, pp. 45-67, (2006).
US EPA, "Drinking water contaminants", found at http://www.epa.gov/safewater/contaminants/index.html, pp. 1-17, printed on Nov. 23, 2009.
Jones, L. A., et al., "Extraction of phenol and its metabolites from aqueous solution", J. Agric. Food Chem., vol. 41, pp. 735-741, (1993).
Katz, E. et al., "Integrated nanoparticle-biomolecule hybrid systems: sythesis, properties, and applications", Angew. Chem. Int. Ed., vol. 43, pp. 6042-6108, (2004).

Kobe, K. A. et al., "The ternary systems ethylene glycol-potassium carbonate-water and dioxane-potassium carbonate-water", J. Phys. Chem., vol. 446, pp. 629-633, (1940).

Laromaine, A. et al., "Protease-triggered dispersion of nanoparticle assemblies", J. Am. Chem. Soc., vol. 129, pp. 4156-4157, (2007).

Lazarova, Z. et al., "Solvent extraction of lactic acid from aqueous solution", Journal of Biotechnology, vol. 32, pp. 75-82, (1994).

Lee, J. H. et al., "Site-specific control of distances between gold nanoparticles using phosphorothioate anchors on DNA and a short bifunctional molecular fastener", Angew. Chem. Int. Ed., vol. 46, pp. 9006-9010, (2007).

Leggett, D. C. et al., "Salting-out solvent extraction for preconcentration of neutral polar organic solutes from water", Anal. Chem., vol. 62, pp. 1355-1356, (1990).

Leinonen, H., "Stress corrosion cracking and life prediction evaluation of austenitic stainless steels in calcium chloride solution", Corrosion Science, vol. 52, No. 5, pp. 337-346, (1996).

Li, D. et al., "Amplified electrochemical detection of DNA through the aggregation of Au nanoparticles on elctrodes and the incorporation of methylene blue into the DNA-crosslinked structure", Chem. Comm., pp. 3544-3546, (2007).

Li, H. et al., "Detection of specific sequences in rna using differential adsorption of single-stranded oligonucleotides on gold nanoparticles", Anal. Chem., vol. 77 No. 19, pp. 6229-6233, (2005).

Li, H. et al., "Colorimetric detection of dna sequences based on electrostatic interactions with unmodified gold nanoparticles", Proc. Natl. Acad. Sci. U.S.A., vol. 101, pp. 14036-14039, (2004).

Li, H. et al., "Label-free colorimetric detection of specific sequences in genomic dna amplified by the polymerase chain reaction", J. Am. Chem. Soc., vol. 126, pp. 10958-10961, (2004).

Likidis, Z. et al., "Recovery of penicillin G from fermentation broth with reactive extraction in a mixer-settler", Biotechnology Letters, vol. 9, No. 4, pp. 229-232, (1987).

Lim, I. et al., "Homocysteine-mediated reactivity and assembly of gold nanoparticles", Langmuir, vol. 23, pp. 826-833, (2007).

Lu, Y. et al., "Functional DNA nanotechnology:emerging applications of DNAzymes and aptamers", Curr. Opion. Biotech., vol. 17, pp. 580-588, (2006).

Long, F. A., et al., "Activity coefficients of nonelectrolyte solutes in aqueous salt solutions", Chem. Rev., vol. 51, pp. 119-169, (1952).

Lu, X. et al., "Salting-out separation and liquid-liquid equilibrium of tertiary butanol aqueous solution", Chemical Engineering Journal, vol. 78, pp. 165-171, (2000).

Lu, Y. et al., "Smart nanomaterials inspired by biology: dynamic assembly of error-free nanomaterials in response to multiple chemical and biological stimuli", Accounts of Chemical Research, vol. 40, pp. 315-323, (2007).

Mlakar, M. et al., "Stripping voltammetric determination of trace levels of uranium by synergic adsorptions", Analytica Chimica Acta, vol. 221, pp. 279-287, (1989).

Nishihama, S., "Review of advanced liquid-liquid extraction systems for the separation of metal ions by a combination of conversion of the metal species with chemical reaction", Ind. Eng. Chem. Res., vol. 40, pp. 3085-3091, (2001).

Pierotti, R. A., "A scaled particle theory of aqueous and nonaqueous solutions", Chemical Reviews, vol. 76, No. 6, pp. 717-726, (1976).

Centers for Disease Control, "Preventing lead poisoning in young children", U.S. Department of Health and Human Services, Public Health Service, Centers for Disease Control: Atlanta, GA, (1991).

Public Law 102-550; Residential Lead-Based Paint Hazard Reduction Act of the housing and Community Development Act of 1992; 28 pages, (1992).

Qiang, Z. et al., "Potentiometric determination of acid dissociation constants ($pK_a$) for human and veterinary antibiotics", Water Research, vol. 38, pp. 2874-2890, (2004).

Rohwer, H. et al., "Interactions of uranium and thorium with arsenazo III in an aqueous medium", Analytica Chimica Acta, vol. 341, pp. 263-268, (1997).

Safavi, A. et al., "A novel optical sensor for uranium determination", Analytica Chimica Acta vol. 530, pp. 55-60, (2005).

Sato, K. et al., "Rapid aggregation of gold nanoparticles induced by non-cross-linking DNA hybridization", J. Am. Chem. Soc., vol. 125, pp. 8102-8103, (2003).

Schenk, F. J. et. al., "Comparison of magnesium sulfate and sodium sulfate for removal of water from pesticide extracts of foods", J. AOAC International, vol. 85, No. 5, pp. 1177-1180, (2002).

Sessler, J. L. et al., "Hexaphyrin (1.0.1.0.0.0). a new colorimetric actinide sensor", Tetrahedron, vol. 60, pp. 11089-11097, (2004).

Shafer-Peltier, K. E. et al., "Toward a glucose biosensor based on surface-enhanced raman scattering", J. Am Chem. Soc., vol. 125, pp. 588-593, (2003).

Sharma, J. et al., "DNA-templated self-assembly of two-dimensional and periodical gold nanoparticle arrays", Angew. Chem. Int. Ed., vol. 45, pp. 730-735, (2006).

Si, S. Et al., "pH-controlled reversible assembly of peptide-functionalized gold nanoparticles", Langmuir, vol. 23, pp. 190-195, (2007).

Simard, J. et al., "Formation and pH-controlled assembly of amphiphilic gold nanoparticles", Chemical Commun., pp. 1943-1944, (2000).

Singleton, V. L., "An extraction technique for recovery of flavors, pigments, and other constituents from wines and other aqueous solutions", Am. J. Enol. Vitic., vol. 12, pp. 1-8, (1961).

Rao, C.V.S.R. et al., "Extraction of acetonitrile from aqueous solutions. 1. Ternary liquid equilibria", Journal of Chemical and Engineering Data, vol. 23, No. 1, pp. 23-25, (1978).

Rao, D.S. et al., "Extraction of acetonitrile from aqueous solutions. 2. ternary liquid equilibria", Journal of Chemical and Engineering Data, vol. 24, No. 3, pp. 241-244, (1979).

Tabata, M. et al., "Ion-pair extraction of metalloporphyrins into acetonitrile for determination of copper(II)", Analytical Chemistry, vol. 68, No. 5, pp. 758-762, (1996).

Tabata, M. et al., "Chemical properties of water-miscible solvents separated by salting-out and their application To solvent extraction", Analytical sciences, vol. 10, pp. 383-388, (1994).

Van der Wal, Sj., "Low viscosity organic modifiers in reversed-phase HPLC", Chromatographia, vol. 20, No. 5, pp. 274-278, (1985).

Wang, J. et al., "A gold nanoparticle-based aptamer target binding readout for ATP assay", Adv. Mater., vol. 19, pp. 3943-3946, (2007).

Wang, L. et al., "Unmodified gold nanoparticles as a colorimetric probe for potassium DNA aptamers", Chem. Comm., vol. 36, 3780-3782, (2006).

Wang, Z. et al., "Label-free colorimetric detection of lead ions with a nanomolar detection limit and tunable dynamic range by using gold nanoparticles and DNAzyme", Advanced Materials, vol. 20, pp. 3263-3267. (2008).

Warren, K. W., Reduction of corrosion through improvements in desalting, Benelux Refinery Symposium, Lanaken, Belgium, 11 pages, (1995).

Wei, H. et al., "Simple and sensitive aptamer-based colorimetric sensing of protein using unmodified gold nanoparticle probes", Chem. Comm., vol. 36, pp. 3735-3737, (2007).

Wernette, D. P. et al., "Surface immobilization of catalytic beacons based on ratiometric fluorescent DNAzyme sensors: A systematic study", Langmuir, vol. 23, pp. 9513-9521, (2007).

Willner, I. et al., "Electronic aptamer-based sensors", Angew. Chem., Int. Ed., vol. 46, pp. 6408-6418, (2007).

Wu, Y. G., et al., "An extended Johnson-Furter equation to salting-out phase separation of aqueous solution of water-miscible organic solvents", Fluid Phase Equilibria, vol. 192, pp. 1-12, (2001).

Yan, H., "Nucleic acid nanotechnology", Science, vol. 306, pp. 2048-2049, (2004).

Yang, W. H. et al., "Discrete dipole approximation for calculating extinction and raman intensities for small particles with arbitrary shapes", J. Chem. Phys., vol. 103, pp. 869-875, (1995).

Deng, Z. et al., "DNA-Encoded self-assembly of gold nanoparticles into one-dimensional arrays", Angew. Chem Int. Ed., vol. 44, pp. 3582-3585, (2005).

Zhao, W. et al., "Simple and rapid colorimetric biosensors based on DNA aptamer and noncrosslinking gold naoparticle aggregation", ChemBioChem, vol. 8, pp. 727-731, (2007).

Zhao, W. et al., "Highly stabilized nucleotide-capped small gold nanoparticles with tunable size", Advanced Materials, vol. 19, pp. 1766-1771, (2007).

Zhao, W. et al., "DNA polymerization on gold nanoparticles through rolling circle amplification: towards novel scaffolds for three-dimensional periodic nanoassemblies", Angew. Chem. Int. Ed., vol. 45, pp. 2409-2413, (2006).

Zhao, W. et al., "DNA aptamer folding on gold nanoparticles: from colloid chemistry to bionsenors", J. Am Chem. Soc., vol. 130, (11), pp. 3610 -3618, (2008).

Zhou, P. et al., "Extraction of oxidized and reduced forms of uranium from contaminated soils: effects of carbonate concentration pH", Environmental Science Technology, vol. 39, No. 12, pp. 4435-4440, (2005).

Jacoby, M., "Sensitive, selective mercury sensor nanoparticle-based colorimetric method detects part-per-billion levels of mercury", Chemical & Engineering News, pp. 1-3, May 2, 2007.

Cruz, R.P.G. et al., supplemental to "Dinucleotide junction cleavage versatility of 8-17 deoxyribozyme", Chemistry & Biology, vol. 11, pp. 57-67, (pp. 1-8) (2004).

Saleh, O. A. et al., "Direct detection of antibody-antigen binding using an on-chip artificial pore", Proceedings of the National Academy of Science, vol. 100, No. 3, pp. 820-824, (2003).

Han, C. et al., "Highly selective and sensitive colorimetric probes for $Yb^{3+}$ ions based on supramolecular aggregates assembled from B-cyclodextrin-4,4'-dipyridine inclusion complex modified silver nanoparticles", Chem. Commun., pp. 3545-3547, (2009).

Aldaye, F.A., et al., "Sequential Self-Assembly of a DNA Hexagon as a Template for the Organization of Gold Nanoparticles", Angew. Chem. Int. Ed., 45, pp. 2204-2209, 2006.

Loweth, C.J. et al., "DNA-Based Assembly of Gold Nanocrystals", Angew. Chem. Int. Ed., 38, No. 12, pp. 1808-1812, 1999.

Carbone, A., et al., "Circuits and programmable self-assembling DNA structures", Proceedings of the National Academy of Sciences of the United States of America, vol. 99, No. 20, pp. 12577-12582, 2002.

Chelyapov, N., et al., "DNA Triangles and Self-Assembled Hexagonal Tilings", J. Am. Chem. Soc., 126, pp. 13924-13925, 2004.

Conway, N.E., et al., "The Covalent Attachment of Multiple Fluorophores to DNA Containing Phosphorothioate Diesters Results in Highly Sensitive Detection of Single-Stranded DNA", Bioconjugate Chem, 2, pp. 452-457, 1991.

Ding, B., et al., "Pseudohexagonal 2D DNA Crystals from Double Crossover Cohesion", J. Am. Chem. Soc., 126, pp. 10230-10231, 2004.

Endo, M., et al., "DNA Tube Structures Controlled by a Four-Way-Branched DNA Connector", Angew. Chem. Int. Ed., 44, pp. 6074-6077, 2005.

Fidanza, J.A, et al. "Site-Specific Labeling of DNA Sequences Containing Phosphorothioate Diesters", J. Am. Chem. Soc., 114, pp. 5509-5517, 1992.

Goodman, R.P., et al., "Rapid Chiral Assembly of Rigid DNA Building Blocks for Molecular Nanofabrication", Science, 310, pp. 1661-1665, 2005.

Hagleitner, C., et al., "Smart single-chip gas sensor microsystem", Nature, vol. 414, pp. 293-296, 2001.

He, Y., et al., "Sequence Symmetry as a Tool for Designing DNA Nanostructures", Angew. Chem. Int. Ed., 44, pp. 6694-6696, 2005.

Heath, J.R., et al., "A Defect-Tolerant Computer Architecture: Opportunities for Nanotechnology", Science, vol. 280, pp. 1716-1719, 1998.

Holloway, G., et al., "An Organometallic Route to Oligonucleotides Containing Phosphoroselenoate", ChemBioChem, 3, pp. 1061-1065, 2002.

Li, H., et al., "DNA-Templated Self-Assembly of Protein and Nanoparticle Linear Arrays", J. Am. Chem. Soc., 126, pp. 418-419, 2004.

Cunningham, L., et al., "Spectroscopic Evidence for Inner-Sphere Coordination of Metal Ions to the Active Site of a Hammerhead Ribozyme", J. Am. Chem. Soc., 120, pp. 4518-4519, 1998.

Luduena, R.F., et al., N,N-Bis($\alpha$-iodoacetyl)-2,2'-dithiobis(ethylamine), a Reversible Crosslinking Reagent for Protein Sulfhydryl Groups, Analytical Biochemistry, 117. pp. 76-80, 1981.

Lund, K., et al., "Self-Assembling a Molecular Pegboard", J. Am. Chem. Soc., 127, pp. 17606-17607, 2005.

Mathieu, F., et al. "Six-Helix Bundles Designed from DNA", Nano Letters, vol. 5, No. 4, pp. 661-665, 2005.

Liu, H., et al, "Approaching The Limit: Can One DNA Oligonucleotide Assemble into Large Nanostructures?", Angew. Chem., 118, pp. 1976-1979, 2006.

Fidanza, J. et al, "Introduction of Reporter Groups at Specific Sites in DNA Containing Phosphorothioate Diesters", J. Am. Chem. Soc., 111, pp. 9117-9119, 1989.

Nakao, H., et al, "Highly Ordered Assemblies of Au Nanoparticles Organized on DNA", Nano Letters, vol. 3, No. 10, pp. 1391-1394, 2003.

Patolsky, F., et al., "Au-Nanoparticle Nanowires Based on DNA and Polylysine Templates", Angew. Chem. Int. Ed., 41, No. 13, pp. 2323-2327, 2002.

Pinto, Y., et al., "Sequence-Encoded Self-Assembly of Multiple-Nanocomponent Arrays by 2D DNA Scaffolding", Nano Letters, vol. 5, No. 12, pp. 2399-2402, 2005.

Rothemund, P., "Folding DNA to create nanoscale shapes and patterns", Nature, vol. 440, pp. 297-302, 2006.

Yang, X., et al, "Ligation of DNA Triangles Containing Double Crossover Molecules", J. Am. Chem. Soc., 120, pp. 9779-9786, 1998.

Seeman, N.C., "Nucleic Acid Nanostructures and Topology", Angew. Chem. Int. Ed., 37, pp. 3220-3238, 1998.

Seeman, N. C., "At the Crossroads of Chemistry, Biology, and Materials: Structural DNA Nanotechnology", Chemistry & Biology, vol. 10, pp. 1151-1159, 2003.

Le, J.D., et al., "DNA-Templated Self-Assembly of Metallic Nanocomponent Arrays on a Surface", Nano Letters, vol. 4, No. 12, pp. 2343-2347, 2004.

Seeman, N.C., et al. "Nucleic acid nanostructures: bottom-up control of geometry on the nanoscale", Reports on Progress in Physics, 68, pp. 237-270, 2005.

Warner, M.G., et al., "Linear assemblies of nanoparticles electrostatically organized on DNA scaffolds", Nature Materials, vol. 2, pp. 272-277, 2003.

Winfree, E., et al., "Design and self-assembly of two-dimensional DNA crystals", Nature, vol. 394, pp. 539-544, 1998.

Woehrle, G.H., et al., "Molecular-Level Control of Feature Separation in One-Dimensional Nanostructure Assemblies Formed by Biomolecular Nanolithography", Langmuir, 20, pp. 5982-5988, 2004.

Zhang, J., et al, "Periodic Square-Like Gold Nanoparticle Arrays Templated by Self-Assembled 2D DNA Nanogrids on a Surface", Nano Letters, vol. 6, No. 2, pp. 248-251, 2006.

Yang, T. et al. "Tunneling Phase Logic Cellular Nonlinear Networks", International Journal of Bifurcation and Chaos, vol. 11, No. 12, pp. 2895-2911, 2001.

Liu, Z., et al., "Imaging DNA Molecules on Mica Surface by Atomic Force Microscopy in Air and in Liquid", Microscopy Research and Technique, 66, pp. 179-185, 2005.

Niemeyer, C.M., et al., "Covalent DNA-Streptavidin Conjugates as Building Blocks for Novel Biometallic Nanostructures", Angew. Chem. Int. Ed., 37, No. 16, pp. 2265-2268, 1998.

"What wavelength goes with a color" from eosweb. larc. Nasa.gov. Printed on Jan. 7, 2011.

Cadmium sulfide from Wikipedia, the free encyclopedia. Printed on Jan. 7, 2011.

Yeh et al., Quantum dot-mediated biosensing assays for specific nucleic acid detection. Nanomedicine, 1, 115-121, 2005.

* cited by examiner

SEQUENCE LISTING

```
<160> NUMBER OF SEQ ID NOS: 33

<210> SEQ ID NO 1
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
ccatctctgc agtcgggtag ttaaaccgac cttcagacat agtgagt             47

<210> SEQ ID NO 2
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
```
actcactata rggaagagat gg                                          22

<210> SEQ ID NO 3
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
ccatctcttc agttcggaaa cgaaccttca gacatagtga gt                    42

<210> SEQ ID NO 4
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ccatctcttc agttcggaaa cgtaccttca gacatagtga gt                    42

<210> SEQ ID NO 5
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
ccatctcttc agtttcggaa acgttacctt cagacatagt gagt                  44

<210> SEQ ID NO 6
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
ccatctcttc agttttcgga aacgtttacc ttcagacata gtgagt                46

<210> SEQ ID NO 7
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
ccatctcttc agtttttcgg aaacgtttta ccttcagaca tagtgagt              48

<210> SEQ ID NO 8
<211> LENGTH: 50
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 8
ccatctcttc agttttttcg gaaacgtttt taccttcaga catagtgagt                    50

<210> SEQ ID NO 9
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
ccatctcttc agttttttc ggaaacgttt tttaccttca gacatagtga gt                  52

<210> SEQ ID NO 10
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
catctcttct ccgagccggt cgaaatagtg agt                                      33

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
actcactata rggaagagat g                                                   21

<210> SEQ ID NO 12
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
catctcttct ccgagccggt cgaaatattt ttagctgaaa agcttttaaa agtgagt            57

<210> SEQ ID NO 13
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(9)
<223> OTHER INFORMATION: a, c, g, t, unknown or other

<400> SEQUENCE: 13
actcacnnnt atarggaaga gatg                                                24
```

```
<210> SEQ ID NO 14
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
gggcaaggct agctacaacg actacggcag tc                                    32

<210> SEQ ID NO 15
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gacugccgua gguugccc                                                    18

<210> SEQ ID NO 16
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
gggcaaggct agctacaacg actaaatttt tagctgaaaa gcttttaacg gcagtc          56

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (9)..(11)
<223> OTHER INFORMATION: a, c, g, u, unknown or other

<400> SEQUENCE: 17
gacugccgnn nuagguugcc c                                                21

<210> SEQ ID NO 18
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
gaatcgaact gtcagtgact cgaaagcacg ga                                    32

<210> SEQ ID NO 19
<211> LENGTH: 21
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (10)..(11)
<223> OTHER INFORMATION: a, c, g, t, unknown or other

<400> SEQUENCE: 19
tccgtgctrn nggttcgatt c                                              21

<210> SEQ ID NO 20
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
gaatcgaact gttttcagtg ttatctcgaa agcacgga                             38

<210> SEQ ID NO 21
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
gaatcgaact gttttcagt gttattctcg aaagcacgga                            40

<210> SEQ ID NO 22
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(3)
<223> OTHER INFORMATION: a, c, g, t, unknown or other
<220> FEATURE:
<221> NAME/KEY: Variation
<222> LOCATION: (14)..(19)
<223> OTHER INFORMATION: /replace=" "
<220> FEATURE:
<221> NAME/KEY: misc_feature
<222> LOCATION: (14)..(19)
<223> OTHER INFORMATION: /note="Nucleotides given in the sequence have
      no preference with respect to those in the annotation for said
      positions"
<220> FEATURE:
<221> NAME/KEY: modified_base
<222> LOCATION: (22)..(25)
<223> OTHER INFORMATION: a, c, g, t, unknown or other
<220> FEATURE:
<221> NAME/KEY: Variation
<222> LOCATION: (28)..(33)
<223> OTHER INFORMATION: /replace=" "
<220> FEATURE:
<221> NAME/KEY: misc_feature
<222> LOCATION: (28)..(33)
<223> OTHER INFORMATION: /note="Nucleotides given in the sequence have
      no preference with respect to those in the annotation for said
      positions"
<220> FEATURE:
<221> NAME/KEY: modified_base
```

```
<222> LOCATION: (51)..(52)
<223> OTHER INFORMATION: a, c, g, t, unknown or other

<400> SEQUENCE: 22
nnnyyyyyyy agttttttty rnnnnyrttt tttaccttca gacayrryrr nn        52

<210> SEQ ID NO 23
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, g, t, unknown or other
<220> FEATURE:
<221> NAME/KEY: modified_base
<222> LOCATION: (14)..(16)
<223> OTHER INFORMATION: a, c, g, t, unknown or other
<220> FEATURE:
<221> NAME/KEY: Variation
<222> LOCATION: (30)..(35)
<223> OTHER INFORMATION: /replace=" "
<220> FEATURE:
<221> NAME/KEY: misc_feature
<222> LOCATION: (30)..(35)
<223> OTHER INFORMATION: /note="Nucleotides given in the sequence have
      no preference with respect to those in the annotation for said
      positions"
<220> FEATURE:
<221> NAME/KEY: modified_base
<222> LOCATION: (40)..(43)
<223> OTHER INFORMATION: a, c, g, t, unknown or other
<220> FEATURE:
<221> NAME/KEY: Variation
<222> LOCATION: (48)..(53)
<223> OTHER INFORMATION: /replace=" "
<220> FEATURE:
<221> NAME/KEY: misc_feature
<222> LOCATION: (48)..(53)
<223> OTHER INFORMATION: /note="Nucleotides given in the sequence have
      no preference with respect to those in the annotation for said
      positions"
<220> FEATURE:
<221> NAME/KEY: modified_base
<222> LOCATION: (56)..(57)
<223> OTHER INFORMATION: a, c, g, t, unknown or other

<400> SEQUENCE: 23
nnyyyyyyyt ccgnnncggt cgaaatattt tttttagctn nnnagctttt tttaannryr        60 rry        63

<210> SEQ ID NO 24
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: Variation
<222> LOCATION: (29)..(34)
<223> OTHER INFORMATION: /replace=" "
<220> FEATURE:
<221> NAME/KEY: misc_feature
<222> LOCATION: (29)..(34)
<223> OTHER INFORMATION: /note="Nucleotides given in the sequence have
      no preference with respect to those in the annotation for said
      positions"
<220> FEATURE:
<221> NAME/KEY: modified_base
```

```
<222> LOCATION: (39)..(42)
<223> OTHER INFORMATION: a, c, g, t, unknown or other
<220> FEATURE:
<221> NAME/KEY: Variation
<222> LOCATION: (47)..(52)
<223> OTHER INFORMATION: /replace=" "
<220> FEATURE:
<221> NAME/KEY: misc_feature
<222> LOCATION: (47)..(52)
<223> OTHER INFORMATION: /note="Nucleotides given in the sequence have
      no preference with respect to those in the annotation for said
      positions"
<220> FEATURE:
<221> NAME/KEY: modified_base
<222> LOCATION: (61)..(62)
<223> OTHER INFORMATION: a, c, g, t, unknown or other

<400> SEQUENCE: 24
rrryraggct agctacaacg actaaatttt ttttagctnn nnagcttttt ttaayrryrr    60 nn                                                                  62

<210> SEQ ID NO 25
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
gttcggaaac gaac                                                     14

<210> SEQ ID NO 26
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
gttcggaaac gtac                                                     14

<210> SEQ ID NO 27
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
gtttcggaaa cgttac                                                   16

<210> SEQ ID NO 28
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
gttttcggaa acgtttac                                                 18
```

```
<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29 gttttttcgga aacgttttac                                                      20

<210> SEQ ID NO 30
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30 gtttttttcgg aaacgttttt ac                                                   22

<210> SEQ ID NO 31
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31 gttttttttcg gaaacgtttt ttac                                                 24

<210> SEQ ID NO 32
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
cacgtacatc tcttcagttt tttcggaaac gttttttacct tcagacatag tgagt              55

<210> SEQ ID NO 33
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
actcactata rggaagagat ggacgtg                                               27
```

NUCLEIC ACID BASED FLUORESCENT SENSOR FOR MERCURY DETECTION

CROSS REFERENCE TO RELATED APPLICATION

This application claims priority to provisional application No. 60/955,316 entitled "Nucleic Acid Based Fluorescent Sensor For Mercury Detection" filed 10 Aug. 2007, the entire contents of which are hereby incorporated by reference, except where inconsistent with the present application.

FEDERALLY SPONSORED RESEARCH OR DEVELOPMENT

This subject matter of this application may have been funded in part under the following research grants and contracts: National Science Foundation Contract Numbers CTS-0120978 and DMI-0328162, and U.S. Department of Energy Contract Number DE-FG02-01-ER63179. The U.S. Government may have rights in this invention.

BACKGROUND

Mercury is a highly toxic heavy metal in the environment. Mercury exposure can cause a number of severe adverse health effects, such as damages in the brain, nerve system, immune system, kidney, and many other organs.[1] Mercury contamination comes from both nature and human activities, and an annual releasing of 4,400 to 7,500 metric tons of mercury to the environment was estimated by the United Nations Environment Programme (UNEP).[2] Therefore, highly sensitive and selective mercury sensors are very useful in understanding its distribution and pollution and in preventing mercury poisoning. Towards this goal, many fluorescent small organic molecule-based $Hg^{2+}$ sensors have been reported, which change their emission properties upon binding to $Hg^{2+}$. Most of these sensors, however, require the involvement of organic solvent, show quenched emissions, and suffer from poor selectivity.[3-11] Only a few such sensors can detection $Hg^{2+}$ in water with high sensitivity and selectivity.[12-17] $Hg^{2+}$ sensors based on foldamers,[18, 19] oligonucleotides,[20] genetically engineered cells,[21] enzymes,[22] antibodies,[23] transcriptional regulatory proteins,[24,25] DNAzymes,[26] and chemically modified optical fibers[27,28] capillary optode,[29,30] membranes,[31] electrodes,[32,33] mesoporous silica,[34] and nanoparticles[35] are also known. For environmental monitoring applications, such as detection of $Hg^{2+}$ in drinking water, a detection limit of lower than 10 nM (the toxic level defined by the US Environmental Protection Agency (EPA)) is required. However, few reported mercury sensors can reach such sensitivity.[11,21,25] We are interested in using catalytic DNA or DNAzymes to design metal sensors that can achieve the goal.[36,37]

DNAzymes are DNA-based biocatalysts.[38-42] Similar to protein enzymes or ribozymes, DNAzymes can also catalyze many chemical and biological transformations, and some of the reactions require specific metal ions as cofactors. Highly effective fluorescent and colorimetric sensors have been demonstrated for $Pb^{2+}$ and $UO_2^{2+}$ with DNAzymes.[36,37,43] These sensors showed picomolar to low nanomolar sensitivity and thousand to million-fold selectivity. In the presence of target metal ions, the fluorescence enhancement was generally greater than 10-fold, and signal generation took only 2 min or less. These sensors can be used at room temperature in aqueous solutions and no organic solvents are needed. Recently, DNAzyme-based electrochemical metal sensors are also reported.[44] Compared to protein or RNA, DNA is relatively more cost-effective to produce and more stable. DNAzymes can be denatured and renatured many times without losing their activities.[39] Therefore, DNAzymes are useful in metal detection.

It was reported that $Hg^{2+}$ can specifically bind in between two DNA thymine bases and promote such T-T mismatches into stable base pairs (FIG. 1d).[20,45,46] This property was applied by Ono and co-workers to design a fluorescent sensor for $Hg^{2+}$ detection.[20] The sensor consisted of a single-stranded thymine rich DNA with the two ends labeled with a fluorophore and a quencher, respectively. In the presence of $Hg^{2+}$, the two ends were brought close to each other, resulting in decreased fluorescence. A detection limit of 40 nM was reported.[20] Being sensitive and selective, this sensor is a "turn-off" sensor and fluorescence intensity decreased in the presence of $Hg^{2+}$, which may give false positive results caused by external quenchers or other environmental factors that can also induce fluorescence decrease. The $Hg^{2+}$ stabilization effects on T-T mismatches have also been applied to design colorimetric sensors with DNA-functionalized gold nanoparticles and a detection limit of 100 nM was achieved.[35] In previous DNAzyme work, a signaling method called catalytic beacon was designed in which the metal binding site in DNAzymes and the fluorescence signaling part are spatially separated.[36,37,47]

SUMMARY

In a first aspect, the present invention is a nucleic acid enzyme, comprising an oligonucleotide containing thymine bases. The nucleic acid enzyme is dependent on both $Hg^{2+}$ and a second ion as cofactors, to produce a product from a substrate comprising a ribonucleotide, a deoxyribonucleotide, or both.

In a second aspect, the present invention is a method of detecting $Hg^{2+}$ in a sample comprising forming a mixture comprising (1) a nucleic acid enzyme, (2) the sample, (3) a substrate, and (4) a second ion, to produce a product from the mixture; and determining the presence of the product. The enzyme comprises at least one quencher and is dependent on both the $Hg^{2+}$ and the second ion as cofactors to produce the product from the substrate. Furthermore, the substrate comprises a ribonucleotide, a deoxyribonucleotide, or both, and the substrate comprises at least one fluorophore and at least one quencher.

In a third aspect, the present invention is a method of determining the concentration of $Hg^{2+}$ in the presence of other ions, in a sample, comprising forming a mixture comprising (1) a nucleic acid enzyme, (2) the sample, (3) a substrate, and (4) a second ion, to produce a product from the mixture; determining the presence of the product; and determining the concentration of the $Hg^{2+}$ by measuring an amount of the product produced. The enzyme comprises at least one quencher and is dependent on the $Hg^{2+}$ and the second ion as cofactors to produce the product from the substrate. Furthermore, the substrate comprises a ribonucleotide, a deoxyribonucleotide, or both, and the substrate comprises at least one fluorophore and at least one quencher.

In a fourth aspect, the present invention is a sensor for $Hg^{2+}$, comprising (1) a nucleic acid enzyme, (2) a substrate, and (3) a second ion. The enzyme comprises at least one quencher and is dependent on both the $Hg^{2+}$ and the second ion as cofactors to produce a product from the substrate. Furthermore, the substrate comprises a ribonucleotide, a deoxyribonucleotide, or both, and the substrate comprises at least one fluorophore and at least one quencher.

A "nucleic acid enzyme" is a nucleic acid molecule that catalyzes a chemical reaction. The nucleic acid enzyme may be covalently linked with one or more other molecules yet remain a nucleic acid enzyme. Examples of other molecules include dyes, quenchers, proteins, and solid supports. The nucleic acid enzyme may be entirely made up of ribonucleotides, deoxyribonucleotides, or a combination of ribo- and deoxyribonucleotides.

A "sample" may be any solution that may contain an ion (before or after pre-treatment). The sample may contain an unknown concentration of an ion. For example, the sample may be paint that is tested. The sample may be diluted yet still remain a sample. The sample may be obtained from the natural environment, such as a lake, pond, or ocean, an industrial environment, such as a pool or waste stream, a research lab, a common household, or a biological environment, such as blood. Of course, sample is not limited to the taking of an aliquot of solution but also includes the solution itself. For example, a biosensor may be placed into a body of water to measure for contaminants. In such instance, the sample may comprise the body of water or a particular area of the body of water. Alternatively, a solution may be flowed over the biosensor without an aliquot being taken. Furthermore, the sample may contain a solid or be produced by dissolving a solid to produce a solution. For example, the solution may contain soil from weapon sites or chemical plants.

"Measuring an amount of the product produced" includes measuring the result of the production of a product by an enzyme. For example, in an embodiment where the substrate comprises a quencher and fluorophore and the enzyme comprises a second quencher, and cleavage of the substrate by the enzyme leads to dissociation of the product from the enzyme, "measuring an amount of the product produced" includes detecting the increase of fluorescence. Thus, the product is measured by detecting its inability to quench fluorescence.

DETAILED DESCRIPTION

Figure 1:
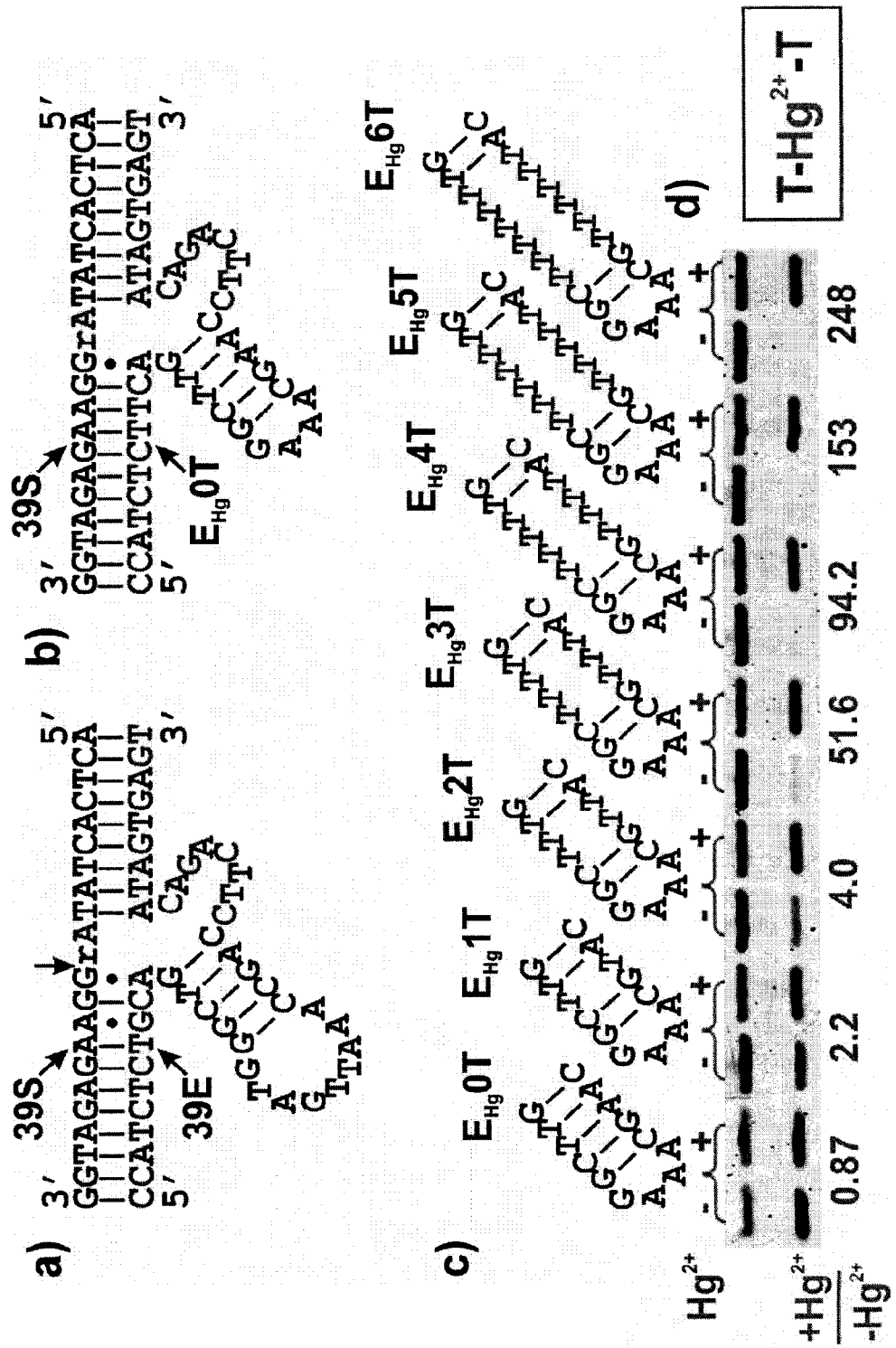
FIG. 1. (a) The secondary structure of the originally reported $UO_2^{2+}$-specific DNAzyme (SEQ ID NO: 1 (bottom strand) and SEQ ID NO: 2 (top strand)). (b) The new $UO_2^{2+}$-specific DNAzyme with the replaced stem loop. One of the A·G mismatches was also replaced by an A-T base pair (SEQ ID NO: 2 (top strand) and SEQ ID NO: 3 (bottom strand)). (c) The stem loop part of DNAzymes with zero to six T-T mismatches (top) (SEQ ID NOS: 25-31, respectively, in order of appearance from left to right). Gel image showing the fraction of cleavage after 1 min reaction time in the absence or presence of 10 μM $Hg^{2+}$ (middle). The ratio of cleavage fraction after 1 min in the presence or absence of $Hg^{2+}$ (bottom). (d) Schematics of a T-T mismatch stabilized by a $Hg^{2+}$ ion.

The present invention makes use of the discovery of new nucleic acid enzymes, which may be used in a sensor system for $Hg^{2+}$, and in a method of determining the concentration of mercury in a sample, especially in the presence of other ions. These new nucleic acid enzymes are designed from existing nucleic acid enzymes. The existing nucleic acid enzymes typically have a secondary structure necessary for activity, maintained by hybridization between bases within the nucleic acid enzyme. By introducing one or more thymine-thymine mismatches, opposite each other and within those hybridized portions of the nucleic acid enzyme which maintain the secondary structure, the secondary structure is destabilized. When $Hg^{2+}$ is present, however, it causes the T-T mismatches to form stable base pairs, stabilizing the secondary structure and restoring activity. These new nucleic acid enzymes require two different ions as cofactors: the original ion and $Hg^{2+}$.

It is also possible to artificially create such secondary structure stabilizing bases in the nucleic acid enzyme by introducing a stem loop having at least two consecutive pairs of hybridizing nucleotides in the stem loop and at least three nucleotides in between; one or two additional nucleotides may also be included at each end of the introduced section. The nucleic acid enzyme can then be made response to $Hg^{2+}$ by introducing one or more pairs of thymine bases, opposite each other and within those hybridized portions of the nucleic acid enzyme which maintain the secondary structure. Again, the result is a nucleic acid enzyme having two different ions as cofactors: the original ion and $Hg^{2+}$.

The present invention provides a simple, rapid, inexpensive, selective and sensitive method for detecting the presence of $Hg^{2+}$, with background fluorescence signal near zero, and is an important and useful tool in preventing or at least lowering health and environmental risks associated with the environmental contaminant $Hg^{2+}$. A nucleic acid enzyme that catalyzes the cleavage of a nucleic acid in the presence of two ions, $Hg^{2+}$ and a second ion, is used. The nucleic acid enzyme may be RNA (ribozyme), DNA (deoxyribozyme), a DNA/RNA hybrid enzyme, or a peptide nucleic acid (PNA) enzyme. PNAs comprise a polyamide backbone and the bases found in naturally occurring nucleosides and are commercially available, e.g., from Biosearch, Inc. (Bedford, Mass.). Nucleic acids including nucleotides containing modified bases, phosphate, or sugars may be used in the compositions and methods of the present invention. Modified bases are well known in the art and include inosine, nebularine, 2-aminopurine riboside, $N^7$-denzaadenosine, and $O^6$-methylguanosine.[55] Modified sugars and phosphates are also well known and include 2'-deoxynucleoside, abasic, propyl, phosphorothioate, and 2'-O-allyl nucleoside.[55] DNA/RNA hybrids and PNAs may be used in the compositions and methods of the present invention.

Figure 2:
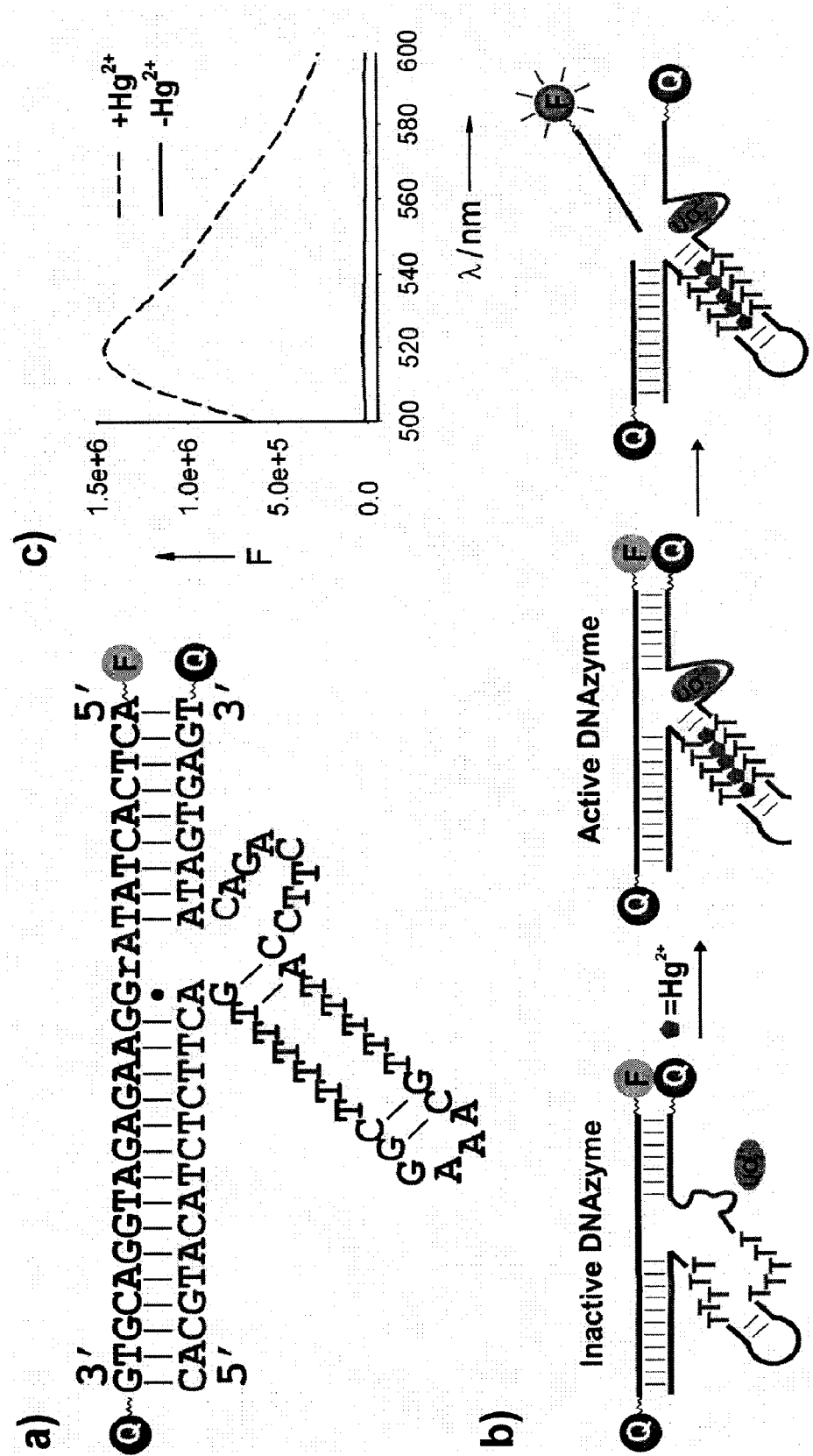
FIG. 2. (a) The secondary structure and modification of the $Hg^{2+}$ sensor DNAzyme (SEQ ID NO: 33 (top strand) and SEQ ID NO: 32 (bottom strand)). (b) Schematic presentation of the sensor design. (c) Fluorescence spectra of the sensor (with the DNAzyme and 1 μM $UO_2^{2+}$) in the absence and 8 min after addition of 0.5 μM $Hg^{2+}$.

A highly sensitive and selective catalytic beacon for mercury was rationally designed based on a uranium-specific DNAzyme, shown in FIG. 2(a). $Hg^{2+}$ enhanced the DNAzyme activity through allosteric interactions, and a series of allosteric DNAzymes with varying number of thymine-thymine mismatches were tested. The optimal DNAzymes was labeled with fluorophore and quenchers to construct a catalytic beacon. The sensor has a detection limit of 2.4 nM, which is lower than the EPA limit of $Hg^{2+}$ in drinking water. It is also highly selective and is silent to any other metal ions with up to millimolar concentration levels. The catalytic beacon performance may be further improved by incorporation of in vitro selections to optimize the allosteric interactions.[52] This work further demonstrated that DNAzymes are a great platform for metal sensing. Additional nucleic acid enzymes, using the same strategy, have also been designed, and their sequences are shown in the table along with nucleic acid enzyme used to design the highly sensitive and selective catalytic beacon for mercury.

The nucleic acid enzymes and their substrates may be used in a "turn-on" sensor for $Hg^{2+}$. These sensors are similar to those described in U.S. Pat. No. 6,890,719, except that the nucleic acid enzyme requires $Hg^{2+}$ and a second ion as cofactors. For the sensor to be responsive to $Hg^{2+}$, the second ion is included with the sensor. The second ion may be monovalent, divalent, trivalent, or polyvalent. Examples of monovalent cations include $K^+$, $Na^+$, $Li^+$, $Tl^+$, $NH_4^+$ and $Ag^+$. Examples of divalent cations include $Mg^{2+}$, $Ca^{2+}$, $Mn^{2+}$, $Co^{2+}$, $Ni^{2+}$, $Zn^{2+}$, $Cd^{2+}$, $Cu^{2+}$, $Pb^{2+}$, $Pt^{2+}$, $Ra^{2+}$, $Ba^{2+}$, $UO_2^{2+}$ and $Sr^{2+}$. Examples of trivalent cations include $Co^{3+}$, $Cr^{3+}$, and lanthanide ions ($Ln^{3+}$). Polyvalent cations include $Ce^{4+}$, and $Cr^{6+}$. The second ion also includes ions having a metal in a variety of oxidation states. Examples include K(I), Na(I), Li(I), Tl(I), Ag(I), Hg(I), Mg(II), Ca(II), Mn(II), Co(II), Ni(II), Zn(II), Cd(II), Pb(II), Pt(II), Ra(II), Ba(II), Sr(II), Co(III), Cr(III), Ln(III), Ce(IV), Cr(VI) and U(VI).

The sequences of nucleic acid enzymes are indicated in the table below, along with specific examples, and substrates for the enzymes. R, Y, r and n represent purine, pyrimidine, a ribonucleotide and any nucleotide, respectively. F indicates a fluorophore, and Q indicates a quencher. The cofactor(s) for the enzyme is (are) included in the first column. Preferably, the nucleic acid enzyme contains 38 to 100 bases.

Figure 5:
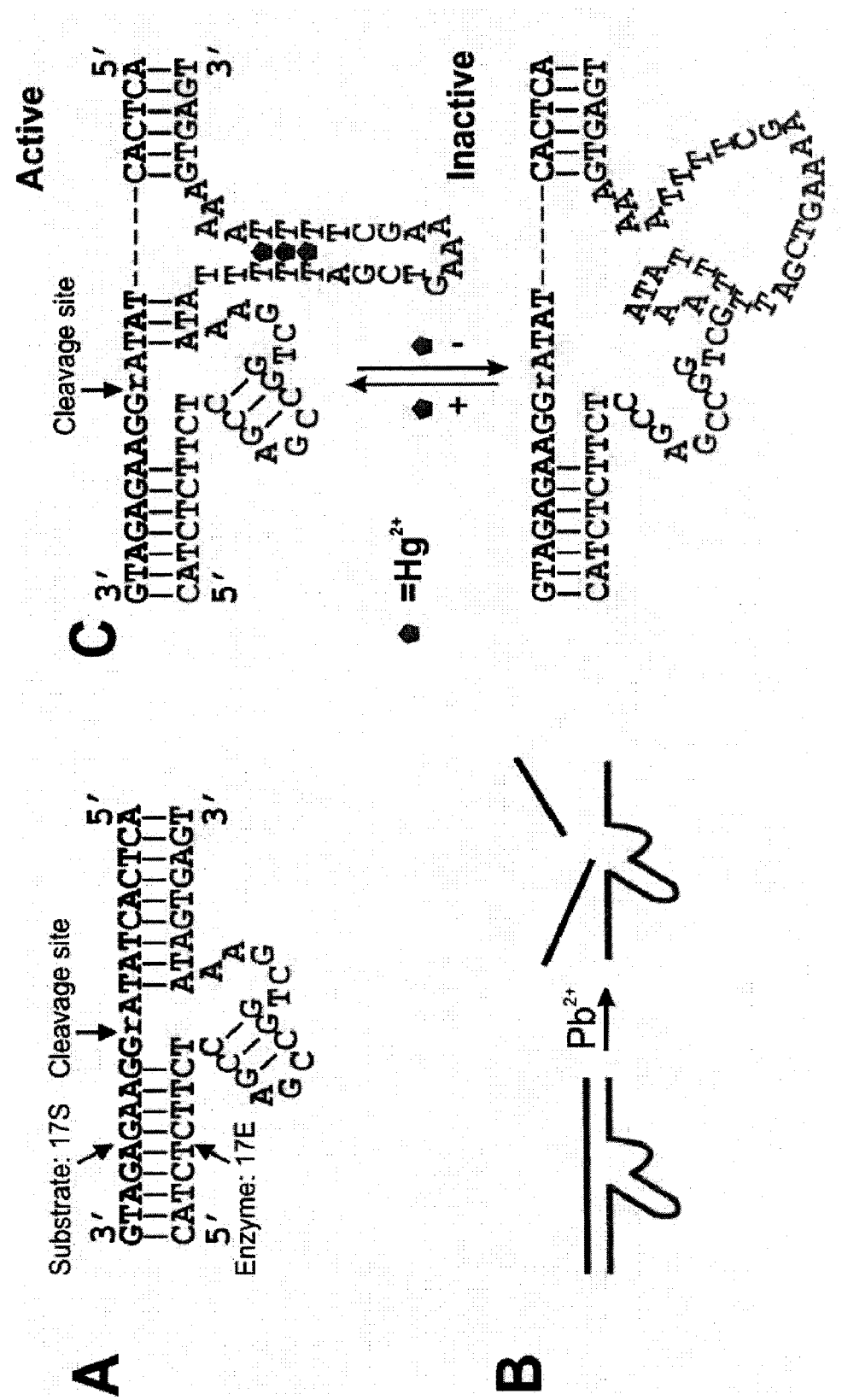
FIG. 5. Rational design of an allosteric $Hg^{2+}$ DNAzyme based on the 8-17 DNAzyme. (A) the secondary structure of the 8-17 DNAzyme (SEQ ID NO: 11 (top strand) and SEQ ID NO: 10, (bottom strand)). (B) Schematics of cleavage of the 8-17 DNAzyme by $Pb^{2+}$. (C) Insertion of a stem in the enzyme strand with T-T mismatches can make the DNAzyme into a $Hg^{2+}$ dependent enzyme (SEQ ID NO: 13 (top strand) and SEQ ID NO: 12 (bottom strand)).

| Nucleic acid enzyme 39E ($UO_2^{2+}$) (FIG. 1(a)) | 5' CCA TCT CTG CA G TCG G GT AGT TAA A CC GAC CTT CAG AC A TAG TGA GT 3' | SEQ ID NO: 1 |
| --- | --- | --- |
| 39S (substrate for 39E; FIG. 1(a)) | 3' GGT AGA GAA GGr ATA TCA CTC A 5' | SEQ ID NO: 2 |
| Nucleic acid enzyme $E_{Hg}0T$ ($UO_2^{2+}$; FIG. 1(b)) | 5' CCA TCT CTT CA G TTC G GA AA C GAA C CT TCA GAC ATA GTG AGT 3' | SEQ ID NO: 3 |
| Nucleic acid enzyme $E_{Hg}1T$ ($UO_2^{2+}$ and $Hg^{2+}$; FIG. 1(c)) | 5' CCA TCT CTT CA G TTC G GA AA C GTA C CT TCA GAC ATA GTG AGT 3' | SEQ ID NO: 4 |
| Nucleic acid enzyme $E_{Hg}2T$ ($UO_2^{2+}$ and $Hg^{2+}$; FIG. 1(c)) | 5' CCA TCT CTT CA G TTTC G GA AA C GTT A C CT TCA GAC ATA GTG AGT 3' | SEQ ID NO: 5 |
| Nucleic acid enzyme $E_{Hg}3T$ ($UO_2^{2+}$ and $Hg^{2+}$; FIG. 1(c)) | 5' CCA TCT CTT CA G TTT TC G GA AA C GTT TA C CT TCA GAC ATA GTG AGT 3' | SEQ ID NO: 6 |
| Nucleic acid enzyme $E_{Hg}4T$ ($UO_2^{2+}$ and $Hg^{2+}$; FIG. 1(c)) | 5' CCA TCT CTT CA G TTT TTC G GA AA C GTT TTA C CT TCA GAC ATA GTG AGT 3' | SEQ ID NO: 7 |
| Nucleic acid enzyme $E_{Hg}5T$ ($UO_2^{2+}$ and $Hg^{2+}$; FIG. 1(c)) | 5' CCA TCT CTT CA G TTT TTT C G GA AA C GTT TTT A C CT TCA GAC ATA GTG AGT 3' | SEQ ID NO: 8 |
| Nucleic acid enzyme $E_{Hg}6T$ ($UO_2^{2+}$ and $Hg^{2+}$; FIG. 1(c)) | 5' CCA TCT CTT CA G TTT TTT TC G GA AA C GTT TTT TA C CT TCA GAC ATA GTG AGT 3' | SEQ ID NO: 9 |
| Nucleic acid enzyme 17E ($Pb^{2+}$; FIG. 5A) | 5' CAT CTC TTC TCC GAG CCG TCG AA ATA GTG AGT 3' | SEQ ID NO: 10 |
| 17S (substrate for 17E; FIG. 5A) | 3' GTA GAG AAG GrA TAT CAC TCA 5' | SEQ ID NO: 11 |
| Nucleic acid enzyme $17E_{Hg}$ ($Pb^{2+}$ and $Hg^{2+}$; FIG. 5C) | 5' CAT CTC TTC TCC GAG CCG TCG AA ATA TTT TTA GCT GAA AAG CTT TTA AAA GTG AGT 3' | SEQ ID NO: 12 |
| $17S_{Hg}$ (substrate for $17E_{Hg}$; FIG. 5C) | 3' GTA GAG AAG GrA TAT nnn CAC TCA 5' | SEQ ID NO: 13 |

-continued

Figure 6:
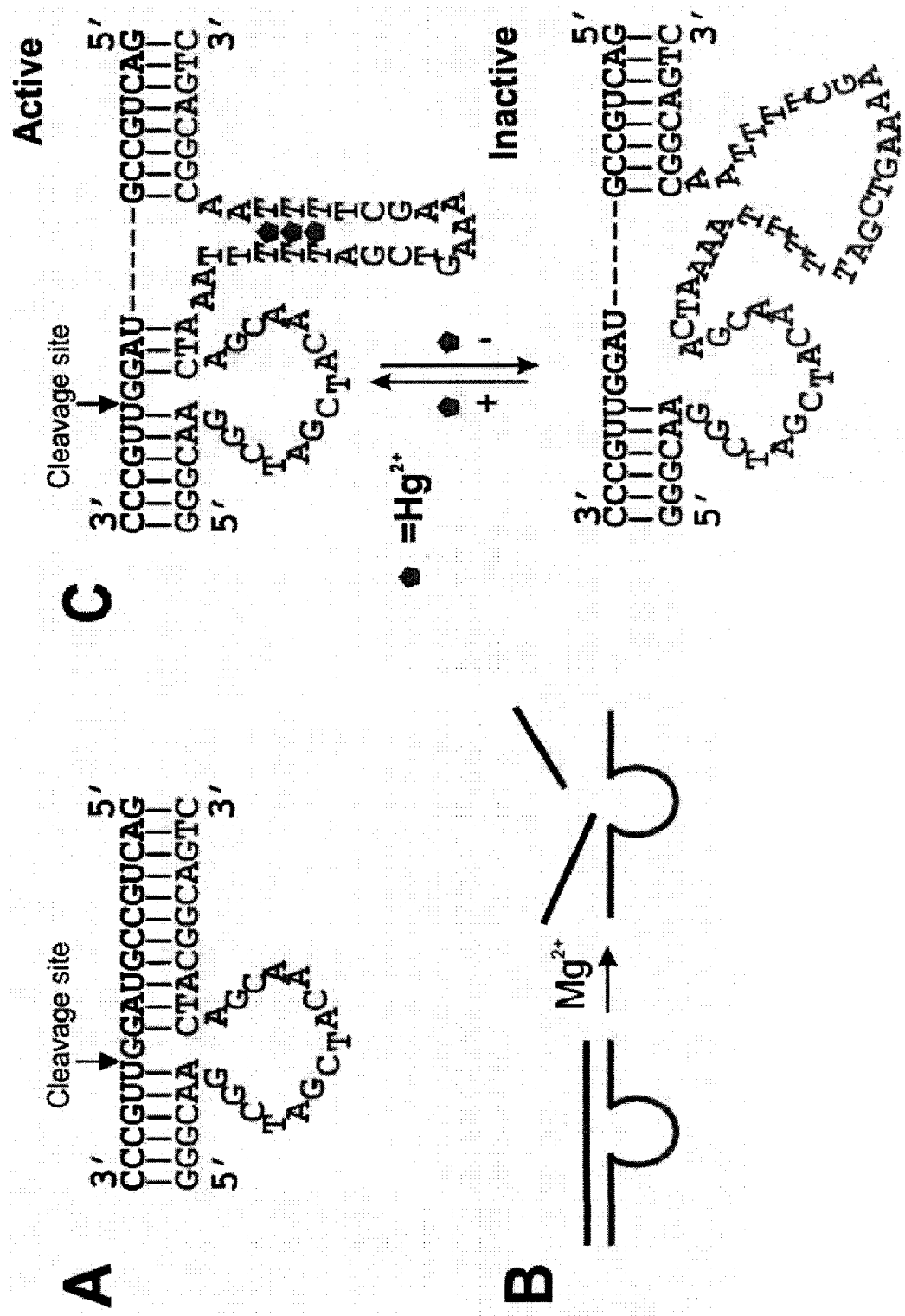
FIG. 6. Rational design of an allosteric $Hg^{2+}$ DNAzyme based on the 10-23 DNAzyme. (A) the secondary structure of the 10-23 DNAzyme (SEQ ID NO: 15 (top strand) and SEQ ID NO: 14 (bottom strand)). (B) Schematics of cleavage of the 10-23 DNAzyme by $Mg^{2+}$. (C) Insertion of a stem in the enzyme strand with T-T mismatches can make the DNAzyme into a $Hg^{2+}$ dependent enzyme (SEQ ID NO: 17 (top strand) and 16 (bottom strand)).

| | | |
|---|---|---|
| Nucleic acid enzyme 6E ($Mg^{2+}$; FIG. 6A) | 5' GGG CAA GGC TAG CTA CAA CGA CTA CGG CAG TC 3' | SEQ ID NO: 14 |
| 6S (substrate for 6E; FIG. 6A) | 3' CCC GUU G GAU GCC GUC AG 5' | SEQ ID NO: 15 |
| Nucleic acid enzyme $6E_{Hg}$ ($Mg^{2+}$ and $Hg^{2+}$; FIG. 6C) | 5' GGG CAA GGC TAG CTA CAA CGA CTA AAT TTT TAG CTG AAA AGC TTT TAA CGG CAG TC 3' | SEQ ID NO: 16 |
| $6S_{Hg}$ (substrate for $6E_{Hg}$; FIG. 6C) | 3' CCC GUU G GAU nnn GCC GUC AG 5' | SEQ ID NO: 17 |
| Nucleic acid enzyme E2112 ($Mn^{2+}$) [53] | 5' GAA TCG AAC T GTC AGT GAC TCG AAA GCA CGG A 3' | SEQ ID NO: 18 |
| S2112 (substrate for E2112) [53] | 3' CTT AGC TTGG n nr TCG TGCCT 5' | SEQ ID NO: 19 |
| Nucleic acid enzyme $E2112_{Hg(a)}$ ($Mn^{2+}$ and $Hg^{2+}$) | 5' GAA TCG AAC T GTTTC AGT GTTATC TCG AAA GCA CGG A 3' | SEQ ID NO: 20 |
| Nucleic acid enzyme $E2112_{Hg(b)}$ ($Mn^{2+}$ and $Hg^{2+}$) | 5' GAA TCG AAC T GTTTTC AGT GTTATTC TCG AAA GCA CGG A 3' | SEQ ID NO: 21 |
| Nucleic acid enzyme $E_{Hg}XT$ ($UO_2^{2+}$ and $Hg^{2+}$) (consensus sequence) | 5' nnn YYY YYY Y AGT $T_m$ YR nnnn YR $T_m$ AC CT TCA GAC A YRR YRR nn 3' (m = 1-6) | SEQ ID NO: 22 |
| Nucleic acid enzyme $17E_{Hg(x)}$ ($Pb^{2+}$ and $Hg^{2+}$) (consensus sequence) | 5' nnY YYY YYY TCC Gnn nCG GTC GAA A TA TT $T_p$ A GC T nnnn AG CT $T_p$ A A nn RYR RRY 3' (p = 1-6) | SEQ ID NO: 23 |
| Nucleic acid enzyme $6E_{Hg(x)}$ ($Mg^{2+}$ and $Hg^{2+}$) (consensus sequence) | 5' RRR YR A GGC TAG CTA CAA CGA C TA AAT T $T_q$ AG CT nnnn AGC $TT_q$ AA YRR YRR nn 3' (q = 1-6) | SEQ ID NO: 24 |

F indicates a fluorophore, and Q indicates a quencher. Essentially any fluorophore may be used, including BODIPY, fluorescein, fluoroscein substitutes (Alexa Fluor dye, Oregon green dye), long wavelength dyes, and UV-excited fluorophores. These and additional fluorophores are listed in Fluorescent and Luminescent Probes for Biological Activity. A Practical Guide to Technology for Quantitative Real-Time Analysis, Second Ed. W. T. Mason, ed. Academic Press (1999)[56]. In preferred embodiments, the fluorophore is 6-carboxyfluorescein (FAM). FAM has an excitation range of 460-500 nm.

Other fluorophores included quantum dots and silica nanoparticles. Each type of quantum dot displays a unique emission wavelength. Preferred quantum dot particles include quantum dot semiconductors, such as CdS, CdSe, CdTe, ZnS, ZnSe, ZnTe, PIn, and PbSe. Additional preferred quantum dots may include ternary quantum dots, such as $Cd_xZn_{1-x}Se$ or $CdS_xSe_{1-x}$. Additional preferred quantum dots may include core-shell quantum dots, such as those having a CdSe core and ZnS shell. The quantum dots can also have different morphologies, including dots, rods, tetrapods, and the like. In a preferred aspect, the particles are quantum dot semiconductors having average diameter from 2 to 50 nanometers.

A quencher is a molecule that absorbs the energy of the excited fluorophore. Close proximity of a fluorophore and a quencher allow for the energy to be transferred from the fluorophore to the quencher. By absorbing this energy, the quencher prevents the fluorophore from releasing the energy in the form of a photon, thereby preventing fluorescence.

Quenchers may be categorized as non-fluorescent and fluorescent quenchers. Non-fluorescent quenchers are capable of quenching the fluorescence of a wide variety of fluorophores. Generally, non-fluorescent quenchers absorb energy from the fluorophore and release the energy as heat. Examples of non-fluorescent quenchers include 4-(4'-dimethylaminophenylazo)benzoic acid) (Dabcyl), QSY-7, and QSY-33.

Fluorescent quenchers tend to be specific to fluorophores that emit at a specific wavelength range. Fluorescent quenchers often involve fluorescence resonance energy transfer (FRET). In many instances the fluorescent quencher molecule is also a fluorophore. In such cases, close proximity of the fluorophore and fluorescent quencher is indicated by a decrease in fluorescence of the "fluorophore" and an increase in fluorescence of the fluorescent quencher. Commonly used fluorescent fluorophore pairs (fluorophore/fluorescent quencher) include fluorescein/tetramethylrhodamine, IAEDANS/fluorescein, fluorescein/fluorescein, and BODIPY FL/BODIPY FL.

When choosing a fluorophore, a quencher, or where to position these molecules, it is important to consider, and preferably to test, the effect of the fluorophore or quencher on the enzymatic activity of the nucleic acid enzyme. Also, it is preferable that the fluorophore display a high quantum yield and energy transfer efficiency. Long-wavelength (excitation and emission) fluorophores are preferred because of less interference from other absorbing species. The fluorophore should also be less sensitive to pH change or to non-specific quenching by metal ions or other species.

Methods and devices for detecting fluorescence are well developed. Essentially any instrument or method for detecting fluorescent emissions may be used. For example, WO 99/27351 describes a monolithic bioelectrical device comprising a bioreporter and an optical application specific integrated circuit (OASIC).[57] The device allows remote sampling for the presence of substances in solution. Furthermore, the fluorescence may be measured by a number of different modes. Examples include fluorescence intensity, lifetime, and anisotropy in either steady state or kinetic rate change modes.[58]

Sometimes other factors in a solution such as pH, salt concentration or ionic strength, or viscosity will have an effect on fluorescence, and may even affect the hybridization of the substrate and enzyme. Therefore, in preferred methods, controls are run to determine if the solution itself, regardless of enzymatic activity, is altering the fluorescence. Such controls include the use of non-cleavable substrates and or substrate without the presence of enzyme.

The sensor system may be used to determine an amount of mercury in a sample, such as a water sample, a biological sample (such as blood or serum), or a solid sample, such as soil or paint. Preferably, a solid sample is first dissolved into solution. The samples may be diluted or concentrated prior to testing, and may also be buffered. The sensor system is able to determine an amount of mercury in the presence of other ions, preferably other metal ions, such as $Mg^{2+}$, $Ca^{2+}$, $Mn^{2+}$, $Fe^{2+}$, $Fe^{3+}$, $Co^{2+}$, $Ni^{2+}$, $Cu^{2+}$, $Zn^{2+}$, $Cd^{2+}$, $Pb^{2+}$, $UO_2^{2+}$ and $Tb^{3+}$, or in the presence of other ions.

In light of the present disclosure, one of ordinary skill in the art would know how to modify the nucleic acid biosensors to include nucleic acid enzymes. For example, a biosensor of the present invention may comprise a nucleic acid enzyme labeled with a fluorescent quencher, a substrate labeled with a fluorophore and a second fluorescent quencher, and a device to detect fluorescence such as a fluorescence microscope or a fluorometer. In a method using this embodiment, the enzyme and substrate are contacted with a sample suspected of containing an ion to which the enzyme is sensitive. Fluorescence is measured and compared to a control wherein the ion is absent. Change in fluorescence is indicative of the presence of the ion.

Of course, many variants of even this simple embodiment are included within the scope of the invention. Such variants include placing the enzyme, substrate, and sample in the well of a microtiter plate and measuring fluorescence with a microtiter plate reader. In another variation, the enzyme is attached to a solid support. When the enzyme is attached to a solid support, it is preferable that a linker is used. An exemplary linking system is biotin/streptavidin. For example, the biotin molecule may be linked to the enzyme and a plate may be coated with streptavidin. When linking an enzyme to a solid support, it is important to determine the effect of linkage on the enzymatic activity of the enzyme.

In an alternative embodiment, the solid support may be a bead and fluorescence measured using a flow cytometer. In embodiments having the enzyme attached to a solid support, the biosensor may be reusable. Old substrate and sample is removed, leaving the enzyme in place. New substrate and sample may then be added.

Recently, a $UO_2^{2+}$-specific DNAzyme was isolated by in vitro selection.[37] The secondary structure of the DNAzyme is shown in FIG. 1a, which contained a substrate strand (39S) and an enzyme strand (39E). 39S has a single RNA linkage (rA) that serves as the cleavage site. 39E binds 39S through two substrate binding arms. The catalytic core in 39E contains a stem loop and an eight-nucleotide bulge. Further studies indicated that the exact nucleotide sequence in the stem loop was unimportant for activity, as long as such a structure was maintained. For example, by replacing the stem loop to that shown in FIG. 1b, the DNAzyme was still active. In addition to the change made to the stem loop, one of the A·G mismatches in the left substrate binding arm away from the cleavage site in FIG. 1a was replaced by a A-T Watson-Crick base pair, while the other A·G mismatch close to the cleavage site was maintained. The new enzyme strand was then named $E_{Hg}0T$ (FIG. 1b), which was used as a scaffold to engineer allosteric DNAzymes that can detect $Hg^{2+}$. In addition to having such a replaceable stem loop, the uranium DNAzyme was chosen for $Hg^{2+}$ sensing also for the following reasons. First, this DNAzyme is active only in the presence of $UO_2^{2+}$ and 1 $\mu M$ $UO_2^{2+}$ is sufficient to saturate its activity.[37] Unlike other common metal ions, $UO_2^{2+}$ does not present in high concentrations in most environmental samples. Therefore, if the sensor system is saturated with $UO_2^{2+}$, external metals are unlikely to interfere with the detection. Even though uranium is a radionuclide, 1 $\mu M$ $UO_2^{2+}$ does not cause health or environmental concerns because uranium is ubiquitous in the environment, and even in drinking water, 130 nM uranium is allowed, according to the US EPA. Since the sensing application requires only 500 $\mu L$ or less sensor samples, the environmental impact is negligible. Second, the enzyme kinetics is fast. The $E_{Hg}0T$ DNAzyme shown in FIG. 1b has a rate constant of 2.0 $min^{-1}$ in the presence of 1 $\mu M$ $UO_2^{2+}$, which allows fast sensor response. Finally, the DNAzyme is relatively small in size and can be chemically synthesize and modified with high yield.

To incorporate $Hg^{2+}$ recognition elements into the DNAzyme, using rational design methods by introducing one to six T-T mismatches in stem region of $E_{Hg}0T$ (FIG. 1c). All other nucleotides were kept the same. The sequence of $E_{Hg}0T$ was designed in such a way that no stable secondary structures in the catalytic cores of all the DNAzymes (from $E_{Hg}1T$ to $E_{Hg}6T$) involving the thymine insertions were predicted by the Mfold program.[48] As a result, the DNAzymes cannot fold into their active structures in the absence of $Hg^{2+}$. Addition of $Hg^{2+}$ should quickly fold the DNAzymes into their active conformations without kinetic traps. Because the effect of $Hg^{2+}$ is spatially away from the $UO_2^{2+}$ binding site, such DNAzymes belongs to allosteric DNAzymes.[49]

Experimental Details

To test whether $Hg^{2+}$ can enhance the activity of these thymine rich

DNAzymes, 1 $\mu M$ of the DNAzyme complexes were incubated with 10 $\mu M$ $Hg^{2+}$ for 10 min. at room temperature. The substrate strand was labeled with a FAM fluorophore on the 5'-end. $UO_2^{2+}$ was added to initiate the cleavage reaction. After 1 min, the reaction was stopped and the samples were loaded onto a 20% denaturing polyacrylamide gel to separate the cleaved and uncleaved substrate. As shown in FIG. 1c, in all the DNAzymes with T-T mismatches, the fraction of cleavage was higher in the presence of $Hg^{2+}$, suggesting that $Hg^{2+}$ indeed helped to stabilize the stem loop structure and made the DNAzymes more active. For the $E_{Hg}1T$, $E_{Hg}2T$, and $E_{Hg}3T$ DNAzymes, the cleavage bands in the absence of $Hg^{2+}$ were also quite clear, suggesting that the DNAzymes may transiently fold into their active conformations even with several T-T mismatches. Such tolerability, however, dropped very quickly as the number of mismatches increases. For each DNAzyme, the ratio of cleavage fraction in the presence and absence of $Hg^{2+}$ was determined (bottom of FIG. 1c), which approximately represents the fold of activity enhancement caused by $Hg^{2+}$, and this value positively correlates with signal-to-background ratio for sensing applications.

In the above experiment, the DNAzymes were first allowed to equilibrate with $Hg^{2+}$, and $UO_2^{2+}$ was added to initiate the reaction. To detect $Hg^{2+}$, it is more desirable to add $Hg^{2+}$ to the DNAzyme/$UO_2^{2+}$ mixture to initiate the cleavage reaction. Because $E_{Hg}5T$ and $E_{Hg}6T$ showed the highest activity enhancement by $Hg^{2+}$, the rates of cleavage initiated by adding 10 μM $Hg^{2+}$ to the mixture of 1 μM DNAzyme and 1 μM $UO_2^{2+}$ was calculated. Compared to the original DNAzyme $E_{Ng}0T$, which had a rate constant of 2.0 $min^{-1}$, the values for $E_{Hg}5T$ and $E_{Hg}6T$ were 0.61 and 0.45 $min^{-1}$, respectively. Therefore, DNAzymes with more T-T mismatches had lower rates, which could be explained by that it took more time for longer DNA to find the right conformation. As a compromise between the rate of the reaction and the fold of activity enhancement, $E_{Hg}5T$ was chosen for further studies.

The $Hg^{2+}$ catalytic beacon is shown in FIG. 2a. The original $E_{Hg}5T$ enzyme strand was extended on the 5'-end by five nucleotides, and the substrate was also extended accordingly to form base pairs with the extended enzyme. Such extensions were made to increase the hybridization efficiency between the two strands. To generate signal, a fluorophore (FAM) was labeled on the 5'-end of the substrate, a quencher was labeled on the 3'-end of the enzyme, and an additional quencher was attached on the 3'-end of the substrate. Both quenchers were black hole quenchers. Such dual quencher labeling method gave very low background fluorescence and therefore allowed high signal enhancement.[50] The DNAzyme was mixed with $UO_2^{2+}$ to become a mercury sensor (FIG. 2b). In the absence of $Hg^{2+}$, the DNAzyme was incapable of binding $UO_2^{2+}$ because the active secondary structure cannot form. Addition of $Hg^{2+}$ quickly restored the stem loop structure and activated the DNAzyme to cleave the substrate, releasing the fluorophore-labeled piece and giving increased fluorescence. The fluorescence spectra of the sensor before and 8 min after addition of 500 nM $Hg^{2+}$ is shown in FIG. 2c, and ~50-fold increase in the 520 nm peak was observed. Such level of fluorescence increase is among the highest in functional nucleic acid based sensors.[51]

Figure 3:
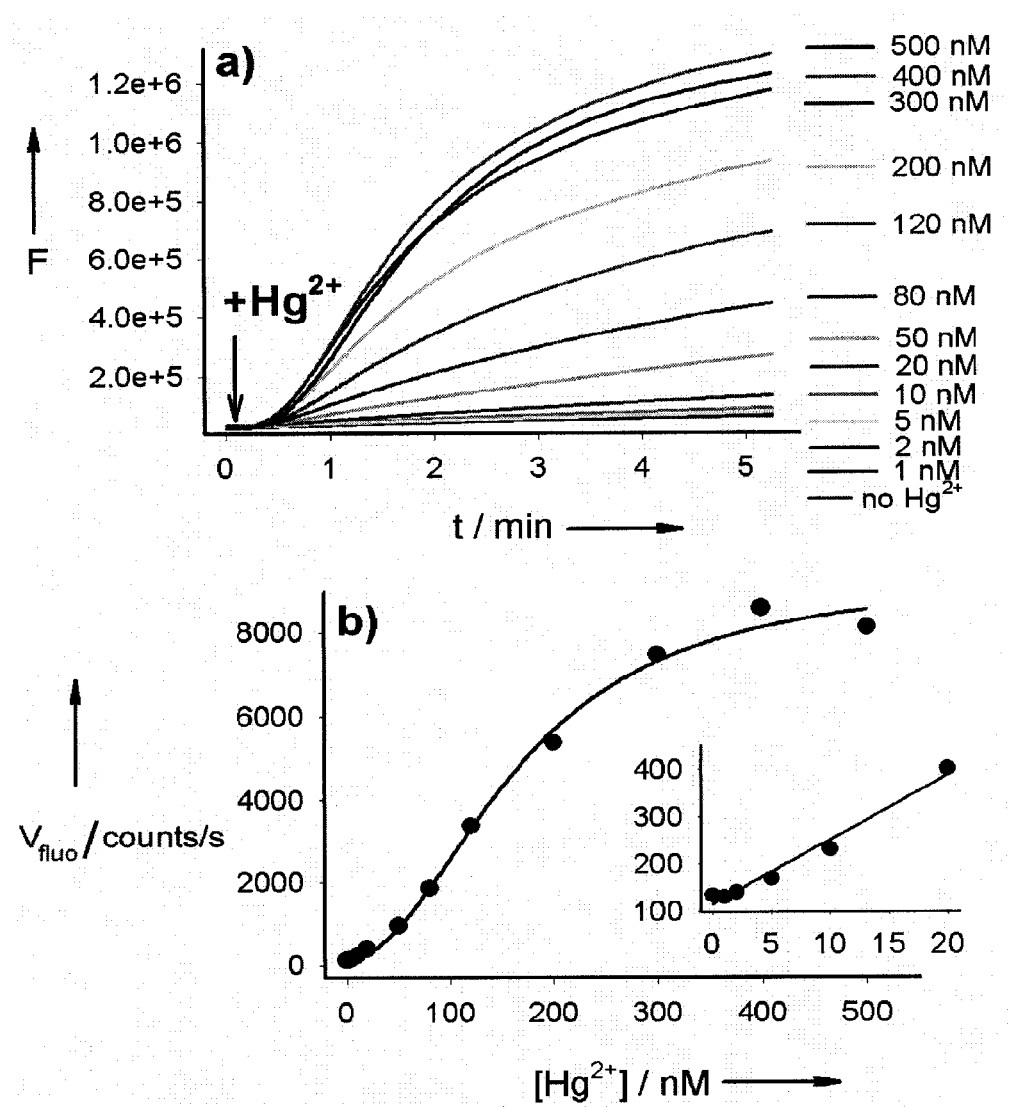
FIG. 3. Sensitivity of the $Hg^{2+}$ sensor. (a) Kinetics of fluorescence increase in the presence of varying concentrations of $Hg^{2+}$. (b) $Hg^{2+}$ dependent fluorescence increase rate. Rates were calculated in the time window of 1-2 min in (a). Inset: sensor responses at low $Hg^{2+}$ concentrations. The y-axis is the fluorescence counts increase per second. The DNAzyme and $UO_2^{2+}$ concentrations were 100 nM and 1 μM, respectively.

Given the very high fluorescence enhancement, the DNAzyme was titrated with varying concentrations of $Hg^{2+}$ and the kinetics of fluorescence enhancement at 520 nm was monitored. As shown in FIG. 3a, higher concentrations of $Hg^{2+}$ produced higher rates of emission enhancement. All the kinetic traces showed a roughly linear increase in 1-2 min time window after addition of $Hg^{2+}$ and therefore the rate of fluorescence increase in this window was calculated to quantify $Hg^{2+}$ concentration (FIG. 3b). The $Hg^{2+}$-dependent response had a sigmoid shape and was fit to a Hill plot with a Hill coefficient of 2.1. This result suggests that $Hg^{2+}$ binding to the DNAzyme is a cooperative process. Although the DNAzyme has five $Hg^{2+}$ binding sites, the DNAzyme is stable enough to cleave its substrate after binding ~2 $Hg^{2+}$ ions. The detection limit was determined to be 2.4 nM based on 3σ/slope (inset of FIG. 3b), which was a ~16-fold improvement compared to the previous oligonucleotide folding based sensor.[20] Among all the reported $Hg^{2+}$ sensors made from small and macro-molecules, this catalytic beacon has the best detection limit. The US EPA defined the toxic level of $Hg^{2+}$ in drinking water to be 2 parts-per-billion or 10 nM, which can be covered by the beacon.

Figure 4:
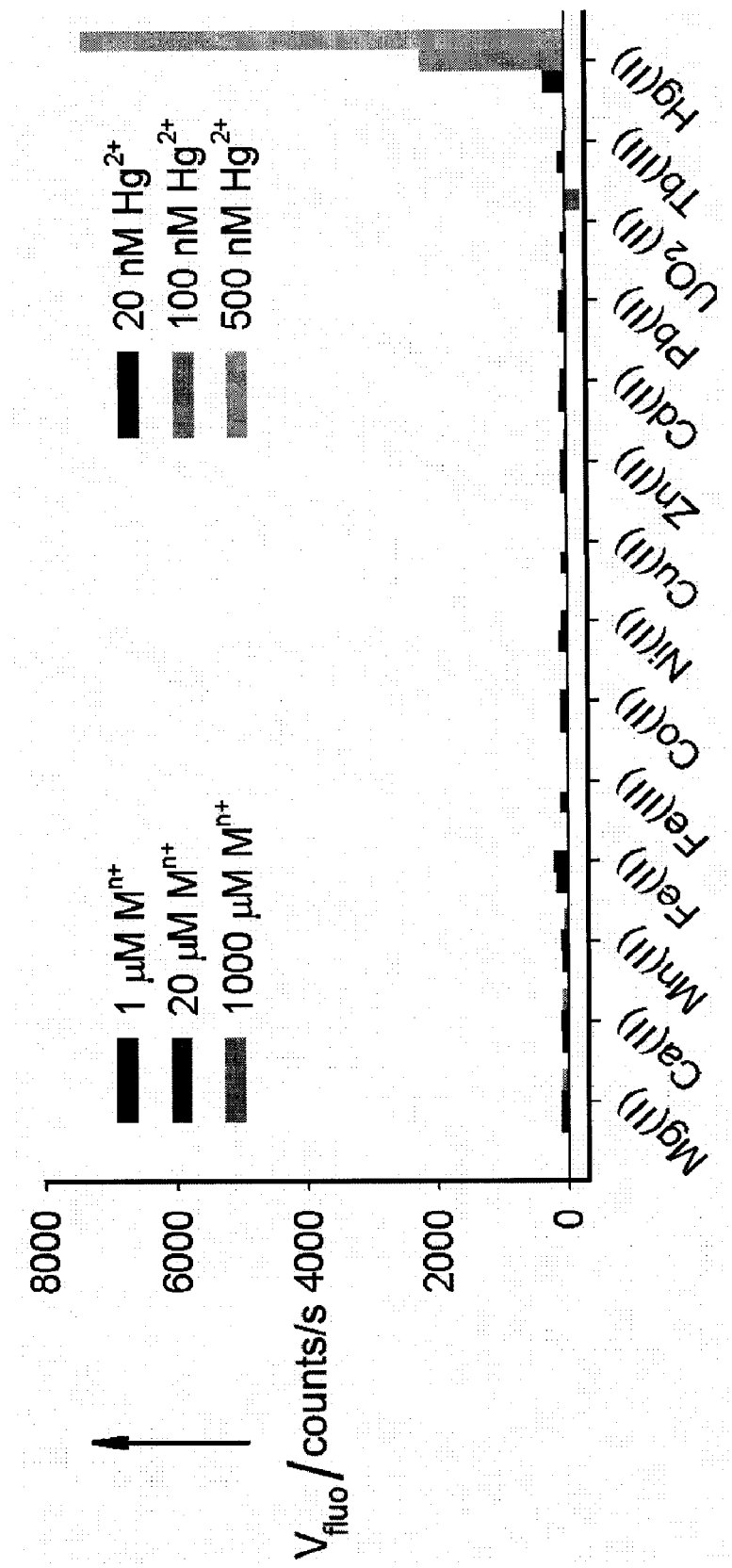
FIG. 4. Selectivity of the $Hg^{2+}$ sensor. All competing metal ions were tested at 1, 20, and 1000 μM. For comparison, sensor responses to 20, 100, and 500 nM of $Hg^{2+}$ were also presented. The DNAzyme and $UO_2^{2+}$ concentrations were 100 nM and 1 μM, respectively.

To test selectivity, the catalytic beacon responses in the presence of 13 competing metal ions were assayed (FIG. 4). Each metal was tested at three concentrations (1, 20, and 1000 μM). None of the metal ions gave responses higher than half of that produced by 20 nM $Hg^{2+}$, and the selectivity was determined to be at least 100,000-fold higher for $Hg^{2+}$ over any other metal ions (10 nM $Hg^{2+}$ versus 1 mM competing metal ions).

Materials: All DNA samples were purchased from Integrated DNA Technologies Inc. (Coralville, IA, USA) and were purified by HPLC by the company. Uranium acetate dihydrate was purchased from Fisher Scientific (Hampton, N.H., USA) and other metal salts used in this work include: $MgCl_2$, $CaCl_2$, $Mn(OAc)_2$, $Fe(NH_4)_2(SO_4)_2$, $FeCl_3$, $CoCl_2$, $NiCl_2$, $Cu(NO_3)_2$, $ZnCl_2$, $Cd(OAc)_2$, $Hg(ClO_4)_2$, $Pb(NO_3)_2$, and $TbCl_3$.

Gel based assay: 1 μM 5'-FAM labeled 39S and 1 μM enzyme were annealed in 10 mM MES buffer pH 5.5 with 300 mM $NaNO_3$ by heating at 65° C. for 1 min and subsequently cooling slowly to room temperature in 30 min. For the experiment shown in FIG. 1c, 8 μL of the annealed DNAzymes were placed in microcentrifuge tubes and 1 μL of 100 μM $Hg(ClO_4)_2$ was added. The system was allowed to incubate at room temperature for 10 min and 1 μL of 10 μM $UO_2^{2+}$ was added to initiate the cleavage reaction. The reaction was stopped after 1 min by adding 10 μL of stop buffer containing 8 M urea and 50 mM EDTA. For $E_{Hg}3T$, $E_{Hg}4T$, $E_{Hg}5T$, and $E_{Hg}6T$ DNAzymes, a 20 min time point was also taken for the samples without $Hg^{2+}$, because the fractions of cleavage for these enzymes were too low at 1 min to allow accurate calculation. The reaction mixture was then loaded to a denaturing 20% polyacrylamide gel and the gel was imaged with a Molecular Dynamics STORM 840 fluorescence imager with excitation wavelength set at 450 nm.

$Hg^{2+}$ detection: The catalytic beacon sensor was prepared by annealing 2 μM of the substrate and enzyme strand shown in FIG. 2a in 10 mM MES, pH 5.5 and 300 mM $NaNO_3$. A large volume of the same buffer was also prepared. For each detection, 25 μL of the annealed sensor was mixed with 475 μL of buffer and the final sensor concentration was 100 nM. The fluorometer (Fluoromax-P, Horiba Jobin Yvon, Edison, N.J.) was set at the kinetics mode with 15 sec intervals. The excitation was set at 490 nm and emission at 520 nm. The temperature was set at 24° C. $UO_2^{2+}$ (0.5 μL of 1 mM) was added to the DNAzyme to make a final concentration of 0.5 μM, and this mixture was used as the sensor for $Hg^{2+}$. The sensor was vortexed and placed into the fluorometer to start the kinetics reading. After the first reading, the cuvette was taken out and a small volume of $Hg(ClO_4)_2$ or other metals was added. After vortexing, the cuvette was placed back to the fluorometer to continue the reading.

REFERENCES (1) H. H. Harris, I. J. Pickering, G. N. George, *Science* 2003, 301, 1203.

(2) United Nations Environment Programme Chemicals, Geneva, Switzerland, 2002, p. 270.

(3) L. Prodi, C. Bargossi, M. Montalti, N. Zaccheroni, N. Su, J. S. Bradshaw, R. M. Izatt, P. B. Savage, *J. Am. Chem. Soc.* 2000, 122, 6769.

(4) F. Szurdoki, D. Ren, D. R. Walt, *Anal. Chem.* 2000, 72, 5250.

(5) X. Guo, X. Qian, L. Jia, *J. Am. Chem. Soc.* 2004, 126, 2272.

(6) B. Liu, H. Tian, *Chem. Comm.* 2005, 3156.

(7) A. Caballero, R. Martinez, V. Lloveras, I. Ratera, J. Vidal-Gancedo, K. Wurst, A. Tarraga, P. Molina, J. Veciana, *J. Am. Chem. Soc.* 2005, 127, 15666.

(8) K. C. Song, J. S. Kim, S. M. Park, K.-C. Chung, S. Ahn, S.-K. Chang, *Org. Lett.* 2006, 8, 3413.

(9) Y. Zhao, Z. Lin, C. He, H. Wu, C. Duan, *Inorg. Chem.* 2006, 45, 10013.

(10) W. Yang, Q. Hu, J. Ma, L. Wang, G. Yang, G. Xie, *Journal of the Brazilian Chemical Society* 2006, 17, 1039.

(11) M.-H. Ha-Thi, M. Penhoat, V. Michelet, I. Leray, *Org. Lett.* 2007, 9, 1133.

(12) E. M. Nolan, S. J. Lippard, *J. Am. Chem. Soc.* 2003, 125, 14270.

(13) Y.-K. Yang, K.-J. Yook, J. Tae, *J. Am. Chem. Soc.* 2005, 127, 16760.
(14) S.-K. Ko, Y.-K. Yang, J. Tae, I. Shin, *J. Am. Chem. Soc.* 2006, 128, 14150.
(15) E. M. Nolan, S. J. Lippard, *J. Am. Chem. Soc.* 2007, 129, 5910.
(16) J. Wang, X. Qian, *Org. Lett.* 2006, 8, 3721.
(17) J. Wang, X. Qian, J. Cui, *J. Org. Chem.* 2006, 71, 4308.
(18) Y. Zhao, Z. Zhong, *Org. Lett.* 2006, 8, 4715.
(19) Y. Zhao, Z. Zhong, *J. Am. Chem. Soc.* 2006, 128, 9988.
(20) A. Ono, H. Togashi, *Angew. Chem., Int. Ed.* 2004, 43, 4300.
(21) M. Virta, J. Lampinen, M. Karp, *Anal. Chem.* 1995, 67, 667.
(22) M. F. Frasco, J.-P. Colletier, M. Weik, F. Carvalho, L. Guilhermino, J. Stojan, D. Fournier, *FEBS Journal* 2007, 274, 1849.
(23) M. Matsushita, M. M. Meijler, P. Wirsching, R. A. Lerner, K. D. Janda, *Org. Lett.* 2005, 7, 4943.
(24) P. Chen, C. He, *J. Am. Chem. Soc.* 2004, 126, 728.
(25) S. V. Wegner, A. Okesli, P. Chen, C. He, *J. Am. Chem. Soc.* 2007, 129, 3474.
(26) R. Vannela, P. Adriaens, *Environmental Engineering Science* 2007, 24, 73.
(27) A. A. Vaughan, R. Narayanaswamy, *Sens. Actuators B* 1998, B51, 368.
(28) X.-B. Zhang, C.-C. Guo, Z.-Z. Li, G.-L. Shen, R.-Q. Yu, *Anal. Chem.* 2002, 74, 821.
(29) B. Kuswandi, R. Narayanaswamy, *Analytical Letters* 1999, 32, 649.
(30) B. Kuswandi, R. Narayanaswamy, *Sens. Actuators B* 2001, 874, 131.
(31) W. H. Chan, R. H. Yang, K. M. Wang, *Anal. Chim. Acta* 2001, 444, 261.
(32) A. Widmann, C. M. G. van den Berg, *Electroanalysis* 2005, 17, 825.
(33) V. Ostatna, E. Palecek, *Langmuir* 2006, 22, 6481.
(34) T. Balaji, M. Sasidharan, H. Matsunaga, *Analyst* 2005, 130, 1162.
(35) J.-S. Lee, M. S. Han, C. A. Mirkin, *Angew. Chem., Int. Ed.* 2007, 46, 4093.
(36) J. Li, Y. Lu, *J. Am. Chem. Soc.* 2000, 122, 10466.
(37) J. Liu, A. K. Brown, X. Meng, D. M. Cropek, J. D. Istok, D. B. Watson, Y. Lu, *Proc. Natl. Acad. Sci. U.S.A.* 2007, 104, 2056.
(38) R. R. Breaker, *Nat. Biotechnol.* 1997, 15, 427.
(39) Y. Lu, *Chem. Eur. J.* 2002, 8, 4588.
(40) J. C. Achenbach, W. Chiuman, R. P. G. Cruz, Y. Li, *Curr. Pharm. Biotechnol.* 2004, 5, 312.
(41) G. F. Joyce, *Ann. Rev. Biochem.* 2004, 73, 791.
(42) S. K. Silverman, *Nucleic Acids Res.* 2005, 33, 6151.
(43) J. Liu, Y. Lu, *J. Am. Chem. Soc.* 2003, 125, 6642.
(44) Y. Xiao, A. A. Rowe, K. W. Plaxco, *J. Am. Chem. Soc.* 2007, 129, 262.
(45) Y. Miyake, H. Togashi, M. Tashiro, H. Yamaguchi, S. Oda, M. Kudo, Y. Tanaka, Y. Kondo, R. Sawa, T. Fujimoto, T. Machinami, A. Ono, *J. Am. Chem. Soc.* 2006, 128, 2172.
(46) Y. Tanaka, S. Oda, H. Yamaguchi, Y. Kondo, C. Kojima, A. Ono, *J. Am. Chem. Soc.* 2007, 129, 244.
(47) J. Liu, Y. Lu, *Meth. Mol. Biol.* 2006, 335, 275.
(48) M. Zuker, *Nucleic Acids Res.* 2003, 31, 3406.
(49) R. R. Breaker, *Curr. Opin. Biotechnol.* 2002, 13, 31.
(50) J. Liu, Y. Lu, *Anal. Chem.* 2003, 75, 6666.
(51) W. Chiuman, Y. Li, *Nucleic Acids Res.* 2007, 35, 401.
(52) G. A. Soukup, R. R. Breaker, *Proc. Natl. Acad. Sci. U.S.A.* 1999, 96, 3584.
(53) R. P. G. Cruz, J. B. Withers, Y. Li, *Chem. Biol.* 2004, 11, 57.
(54) Y. Lu, J. Liu, U.S. Pat. No. 6,890,719 (May 10, 2005).
(55) Earnshaw & Gait, "Modified Oligoribonucleotides as site-specific probes of RNA structure and function," *Biopolymers* (John Wiley & Sons, Inc.) 48:39-55, 1998.
(56) Fluorescent and Luminescent Probes for Biological Activity. A Practical Guide to Technology for Quantitative Real-Time Analysis, Second Ed. W. T. Mason, ed. Academic Press (1999).
(57) WO 99/27351.
(58) Lakowicz, J. R. In Principles of Fluorescence Spectroscopy; 2nd ed.; Kluwer Academic/Plenum: New York, 1999.

---

What is claimed is:

1. A nucleic acid enzyme, comprising:
   an oligonucleotide substrate strand;
   an oligonucleotide enzyme strand comprising at least one stem loop, wherein at least one of the stem loops of the enzyme strand comprises one or more thymine-thymine (T-T) mismatches opposite each other, wherein the T-T mismatches form stable base pairs in the presence of $Hg^{2+}$,
   wherein the nucleic acid enzyme is dependent on both $Hg^{2+}$ and a second ion as cofactors, to produce a product from the substrate strand comprising a ribonucleotide, a deoxyribonucleotide, or both.

2. The nucleic acid enzyme of claim 1, wherein the oligonucleotide enzyme strand comprises at least 4 T-T mismatches.

3. The nucleic acid enzyme of claim 1, wherein the oligonucleotide enzyme strand comprises at least 6 T-T mismatches.

4. The nucleic acid enzyme of claim 1, further comprising a quencher.

5. The nucleic acid enzyme of claim 1, wherein the second ion is selected from the group consisting of $UO_2^{2+}$, $Pb^{2+}$, $Mg^{2+}$, $Cu^{2+}$, $Zn^{2+}$, $Co^{2+}$, $Ni^{2+}$ and $Mn^{2+}$.

6. The nucleic acid enzyme of claim 1, wherein the second ion is $UO_2^{2+}$.

7. The nucleic acid enzyme of claim 1, wherein the oligonucleotide enzyme strand comprises at least 38 bases.

8. A method of detecting $Hg^{2+}$ in a sample, comprising:
providing a mixture comprising:
the nucleic acid enzyme of claim 1,
the sample, and
a second ion,
producing a product from the mixture if $Hg^{2+}$ is present in the sample; and
determining the presence of the product, wherein the presence of the product indicates the presence of $Hg^{2+}$ in the sample.

9. The method of claim 8, wherein the second ion is selected from the group consisting of $UO_2^{2+}$, $Pb^{2+}$, $Mg^{2+}$, $Cu^{2+}$, $Zn^{2+}$, $Co^{2+}$, $Ni^{2+}$ and $Mn^{2+}$.

10. The method of claim 8, wherein the second ion is $UO_2^{2+}$.

11. The method of claim 8, wherein the method determines the concentration of $Hg^{2+}$ in the presence of other ions in the sample by measuring an amount of the product produced.

12. The method of claim 11, wherein the substrate strand comprises a fluorophore and a first quencher, and the enzyme strand comprises a second quencher.

13. The method of claim 8, wherein the substrate strand comprises a fluorophore and a first quencher, and the enzyme strand comprises a second quencher.

14. A sensor for $Hg^{2+}$, comprising:
(1) an oligonucleotide enzyme strand comprising at least one stem loop, wherein at least one of the stem loops of the enzyme strand comprises one or more thymine-thymine (T-T) mismatches opposite each other, wherein the T-T mismatches form stable base pairs in the presence of $Hg^{2+}$, and wherein the enzyme strand comprises at least one quencher,
(2) an oligonucleotide substrate strand comprising at least one fluorophore and at least one quencher, and
(3) a second ion,
wherein the sensor is dependent on both the $Hg^{2+}$ and the second ion as cofactors to produce a product from the substrate strand.

15. The sensor of claim 14, wherein the enzyme strand comprises at least 2 T-T mismatches.

16. The sensor of claim 15, wherein the enzyme strand comprises at least 4 T-T mismatches.

17. The sensor of claim 15, wherein the enzyme strand comprises at least 6 T-T mismatches.

18. The sensor of claim 14, wherein the second ion is selected from the group consisting of $UO_2^{2+}$, $Pb^{2+}$, $Mg^{2+}$, $Cu^{2+}$, $Zn^{2+}$, $Co^{2+}$, $Ni^{2+}$ and $Mn^{2+}$.

19. The sensor of claim 14, wherein the second ion is $UO_2^{2+}$.

20. The sensor of claim 15, wherein the enzyme strand comprises at least 38 bases.

21. The nucleic acid enzyme of claim 1, wherein the nucleic acid enzyme is a ribozyme (RNAzyme), deoxyribozyme (DNAzyme), a DNA/RNA hybrid enzyme, or a peptide nucleic acid enzyme (PNAzyme).

22. The nucleic acid enzyme of claim 1, wherein the substrate strand comprises a fluorophore and a first quencher, and the enzyme strand comprises a second quencher.

23. The nucleic acid enzyme of claim 22, wherein the fluorophore is 6-carboxyfluorescein.

24. The nucleic acid enzyme of claim 1, wherein the first and/or second quencher is 4-(4-dimethylaminophenylazo) benzoic acid) (Dabcyl), QSY-7, or QSY-33.

25. The nucleic acid enzyme of claim 1, wherein the oligonucleotide enzyme strand comprises one to six T-T mismatches.

26. A solid support comprising the nucleic acid enzyme of claim 1.

27. The solid support of claim 26, wherein the solid support comprises a microtiter plate or a bead.

28. The method of claim 8, wherein the sample is a water sample, biological sample, soil sample, or paint sample.

* * * * *